United States Patent
Wang et al.

(10) Patent No.: US 11,040,108 B2
(45) Date of Patent: Jun. 22, 2021

(54) AMINO ACID- AND PEPTIDE-STEROID CONJUGATES AND USE THEREOF

(71) Applicant: BRANDEIS UNIVERSITY, Waltham, MA (US)

(72) Inventors: Huaimin Wang, Waltham, MA (US); Bing Xu, Newton, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 0 days.

(21) Appl. No.: 16/097,325

(22) PCT Filed: Apr. 28, 2017

(86) PCT No.: PCT/US2017/030113
§ 371 (c)(1),
(2) Date: Oct. 29, 2018

(87) PCT Pub. No.: WO2017/189996
PCT Pub. Date: Nov. 2, 2017

(65) Prior Publication Data
US 2019/0224330 A1    Jul. 25, 2019

Related U.S. Application Data

(60) Provisional application No. 62/329,530, filed on Apr. 29, 2016.

(51) Int. Cl.
| | |
|---|---|
| A61K 47/64 | (2017.01) |
| C12N 15/62 | (2006.01) |
| A61K 45/06 | (2006.01) |
| A61K 47/55 | (2017.01) |
| A61K 47/00 | (2006.01) |
| A61K 47/54 | (2017.01) |
| A61P 35/04 | (2006.01) |
| A61K 31/282 | (2006.01) |
| A61K 31/337 | (2006.01) |
| A61K 31/351 | (2006.01) |
| A61K 31/506 | (2006.01) |

(52) U.S. Cl.
CPC ............ *A61K 47/64* (2017.08); *A61K 45/06* (2013.01); *A61K 47/00* (2013.01); *A61K 47/542* (2017.08); *A61K 47/55* (2017.08); *A61K 47/554* (2017.08); *A61P 35/04* (2018.01); *C12N 15/62* (2013.01); *A61K 31/282* (2013.01); *A61K 31/337* (2013.01); *A61K 31/351* (2013.01); *A61K 31/506* (2013.01)

(58) Field of Classification Search
None
See application file for complete search history.

(56) References Cited

U.S. PATENT DOCUMENTS

| | | | |
|---|---|---|---|
| 5,152,999 A | 10/1992 | Tokunaga et al. | |
| 7,144,877 B2 | 12/2006 | Gallop et al. | |
| 8,106,022 B2 | 1/2012 | Manoharan et al. | |
| 2008/0311667 A1 | 12/2008 | Vaya et al. | |

OTHER PUBLICATIONS

Lange, Winthrop E., et al, "Soluble steroids. II. Amino acid derivatives," Journal of Pharmaceutical Sciences (1964), 53(4), 435-7 (Year: 1964).*
Aoi, W. BioMed Research International vol. 2014, Article ID 598986, 8 pages. (Year: 2014).*
Rapp et al., "Hydrogen Bond Strengths in Phosphorylated and Sulfated Amino Acid Residues," PLOS ONE 8:1-7 (2013).
PCT International Search Report and Written Opinion for corresponding PCT/US2017/030113, dated Sep. 8, 2017.

* cited by examiner

*Primary Examiner* — Thomas S Heard
(74) *Attorney, Agent, or Firm* — Troutman Pepper Hamilton Sanders LLP (Rochester)

(57) ABSTRACT

This invention relates to a conjugate of formula (I): $(A-Z^1-)_n-Q-Z^2-D$ (I), wherein $Z^1$, $Z^2$, Q, A, D, and n are as described herein. This invention also relates to a pharmaceutical composition including a pharmaceutically acceptable carrier and a conjugate of formula (I). This invention also relates to a method making a conjugate of formula (I), and the use of the conjugate for treating cancerous conditions, modulating cell membrane microheterogeneity, stimulating an immunoresponse, and forming a network on or near the inner or outer surface of target cells.

32 Claims, 13 Drawing Sheets

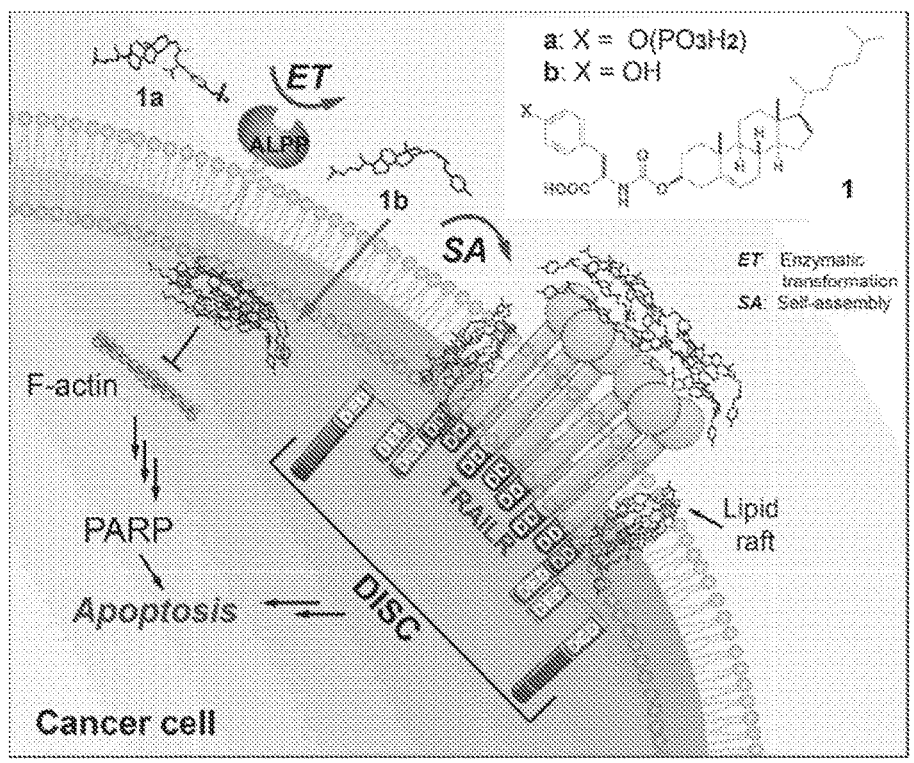
FIG. 1
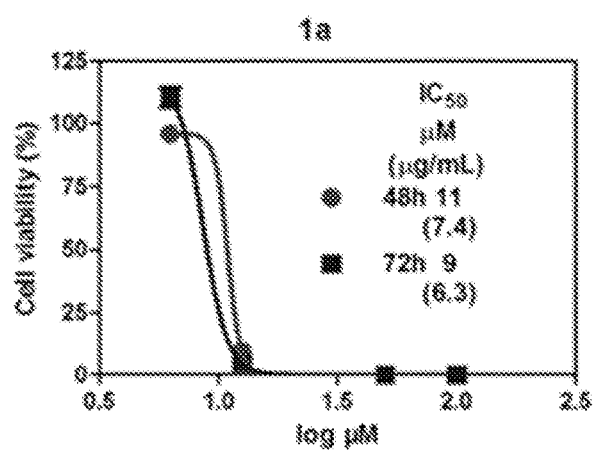 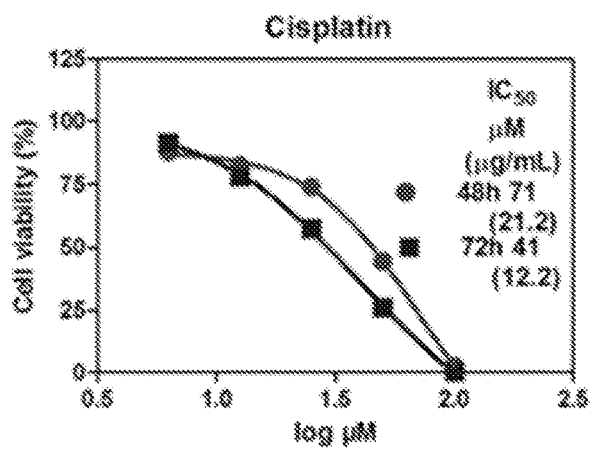
FIG. 2A          FIG. 2B

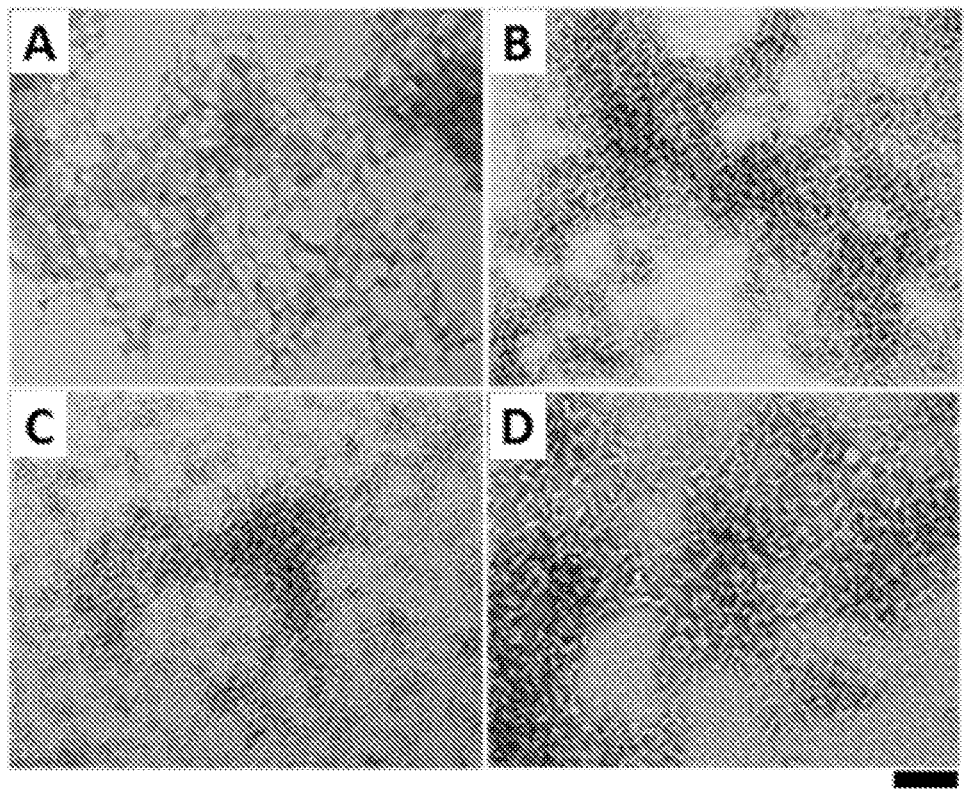
FIGS. 3A-D
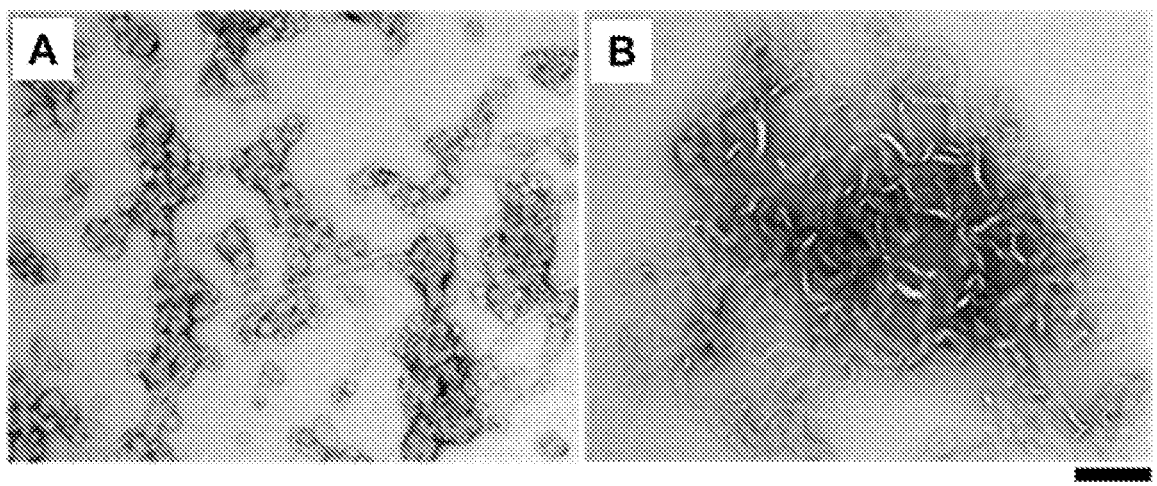
FIGS. 4A-B

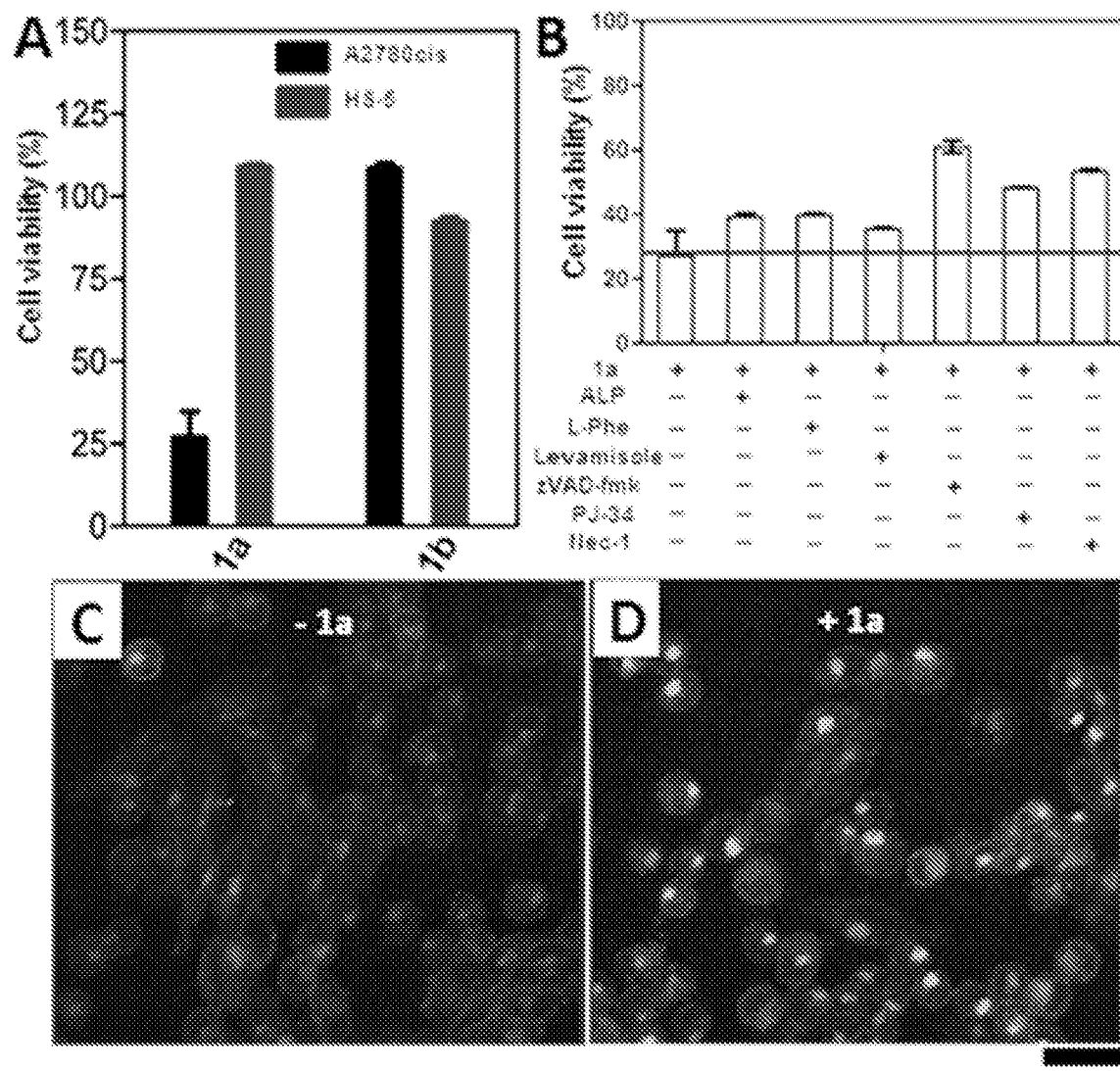
FIGS. 5A-D

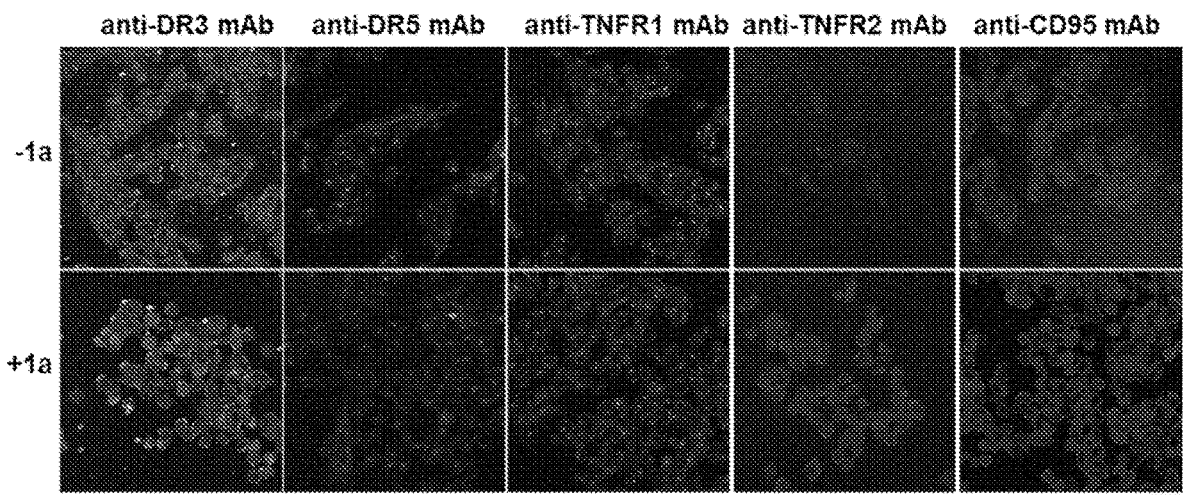
*FIG. 6*
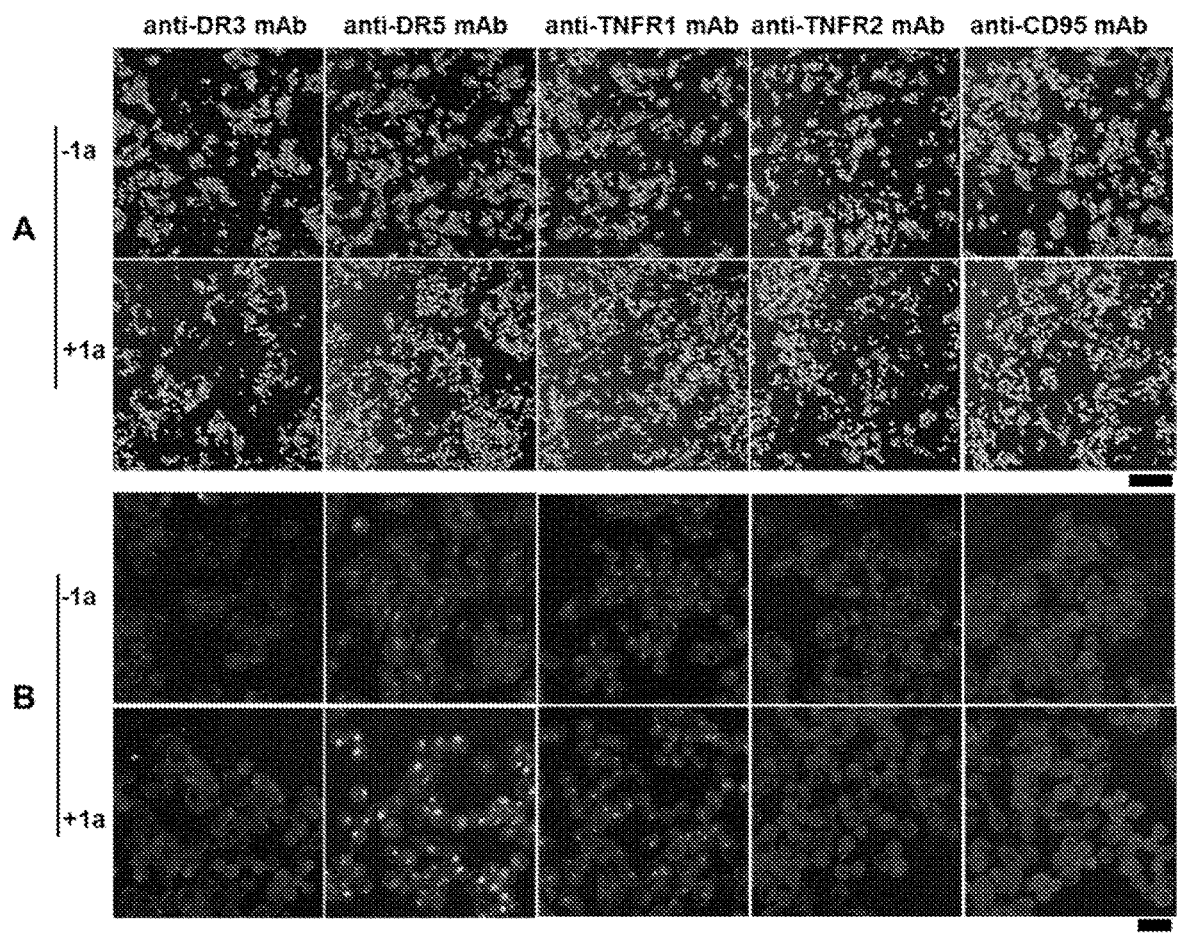
*FIGS 7A-B*

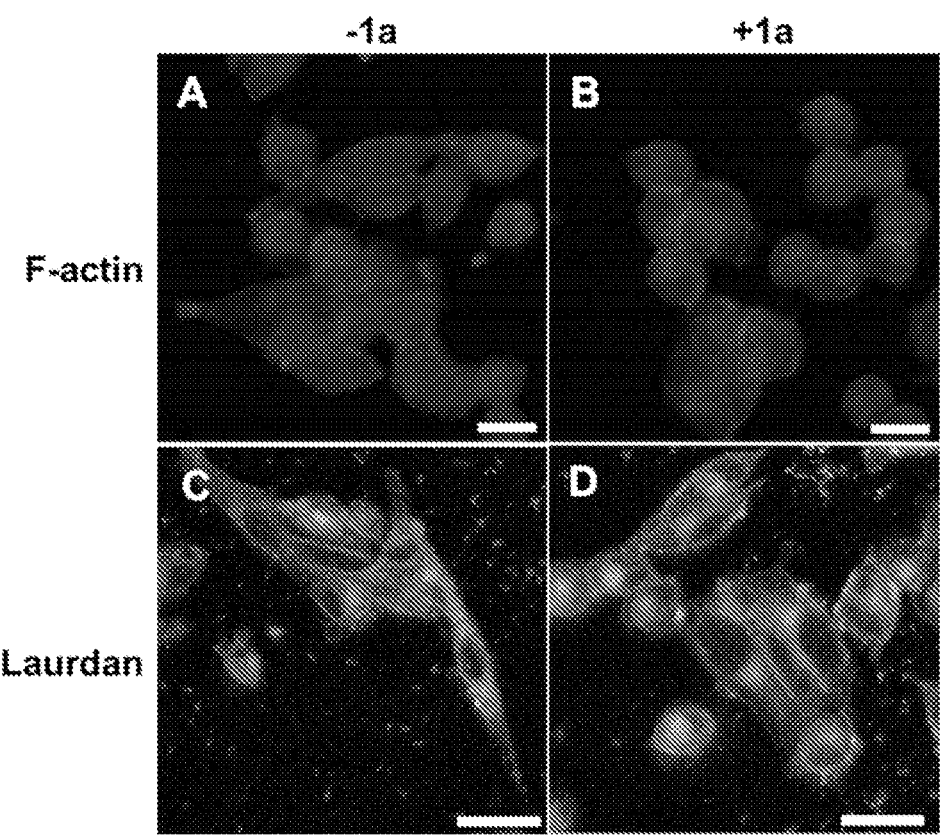
*FIGS. 8A-D*

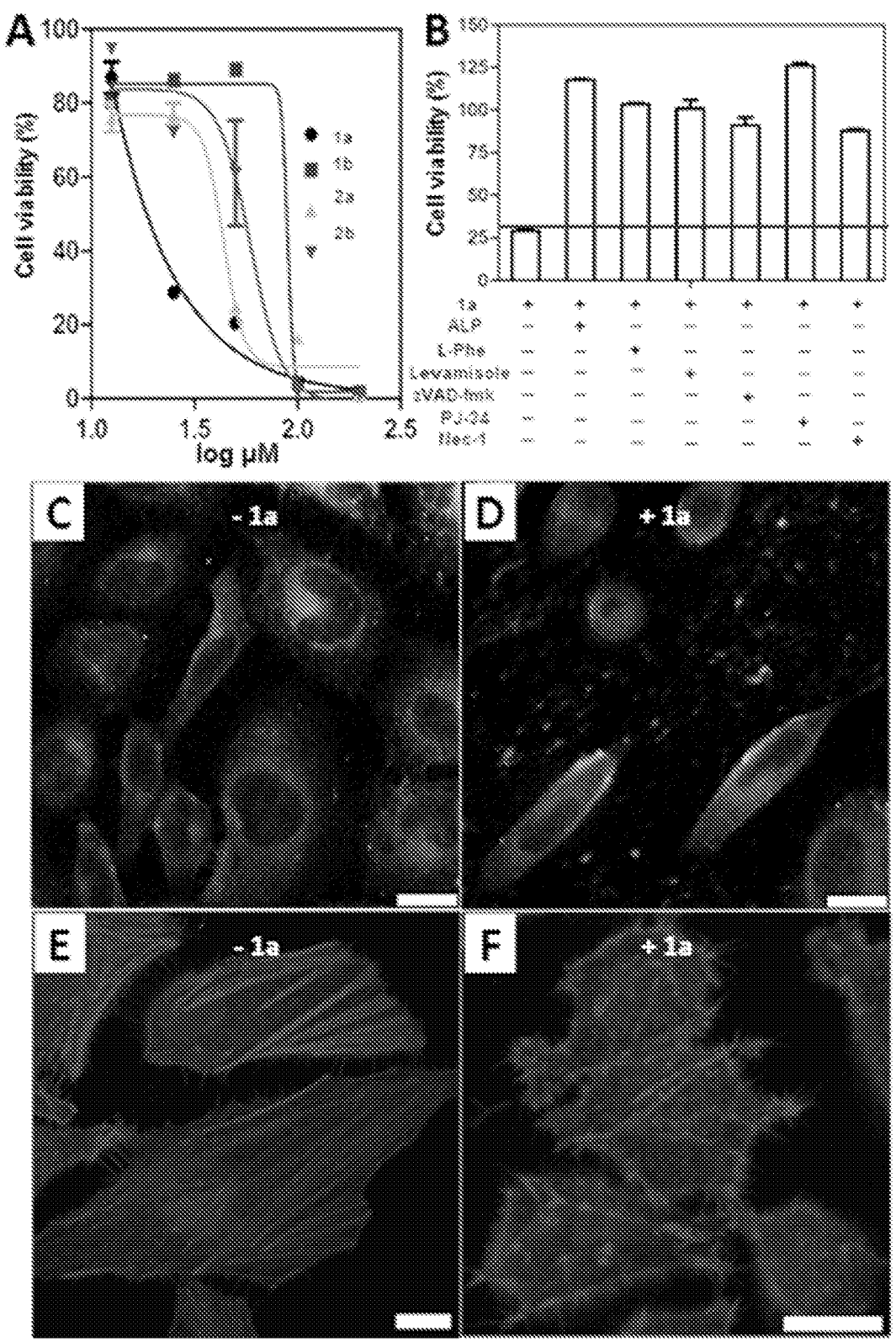
FIGS. 9A-F

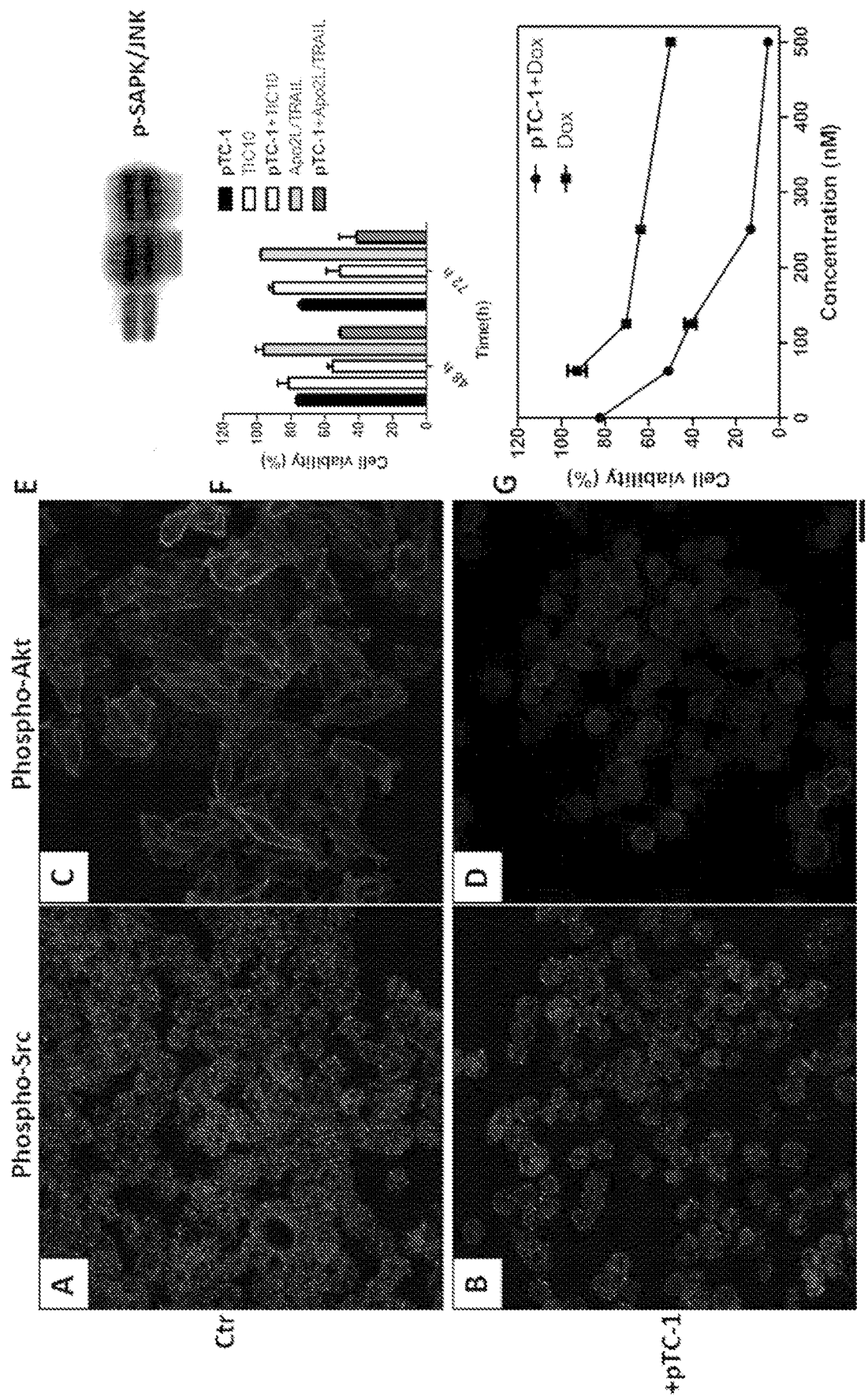
FIGS. 13A-G

AMINO ACID- AND PEPTIDE-STEROID CONJUGATES AND USE THEREOF

This application is a national stage application under 35 U.S.C. § 371 of PCT Application No. PCT/US2017/030113, filed Apr. 28, 2017, which claims the benefit of U.S. Provisional Patent Application Ser. No. 62/329,530, filed Apr. 29, 2016, which is hereby incorporated by reference in its entirety.

This invention was made with government support under grant number R01 CA142746 awarded by National Institutes of Health. The government has certain rights in this invention.

BACKGROUND OF THE INVENTION

Due to the development of the resistance to platinum-based chemotherapy, ovarian cancer, as a common cancer worldwide, remains one of the hardest to treat. For example, the five-year survival rate of ovarian cancer patients hardly improved over last decade (43% in 1999 and 46% in 2012) (Holmes D. "The Problem with Platinum," *Nature* 527: S218-S219 (2015)). This challenge in anticancer drug resistance demands innovative approaches for developing cancer therapy. Departing from the current dogma of tight ligand-receptor interactions in molecular therapy, researchers (Yang et al., "Expression Profile of Receptor-Interacting Protein 140 in the Brain: Experiment With Prenatal and Postnatal Mice," *Adv. Mater.* 19:3152 (2007); Kuang et al., "Pericellular Hydrogel/Nanonets Inhibit Cancer Cells," *Angew. Chem. Int. Ed.* 53:8104 (2014); Shi et al., "D-amino Acids Modulate the Cellular Response of Enzymatic-Instructed Supramolecular Nanofibers of Small Peptides," *Biomacromolecules* 15:3559 (2014); Zhou, "Enzyme-Instructed Self-Assembly: a Multistep Process for Potential Cancer Therapy," *Bioconjugate Chem.* 26:987 (2015); Tanaka et al., "Cancer Cell Death Induced by the Intracellular Self-Assembly of an Enzyme-Responsive Supramolecular Gelator," *J. Am. Chem. Soc.* 137:770 (2015); Pires et al., "Controlling Cancer Cell Fate Using Localized Biocatalytic Self-Assembly of an Aromatic Carbohydrate Amphiphile," *J. Am. Chem. Soc.* 137:576 (2015)) have explored enzyme catalysis and self-assembly of small molecules for developing new strategies for future cancer therapy, especially for cancers that respond poorly to conventional therapies including immunotherapy (Vaughan et al., "Rethinking Ovarian Cancer: Recommendations for Improving Outcomes," *Nat. Rev. Cancer*, 11:719 (2011)).

Recent results have validated the concept of enzyme-instructed assembly (EISA) of small molecules for selectively inhibiting cancer cells (Zhou, "Enzyme-Instructed Self-Assembly: a Multistep Process for Potential Cancer Therapy," *Bioconjugate Chem.* 26:987 (2015); Li et al., "Enzyme-Instructed Intracellular Molecular Self-Assembly to Boost Activity of Cisplatin Against Drug-Resistant Ovarian Cancer Cells," *Angew. Chem. Int. Ed.* 54:13307-13311 (2015); Shi et al., "D-Amino Acids Modulate the Cellular Response of Enzymatic-Instructed Supramolecular Nanofibers of Small Peptides," *Biomacromolecules* 15:3559 (2014); Kuang et al, "Pericellular Hydrogel/Nanonets Inhibit Cancer Cells," *Angewandte Chemie* 53:8104 (2014)), which employ enzymatic reactions to generate nanoscale assemblies of small molecules in-situ either on the surface or inside the cancer cells. However, the inhibitory concentrations of those self-assembling molecules are still higher than clinically used drugs. Therefore, there remains a need for a new approach to maximize the efficacy of EISA so that its excellent selectivity will become a unique advantage for developing translational or clinical medicines for cancer therapy.

The present invention is directed to overcoming these and other deficiencies in the art.

SUMMARY OF THE INVENTION

A first aspect of the invention relates to a conjugate of formula (I):

$$(A-Z^1-)_n-Q-Z^2-D \qquad (I),$$

wherein
 $Z^1$ is optional and, if present, is a linker containing from 1 to 30, 1 to 25, or preferably 1 to 20 atoms;
 $Z^2$ is a linker containing from 1 to 30, 1 to 25, or preferably 1 to 20 atoms;
 Q is an amino acid or a peptide, preferably a peptide comprising from 2 to 10 amino acids, wherein one or more of the amino acids is optionally phosphorylated or sulfated;
 A is H, OH, a capping moiety, or an enzymatically cleavable moiety linked to Q via covalent bond or the linker $Z^1$;
 D is a steroid moiety covalently bonded to $Z^2$; and
 n is 1 to 10.

In certain embodiments of the invention, the conjugate can be enzymatically activated by to promote nanofiber or nanoparticle formation and hydrogelation of the conjugate. Enzymatic activation can be carried out by one or more of the following events: dephosphorylation of the one or more phosphorylated amino acids, desulfation of the one or more sulfated amino acids, and enzymatic cleavage of the enzymatically cleavable moiety, A, that is linked directly or indirectly, via $Z^1$, to Q. While the conjugates according to this aspect of the invention may be able to self-assemble to form nanoparticles, nanofibers and hydrogel networks containing those nanofibers or nanoparticles in the absence of enzymatic activation, such activation may allow the thus-formed activated conjugates to more favorably self-assemble in the form of nanoparticles, nanofibers, and hydrogel networks containing those nanofibers or nanoparticles.

In certain other embodiments, Q does not include any phosphorylated or sulfated amino acids and A does not include an enzymatically cleavable moiety. In these embodiments, enzymatic activation is not required to allow for self-assembly of the conjugate. In these embodiments, the conjugate when present in an aqueous medium is able to self-assemble in the form of nanoparticles or nanofibers, and hydrogel networks containing those nanoparticles or nanofibers.

This aspect of the invention also includes nanofibers comprising a plurality of the conjugates or enzymatically-activated conjugates, nanoparticles comprising a plurality of the conjugates or enzymatically-activated conjugates, as well as hydrogel matrices containing these nanofibers or nanoparticles. These nanoparticles and nanofibers can be present in networks or aggregates that also include a therapeutic agent including, without limitation, a chemotherapeutic agent, an antiangiogenic agent, an immunomodulator agent, an antibiotic, an antigen, or a combination thereof.

A second aspect of the invention relates to a pharmaceutical composition including a pharmaceutically acceptable carrier and a conjugate according to the first aspect of the invention. One or more structurally distinct conjugates can be included.

A third aspect of the invention relates to a method for treating a cancerous condition. This method includes administering to a subject having a cancerous condition a therapeutically effective amount of the conjugate according to the first aspect or a pharmaceutical composition according to the second aspect, wherein said administering is effective to cause intracellular or pericellular self-assembly, or both intracellular and pericellular self-assembly, of the conjugate upon enzymatic cleavage of the enzymatically cleavable-moiety, enzymatic dephosphorylation of the phosphorylated amino acid, or enzymatic desulfation of the sulfated amino acid.

A fourth aspect of the invention relates to a method for modulating the cell membrane microheterogeneity. This method includes contacting a cell that expresses an esterase with hydrolytic activity, a phosphorylase, or a sulfatase with the conjugate according to the first aspect or the pharmaceutical composition according to the second aspect, wherein said contacting is effective to cause intracellular or pericellular self-assembly, or both intracellular and pericellular self-assembly, of the conjugate upon enzymatic cleavage of the enzymatically cleavable-moiety, enzymatic dephosphorylation of the phosphorylated amino acid, or enzymatic desulfation of the sulfated amino acid, thereby altering cellular membrane microheterogeneity in the contacted cell.

A fifth aspect of the invention relates to a method for stimulating immunoresponse. This method includes contacting a cell that expresses an esterase with hydrolytic activity, a phosphorylase, or a sulfatase with the conjugate according to the first aspect or the pharmaceutical composition according to the second aspect, wherein said contacting is effective to cause intracellular or pericellular self-assembly, or both intracellular and pericellular self-assembly, of the conjugate upon enzymatic cleavage of the enzymatically cleavable-moiety, enzymatic dephosphorylation of the phosphorylated amino acid, or enzymatic desulfation of the sulfated amino acid, thereby altering stimulating an immune response against the contacted cell.

A sixth aspect of the invention relates to a method for forming a network on or near the inner or outer surface, or both inner and outer surfaces, of target cells. This method includes contacting a target cell that expresses a cell surface-bound enzyme having hydrolytic activity or phosphorylase or sulfatase activity, secretes an enzyme having hydrolytic activity or phosphorylase or sulfatase activity, or both, with the conjugate according to the first aspect or the pharmaceutical composition according to the second aspect, wherein said contacting is effective to hydrolyze an enzymatically cleavable moiety, dephosphorylate a phosphorylated amino acid, or desulfate a sulfated amino acid and thereby cause in situ self-assembly of the conjugate to form a network on or near the inner or outer surface, or both inner and outer surfaces, of the target cell.

A seventh aspect of the invention relates to a method making a conjugate according to the present invention. This method includes providing a first intermediate compound having the structure:

$$LG^1\text{-}Z^2\text{-}D \quad (III),$$

wherein $LG^{-1}$ is a leaving group; and
forming the drug conjugate of formula (I) from the first intermediate compound. This step can be carried out by reacting the first intermediate compound with a compound having the structure:

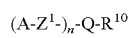

$$(A\text{-}Z^1\text{-})_n\text{-}Q\text{-}R^{10} \quad (IV),$$

wherein A, $Z^1$, Q, and n are defined as above, and $R^{10}$ is H or a leaving group.

The accompanying Examples demonstrate enzymatic, in-situ generation of nanoscale supramolecular assemblies of cholesterol conjugates for selectively killing cancer cells, including platinum-resistant ovarian cancer cells (Ozols et al., "High-Dose Cisplatin in Hypertonic Saline," Ann. Intern. Med. 100:19-24 (1984), which is hereby incorporated by reference in its entirety). Platinum resistance remains a major challenge in the treatment of ovarian cancer, a leading cause of death among women. The present application describes the use of phosphotyrosine cholesterol conjugates as well as peptide-cholesterol conjugates for selectively killing several cancer cell lines, including platinum-resistant ovarian cancer cells. Remarkably, the tyrosine-cholesterol conjugates exhibited higher potency and higher selectivity than cisplatin against drug resistant human ovarian carcinoma (A2780cis) in cell assay. Further mechanistic investigation revealed that the conjugate forms nano-assemblies both on the cell surface and inside cells, largely resulting from supramolecular self-assembly catalyzed by the overexpressed enzymes of the cancer cells. Moreover, the formed nano-assemblies not only interacted with actin filaments, but also modulated the composition of cell membrane through formation of cholesterol enhanced lipid rafts. As the first report of multifaceted nanoscale assemblies of cholesterol conjugate against platinum-resistant cancer cell, this work illustrates the integration of enzyme catalysis and self-assembly to control the assemblies of cholesterol as a promising and powerful strategy for developing multifunctional nano-assemblies towards the treatment of drug-resistant cancers. Finally, synergistic effects of conjugates in combination with a chemotherapeutic agent are identified herein, confirming that the present invention affords a new and surprising improvement for the treatment of cancer, particularly drug-resistant cancers.

BRIEF DESCRIPTION OF THE DRAWINGS

FIG. 1 is a schematic illustration showing the formation of nanoscale assemblies of a tyrosine-cholesterol derivative, 1b, following its enzyme induced activation from conjugate 1a. Derivative 1b, by forming nano-assemblies internally of the cell membrane and lipid raft in the membrane per se, simultaneously activates both extrinsic and intrinsic cell death signaling.

FIGS. 2A-B illustrate the dosage curves of 1a (FIG. 2A) and cisplatin (FIG. 2B) against A2780cis cells at 48 and 72 hours. $IC_{50}$ values shown in μM and μg/mL.

FIGS. 3A-D show TEM images of 1a (1.0 wt %) in aqueous solution (FIG. 3A); 1a (1.0 wt %) treated with ALP (1 U/mL) after 24 hours (FIG. 3B); 2a (1.0 wt %) in aqueous solution (FIG. 3C); 2a (1.0 wt %) treated with ALP (1 U/mL) after 24 hours (FIG. 3D). All at pH7.4 and the scale bar is 100 nm.

FIGS. 4A-B show TEM images of 1.0 wt % 1b in aqueous solution (FIG. 4A) and 1.0 wt % 2b in aqueous solution (FIG. 4B).

FIGS. 5A-D show cell viability of A2780cis or HS-5 cell lines incubated with 12.5 μM of 1a/1b for 48 hours (FIG. 5A), and cell viability of A2780cis treated by 1a (12.5 μM) in the presence of phosphatase inhibitors or cell death signaling inhibitors at 48 hours ([L-Phe]=[levamisole]=1 mM, [ALP]=1 U/mL, [zVAD-fmk]=50 μM, [PJ34]=1 μM, [Nec-1]=45 μM) (FIG. 5B). Confocal laser scanning microscopy (CLSM) images of A2780cis cells treated with anti- DR5 without (FIG. 3C) or with (FIG. 3D) the addition of 1a (12.5 μM) for 24 hours. Scale bar=30 μm.

FIG. 6 shows confocal laser scanning microscopy ("CLSM") images of cell death receptors without or with the treatment of 1a for 12 hours.

FIG. 7A-B are CLSM images showing cell death receptors without or with the treatment of 1a for 24 hours.

FIGS. 8A-D show CLSM images of A2780cis cells. FIGS. S13A-B show CLSM images of A2780cis cells stained with Alexa Fluor 633 Phalloidin (F-actin) and Hoechst (nuclei) without (FIG. 8A) or with (FIG. 8B) the treatment of 1a (12.5 μM) for 12 hours. FIGS. 8C-D show CLSM images of A2780cis cells stained with 10 μM laurdan without (FIG. 8C) and with (FIG. 8D) the treatment of 1a (12.5 μM) for 12 hours.

FIGS. 9A-F show the effects of 1a, 2a, 1b, and 2b on HeLa cell line. FIG. 9A shows the dosage curve of 1a, 2a, 1b, 2b against HeLa cell line at 48 hours. FIG. 9B is a graph depicting cell viability of HeLa cells treated with 1a (12.5 μM) in the presence of phosphatase inhibitors or cell death signaling inhibitors at 48 hours ([L-Phe]=[levamisole]=1 mM, [ALP]=1 U/mL, [zVAD-fmk]=50 μM, [PJ34]=1 μM, [Nec-1]=45 μM). FIGS. 9C-D are CLSM images of HeLa cells stained with laurdan (10 μM) without (FIG. 9C) and with (FIG. 9D) the addition of 1a (25 μM) for 12 hours (scale bar=20 μm). FIGS. 9E-F are CLSM images of HeLa cells stained with Alexa Fluor 633 Phalloidin (F-actin) and Hoechst (nuclei) (FIG. 9E) without and (FIG. 9F) with the addition of 1a (25 μM) for 12 hours (scale bar=15 μm).

FIG. 12C are CLSM images showing the generation of ROS as measured by dehydroethidium (DHE, λex=543 nm, emission was detected at 575-625 nm) in A2780cis without and with treatment with the 1a (12.5 μM) for 12 hours.

FIGS. 13A-G show that 1a decreases the expression of Src (FIGS. 13A-B) and Akt (FIGS. 13C-D) in A2780cis cell lines after the treatment of 1a (12.5 μM) for 24 hours; time-dependent western blot shows the expression levels of p-SAPK/JNK in A2780cis cell lines (FIG. 13E); 1a enhance the effect of different anti-cancer agents: TIC 10 and Apo2L/TRAIL (FIG. 13F) and doxorubicin (FIG. 13G).

DETAILED DESCRIPTION OF THE INVENTION

Figure 10:
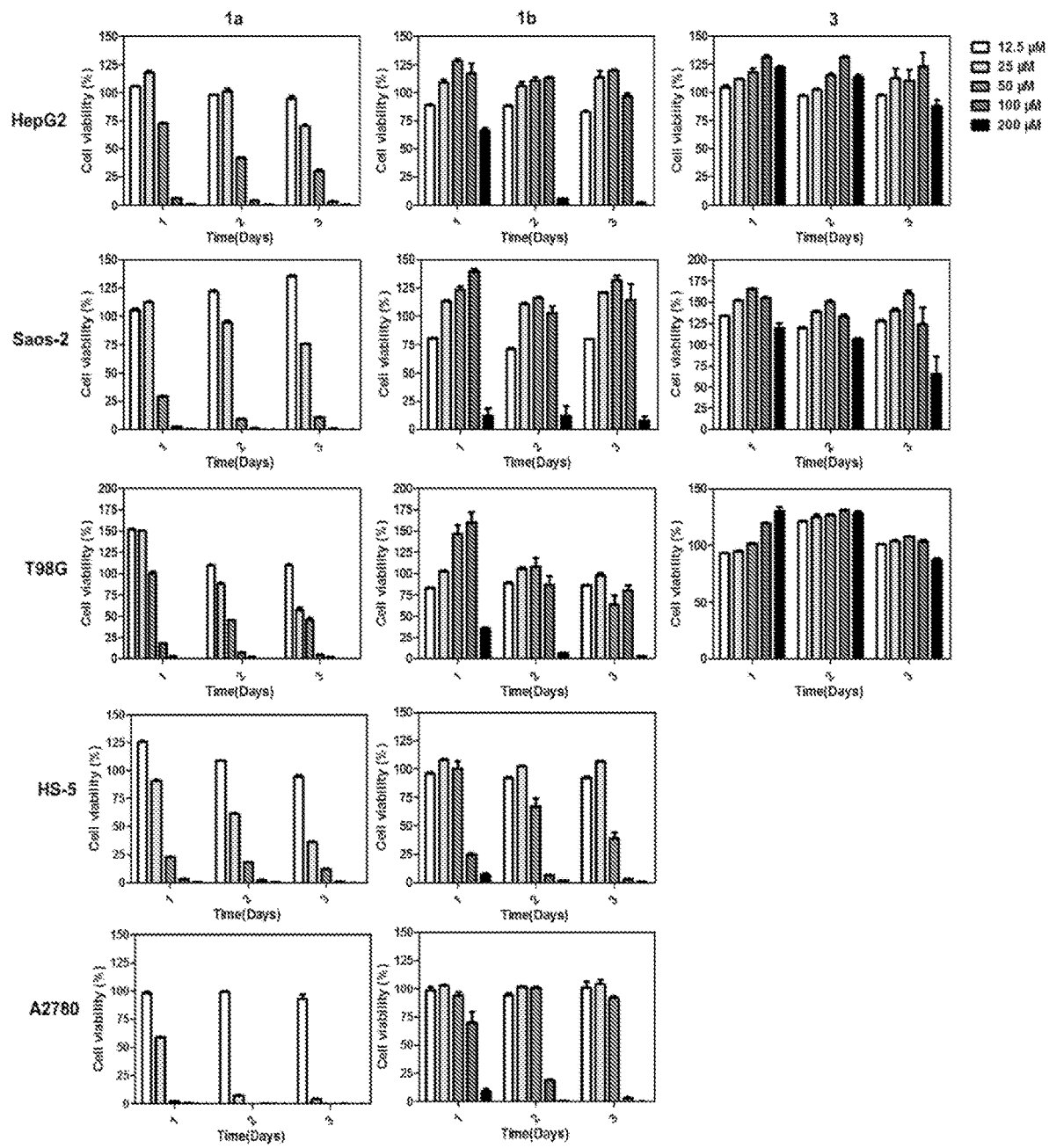
FIG. 10 is a panel of graphs that show cell viability of HepG2, Saos-2, T98G, HS-5 and A2780 cells treated with 1a, 1b, and 3 at 24, 48 and 72 hours.

The present invention relates to new amino acid- or peptide-steroid conjugates and the use thereof in formulating pharmaceutically acceptable compositions, and the use of such conjugates or compositions for various uses including, without limitation, modulating the cell membrane microheterogeneity, stimulating an immune response, treating a cancerous condition, and forming a network on or near the inner or outer surface, or both inner and outer surfaces, of target cells.

A first aspect of the invention relates to a conjugate of formula (I):

$$(A-Z^1-)_n-Q-Z^2-D \qquad (I),$$

wherein $Z^1$ is optional and, if present, is a linker containing from 1 to 30, 1 to 25, or preferably 1 to 20 atoms;

$Z^2$ is a linker containing from 1 to 30, 1 to 25, or preferably 1 to 20 atoms;

Q is an amino acid residue or a peptide, preferably comprising from 2 to 10 amino acids, wherein one or more of the amino acids is optionally phosphorylated or sulfated;

A is H, OH, a capping moiety, or an enzymatically cleavable moiety linked to Q via covalent bond or the linker $Z^1$;

D is a steroid moiety covalently bonded to $Z^2$; and n is 1 to 10, preferably 1 to 5, 1 to 4, 1 to 3, or either 1 or 2.

According to one embodiment, at least one of (i) A being the enzymatically cleavable moiety or (ii) Q including a phosphorylated or sulfated amino acid is present; and the conjugate is capable of self-assembly in the presence of an enzyme that hydrolyzes the enzymatically cleavable-moiety, an enzyme that dephosphorylates the phosphorylated amino acid, or an enzyme that desulfates the sulfated amino acid.

According to one embodiment, Q is a single amino acid. The amino acid can be D-amino acid or L-amino acid.

The term "amino acid" is intended to embrace all compounds, whether natural or synthetic, which include both an amino functionality and an acid functionality, including amino acid analogues and derivatives. In certain embodiments, the amino acids contemplated in the present invention are those naturally occurring amino acids found in proteins, or the naturally occurring anabolic or catabolic products of such amino acids, which contain amino and carboxyl groups. Amino acids, as used herein, may include both non-naturally and naturally occurring amino acids. The amino acid can be D-amino acid or L-amino acid.

According to one embodiment, the amino acid is an aromatic amino acid. Aromatic amino acids used in of the present invention include, without limitation, the natural amino acids tyrosine, phenylalanine, L-3,4-dihydroxyphenylalanine, tryptophan, 5-hydroxytryptophan, and histidine.

According to another embodiment, the amino acid is one that is capable of being phosphorylated or sulfated. Exemplary amino acids capable of being phosphorylated or sulfated include, without limitation, tyrosine, a tyrosine derivative, serine, a serine derivative, threonine, a threonine derivative, histidine, and a histidine derivative. Any known or hereinafter developed tyrosine derivatives, serine derivatives, threonine derivatives, or histidine derivatives can be used in the present invention, as long as the conjugate is capable of self-assembly. Exemplary derivatives of these amino acids include phosphorylated amino acids or sulfated amino acids.

According to another embodiment, Q is a peptide. The peptides can have any length as long as the conjugate is capable of self-assembly. In certain embodiments, the peptide may contain up to about 35 amino acids, up to about 30 amino acids, up to about 25 amino acids, up to about 20 amino acids, up to about 15 amino acids, or up to about 10 amino acids. In certain embodiments, Q is a peptide containing from 2 to 10 amino acids, such as between 2 to 5 amino acids or between 2 to 8 amino acids.

The amino acid residues that form the peptide can be any naturally occurring or non-naturally occurring amino acid, but preferably the peptide includes one or more aromatic amino acids as described above, one or more amino acids capable of being phosphorylated or sulfated as described above, or both.

The peptides can include all D-amino acids, all L-amino acids, or a mixture of L-amino acids and D-amino acids. In preferred embodiments, the peptide includes only D-amino acids or a mixture of D-amino acids and L-amino acids where the D-amino acid content is greater than 50%, 60%, 70%, 80%, 90%, or 95%.

In certain embodiments, the peptide can include one or more amino acids whose side-chain is easily conjugated to, e.g., a fluorophore, a cytotoxic agent such as a chemotherapeutic agent, an antiangiogenic agent, or an immunomodulating agent, an antibiotic, an antigen, or a thermoablative (paramagnetic) particle. Numerous examples of each of these categories are well known in the art.

Exemplary amino acids that can be derivatized include lysine or arginine, whose terminal amino group of its side chain is reactive in conjugation procedures. Examples of conjugating a chemotherapeutic agent (e.g., doxorubicin, daunorubicin, taxol) to a Lys sidechain are described in DeFeo-Jones et al., *Nature Med.* 6(11):1248-52 (2000), Schreier et al., *PlosOne* 9(4):e94041 (2014), Gao et al., *J Am Chem Soc.* 131:13576 (2009), each of which is hereby incorporated by reference in its entirety. An examples of conjugating a fluorophore, such as 4-nitro-2,1,3-benzoxadiazole ("NBD") to a Lys sidechain is described in Gao et al., *Nat. Commun* 3:1033 (2012), which is hereby incorporated by reference in its entirety.

In general, guanidine groups present in arginine can be reacted with reagents possessing guanidine-reactive groups using known reaction schemes. Exemplary guanidine reactive functional groups include, without limitation, NHS esters using gas phase synthesis (McGee et al., *J. Am. Chem. Soc.,* 134 (28):11412-11414 (2012), which is hereby incorporated by reference in its entirety).

In general, thiol groups present in cysteine (or cysteine derivative) side chains can be reacted with reagents possessing thiol-reactive functional groups using known reaction schemes. Exemplary thiol-reactive functional groups include, without limitation, iodoacetamides, maleimides, and alkyl halides. Reagents to be conjugated include those listed above.

In general, carboxyl groups present in glutamic or aspartic acid side chains, or at the C-terminal amino acid residue, can be reacted with reagents possessing carboxyl-reactive functional groups using known reaction schemes. Exemplary carboxyl-reactive functional groups include, without limitation, amino groups, amines, bifunctional amino linkers. Reagents to be conjugated include those listed above.

In certain embodiments, A is H, OH, the capping moiety, or the enzymatically cleavable moiety linked to Q via covalent bond.

According to one embodiment, A is present at the N-terminal side of the amino acid or peptide of Q, and A is either H or the capping moiety.

Capping moiety, A, can be selected from the group consisting of an alkyl, alkylacyl, aryl, arylacyl (e.g., phenylacetyl and napthylacetyl), heteroaryl, heteroarylacyl, a fluorophore, a chemotherapeutic agent, an antiangiogenic agent, an immunomodulator agent, an antibiotic, an antigen, a thermoablative (paramagnetic) particle, and hydrophilic groups. To facilitate the attachment of one or more of these groups to the N-terminal side of the amino acid or peptide, these various capping moieties can be provided with an amino-reactive group such as a carboxylic acid moiety that facilitates amide bond formation. The N-terminal attachment of the fluorophore NBD is described in co-pending PCT Application No. PCT/US16/19866 to Brandeis University, entitled "Synthetic Peptides and Enzymatic Formation of Intracellular Hydrogels," which is hereby incorporated by reference in its entirety. Exemplary drugs for N-terminal conjugation include, without limitation, doxorubicin (Zhang et al., "Cellular Uptake and Cytotoxicity of Drug-Peptide Conjugates Regulated by Conjugation Site," *Bioconjug Chem.* 24(4):604-613 (2013), which is hereby incorporated by reference in its entirety), daunomycin (Varga, "Hormone-drug conjugates," *Methods in Enzymology* 112:259-269 (1985), which is hereby incorporated by reference in its entirety), methotrexate (Radulovic et al., "Cytotoxic analog of somatostatin containing methotrexate inhibits growth of MIA PaCa-2 human pancreatic cancer xenografts in nude mice," *Cancer Letters* 62:263-271 (1992), which is hereby incorporated by reference in its entirety), and paclitaxel (see Gao et al., *J. Am. Chem. Soc.* 131(38):13576-13577 (2009), showing Lys-conjugated paclitaxel using succinic anhydride and NHS succinate, which is hereby incorporated by reference in its entirety). Cytotoxic nucleoside analogs or nucleobases that can be incorporated at the N-terminal end of the peptide include, without limitation, vidarabine, cytarabine, gemcitabine, fludarabine, cladribine, pentostatin, 6-mercaptopurine, thioguanine, and fluorouracil. These and other known attachments schemes can be used to facilitate attachment of other capping moieties.

According to another embodiment, A is present at the C-terminal side of the amino acid or peptide of Q, and A is either OH, the capping moiety, or the enzymatically cleavable moiety linked to Q via covalent bond. Capping moiety, A, is selected from the group consisting of an alkyl, alkylamino, aryl, arylamino, heteroaryl, heteroarylamino, a fluorophore, a chemotherapeutic agent, an antiangiogenic agent, an immunomodulator agent, an antibiotic, an antigen, and a thermoablative (paramagnetic) particle. To facilitate the attachment of one or more of these groups to the C-terminal side of the amino acid or peptide, these various capping moieties can be provided with a carboxylic acid-reactive group such as an amino moiety that facilitates amide bond formation or an alcohol moiety that facilitates formation of an ester bond.

In some embodiments, A is the enzymatically cleavable moiety.

In certain embodiments, the enzymatically cleavable moiety comprises a substrate of a hydrolytic enzyme. Such substrates include, for example, an ester, a carbonate, a thiocarbonate, a carbamate, a carboxylate, a diacyl anhydride, or an amide. The enzymatically cleavable moiety may optionally include a taurine or hypotaurine residue covalently bonded to the substrate of a hydrolytic enzyme.

Exemplary enzymatically cleavable moieties containing taurine or hypotaurine include, without limitation:

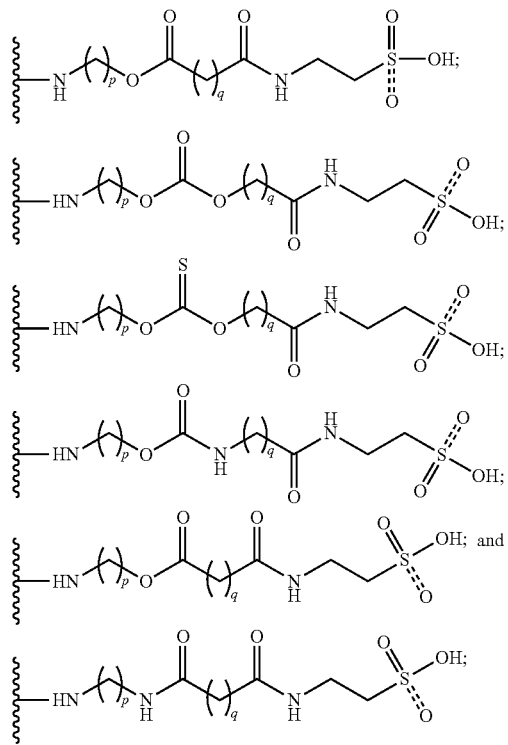

where, in each of the structures above, p and q are independently integers from 1 to 5.

The optional linker $Z^1$ can include any suitable chemical moiety containing from 1 to 20 atoms which can link A to Q. The linker $Z^2$ can include any suitable chemical moiety containing from 1 to 20 atoms which can link Q (the peptide or amino acid) to D (the steroid moiety). $Z^1$ and $Z^2$ are independent from one another, and each occurrence thereof can be a saturated or unsaturated, branched or unbranched, carbon chain of from 1 to about 20 atoms in length, which can be optionally substituted throughout the chain and can include from 1 to 10 heteroatoms in the chain. Suitable optional substituents include, but are not limited to, —NO$_2$, —CN, halogen, oxo, $C_{1-6}$ alkyl, $C_{1-6}$ haloalkyl, $C_{1-6}$ hydroxyalkyl, $C_{1-6}$ alkoxy, $C_{1-6}$ alkoxyalkyl, $C_{3-6}$ cycloalkyl, $C_{4-7}$ cycloalkylalkyl, aryl, and heteroaryl. Suitable heteroatoms include, but are not limited to, O, S, N, and Si.

The term "halogen" means fluoro, chloro, bromo, or iodo.

The term "oxo" means =O group.

The term "alkyl" means an aliphatic hydrocarbon group which may be straight or branched. When not otherwise restricted, the term refers to an alkyl of 20 or fewer carbons. Lower alkyl refers to alkyl groups having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, and the like.

The term "haloalkyl" means both branched and straight-chain alkyl substituted with one or more halogen, wherein the alkyl group is as herein described.

The term "hydroxyalkyl" means both branched and straight-chain alkyl substituted with one or more hydroxy groups, wherein the alkyl group is as herein described.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring.

The term "cycloalkyl" means a non-aromatic, saturated or unsaturated, mono- or multi-cyclic ring system of about 3 to about 7 carbon atoms, or of about 5 to about 7 carbon atoms, and which may include at least one double bond. Exemplary cycloalkyl groups include, without limitation, cyclopropyl, cyclobutyl, cyclopentyl, cyclohexyl, cycloheptyl, cyclopropenyl, cyclobutenyl, cyclopentenyl, cyclophenyl, anti-bicyclopropane, and syn-tricyclopropane.

The term "cycloalkylalkyl" means a cycloalkyl-alkyl-group in which the cycloalkyl and alkyl are as defined herein. Exemplary cycloalkylalkyl groups include cyclopropylmethyl and cyclopentylmethyl. The alkyl radical and the cycloalkyl radical may be optionally substituted as defined herein.

The term "aryl" means an aromatic monocyclic or multi-cyclic (polycyclic) ring system of 6 to about 19 carbon atoms, or of 6 to about 10 carbon atoms, and includes arylalkyl groups. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "heteroaryl" means an aromatic monocyclic or multi-cyclic ring system of about 5 to about 19 ring atoms, or about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Particular heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo

[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.aryl, According to one embodiment, $Z^1$ is a bond (e.g., peptide bond) between A and Q.

According to another embodiment, $Z^1$ is present and comprises —O—, —NH—, —NH-hydrocarbon-O— such as —NH—$C_{1-20}$ hydrocarbon-O—, —C(O)—, —C(S)—, —C(O)-hydrocarbon-C(O)— such as —C(O)—$C_{1-20}$ hydrocarbon-C(O)—, —C(O)—NH—, or —NH—C(O)—.

$Z^2$ can be any suitable linker molecule that forms a covalent bond with one of the groups on the steroid moiety as well as a covalent bond with the peptide or amino acid(s) that form Q. In certain embodiments, $Z^2$ is —O—, —NH—, —NH-hydrocarbon-O— such as —NH—$C_{1-20}$ hydrocarbon-O—, —C(O)—, —C(S)—, —C(O)-hydrocarbon-C(O)— such as —C(O)—$C_{1-20}$ hydrocarbon-C(O)—, —C(O)—NH—, or —NH—C(O)—.

D can be any suitable steroid moiety. As used herein, the steroid moiety is derived from a steroid compound insofar as one of the groups attached to the core steroid structure is used to link the steroid compound to Q (the peptide or amino acid) via linker $Z^2$.

Exemplary steroid moieties include, without limitation, a cholic acid moiety, a cholesterol moiety, a dexamethasone moiety, a lanosterol moiety, a beta-silosterol moiety, a testosterone moiety, a progesterone moiety, a medrogestone moiety, an aldosterone moiety, or a cortisol moiety.

According to one embodiment, the steroid moiety comprises a structure according to formula (II)

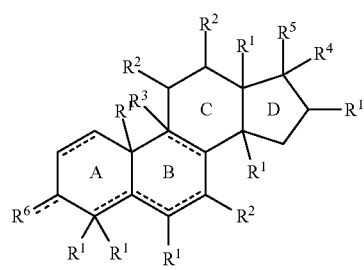

(II)

wherein one or both of rings A and B optionally includes a double bond at the site of the dash bonds, except that ring B does not contain more than one double bond;
each $R^1$ group is independently H or $CH_3$;
each $R^2$ group is independently selected from the group of H, OH, and —O-(bonded to $Z^2$);
$R^3$ is H or F;
$R^4$ is H, $CH_3$, OH, or —O-(bonded to $Z^2$);
$R^5$ is OH, —O-(bonded to $Z^2$), —C(O)—$CH_2$—OH, —C(O)—$CH_2$—O-(bonded to $Z^2$), —C(O)—$CH_3$, —CH($CH_3$)—O-(bonded to $Z^2$),

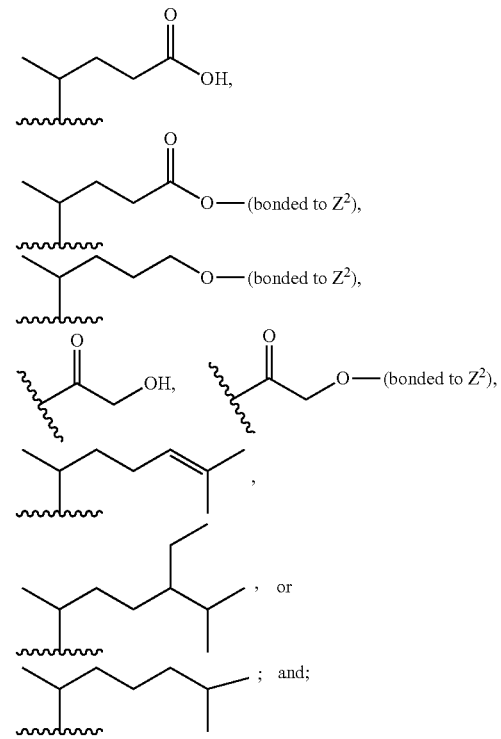

and
$R^6$ is OH, =O, or —O-(bonded to $Z^2$);
wherein one of the $R^2$, $R^4$, $R^5$, and $R^6$ groups is bonded to $Z^2$.

Other suitable steroids that can be presented in a conjugate according to formula (I) include, without limitation, methyl prednisolone, prednisone, betamethasone, clobetasol, diflucortolone, fluocinolone acetonide, cortisone, hydrocortisone, fludrocortisone, tixocortol, dihydrotachysterol, apoptone, oxandrolone, oxabolone, nandrolone, diethylstilbestrol (DES), beta estradiol, danazol, norethisterone, medroxyprogesterone acetate, 17-hydroxyprogesterone caproate, a deacylated product of difluprednate, beclomethasone, triamcinolone, alclometasone, mometasone, amcinonide, budesonide, desonide, fluocinonide, fluocinolone acetonide, halcinonide, derivatives of androstenediones and androstenediols, 7α-methyl hydroxy steroids of the type disclosed in U.S. Publ. No. 20100204497 and PCT Publ. No. 2003/059931.

In the accompanying Examples, the steroid moiety is covalently bonded to the linker, $Z^2$, at $R^6$, via —O-(bonded to $Z^2$) and $Z^2$ is —C(O)—.

According to one embodiment, Q is attached to $Z^1$ or A through an amino acid sidechain, for example, a lysine sidechain or arginine sidechain.

Exemplary conjugates according to formula (I) include, without limitation:

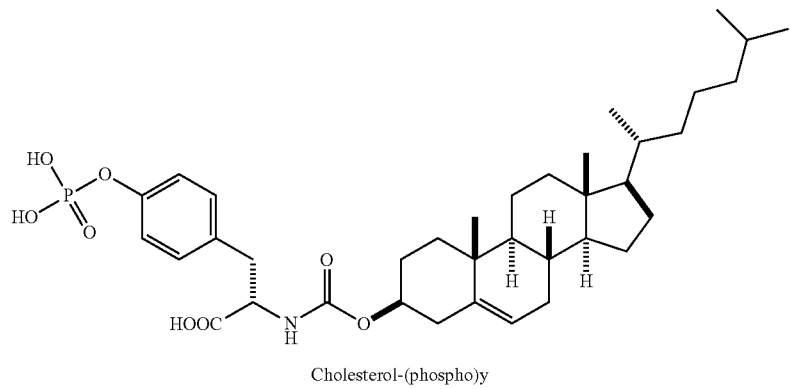
Cholesterol-(phospho)y
1a
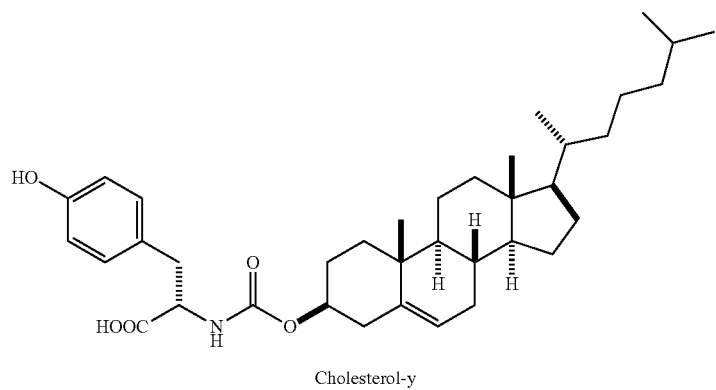
Cholesterol-y
1b
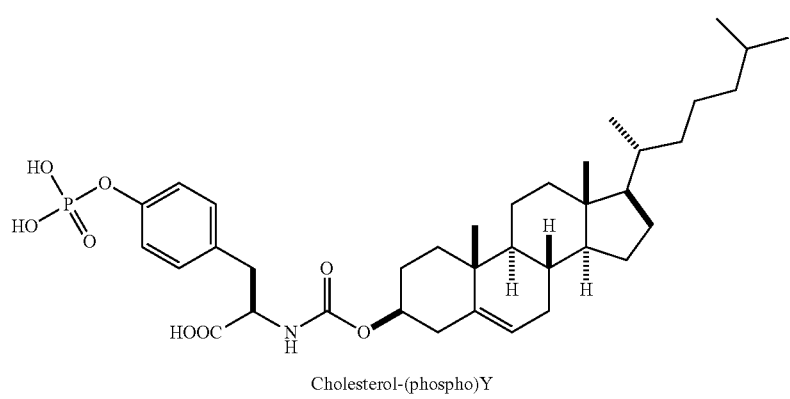
Cholesterol-(phospho)Y
2a -continued
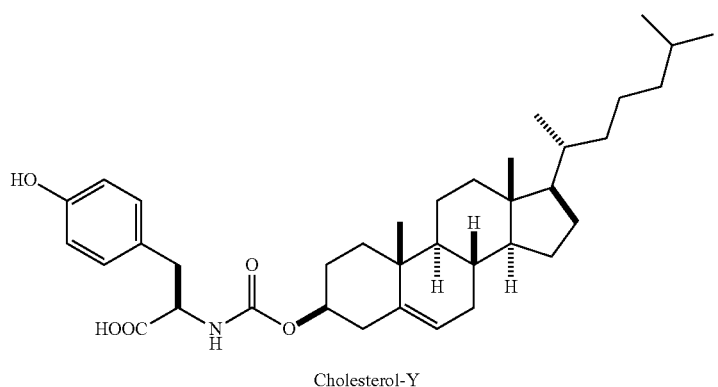
In each of the above compounds, D is a cholesteryl moiety, $Z^1$ is absent, $Z^2$ is a carbonyl, and Q is a single amino acid residue (D- or L-tyrosine, D- or L-(phospho)tyrosine, or D- or L-phenylalanine) with A being an OH group at the C-terminus of the amino acid residue.
Additional exemplary conjugates according to formula (I) include:
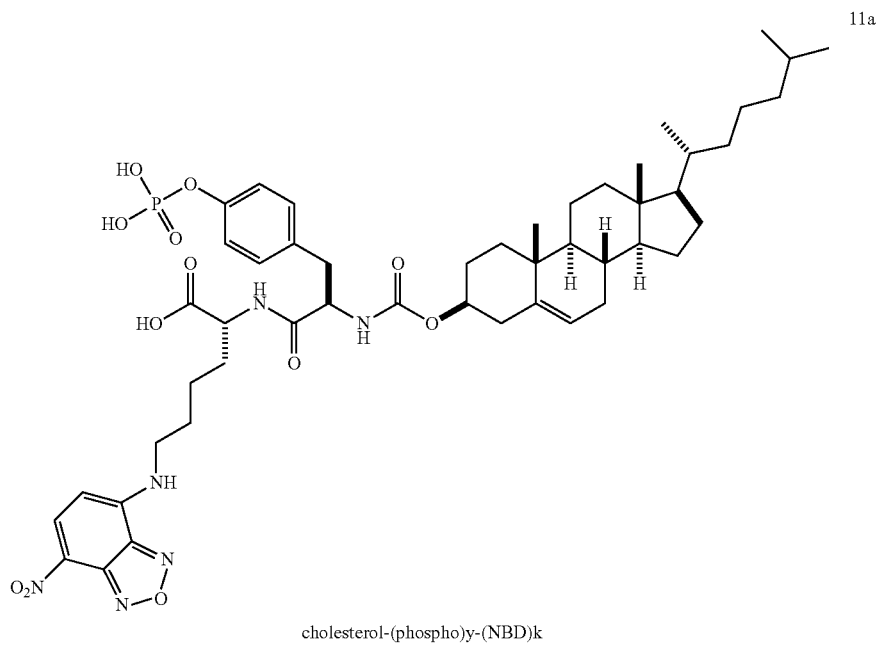

-continued
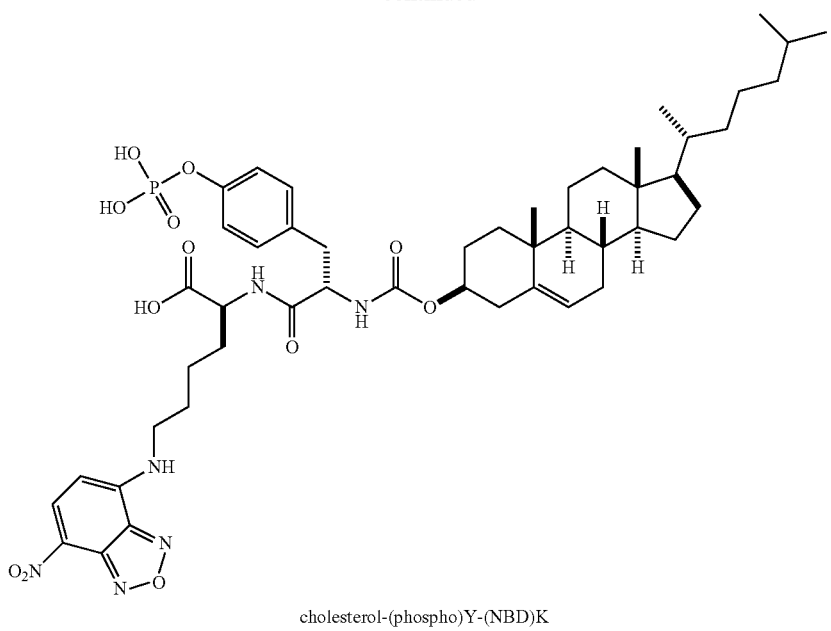
cholesterol-(phospho)Y-(NBD)K
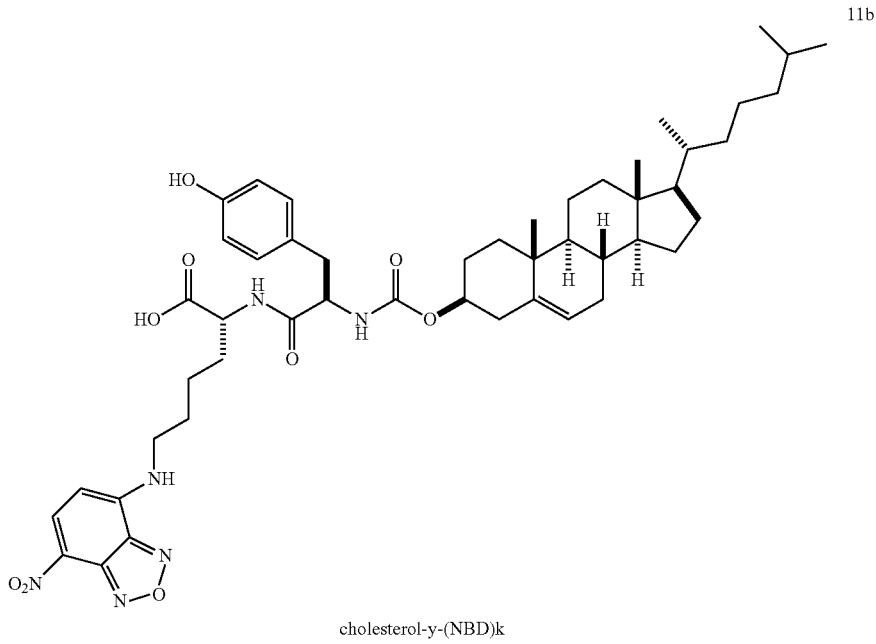
cholesterol-y-(NBD)k -continued

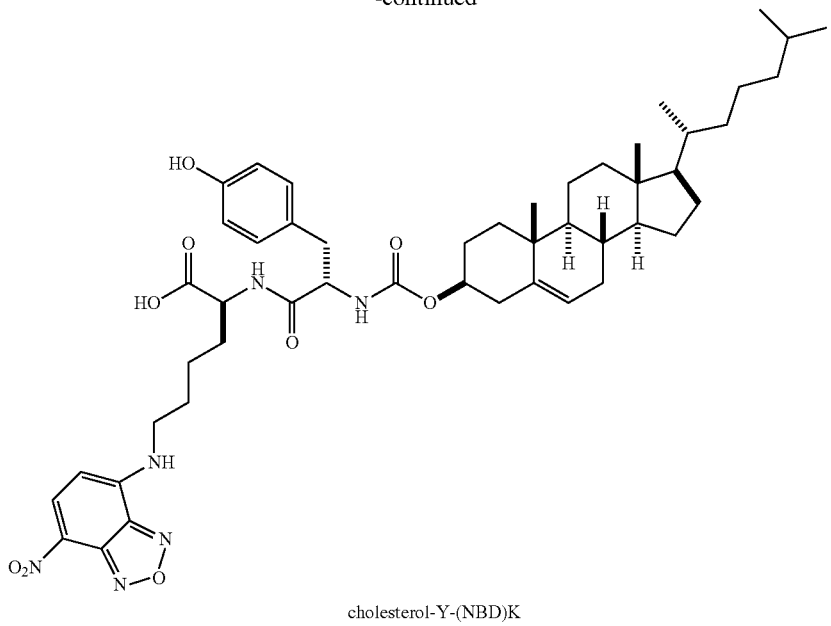

cholesterol-Y-(NBD)K

In each of the above compounds, D is a cholesteryl moiety, $Z^1$ is absent, $Z^2$ is a carbonyl, and Q is a dipeptide (containing D- or L-tyrosine or D- or L-(phospho)tyrosine, and D- or L-lysine containing a sidechain-linked fluorophore, 4-nitro-2,1,3-benzoxadiazole ("NBD"), with A being an OH group at the C-terminus of the amino acid residue.

Additional exemplary conjugates according to formula (I) include an antineoplastic agent of the type described in U.S. Pat. No. 9,408,921 to Gao et al., which is hereby incorporated by reference in its entirety. More specifically, the antineoplastic agents are coupled to the sidechain of an amino acid residue, and exemplary antineoplastic agents include paclitaxel, doxorubicin, daunorubicin, vinblastine, vincristine, cisplatin or 5-fluorouracil. Exemplary conjugates are shown below:

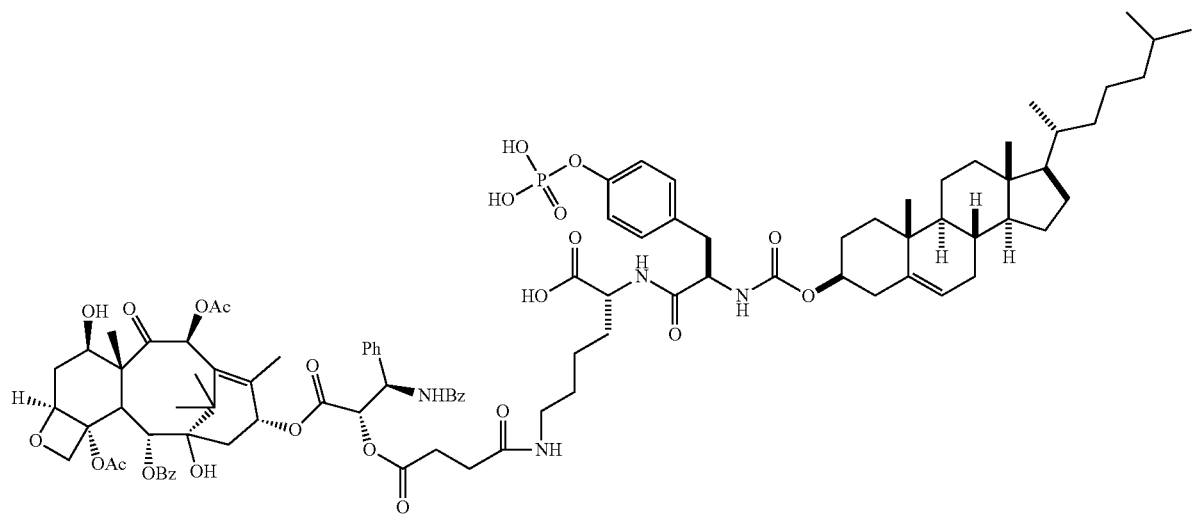

cholesterol-(phospho)y-(paclitaxel-succinyl)k

-continued
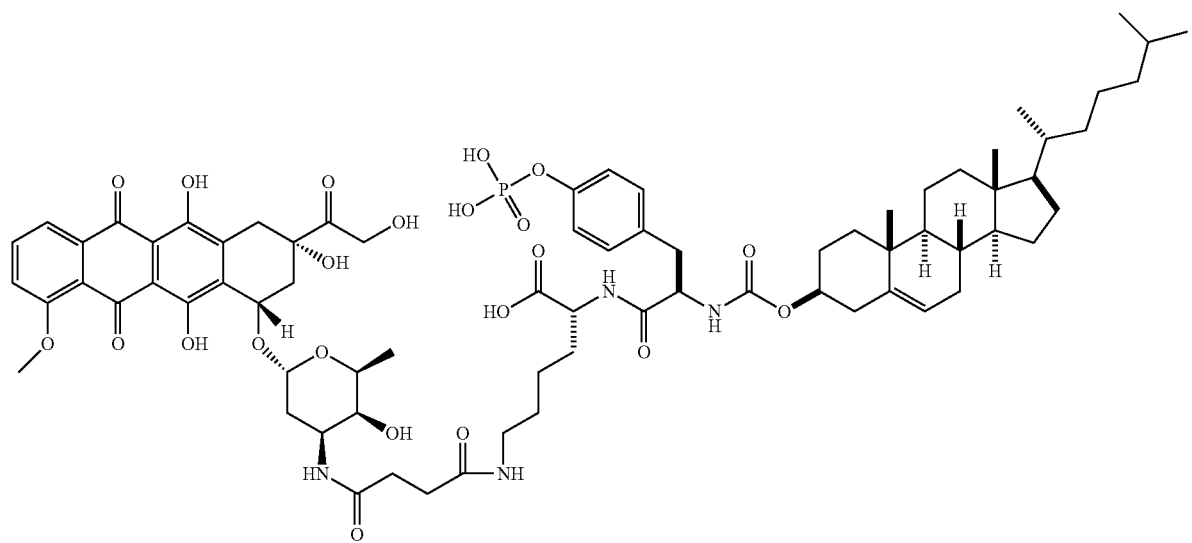
cholesterol-(phospho)y-(doxorubicin-succinyl)k
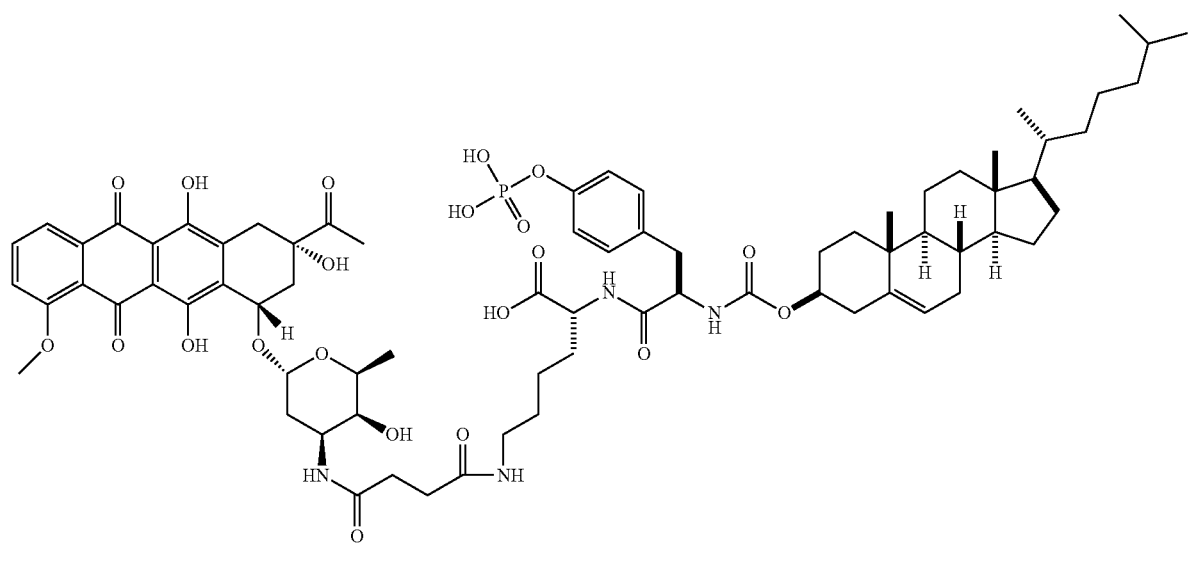
cholesterol-(phospho)y-(daunorubicin-succinyl)k

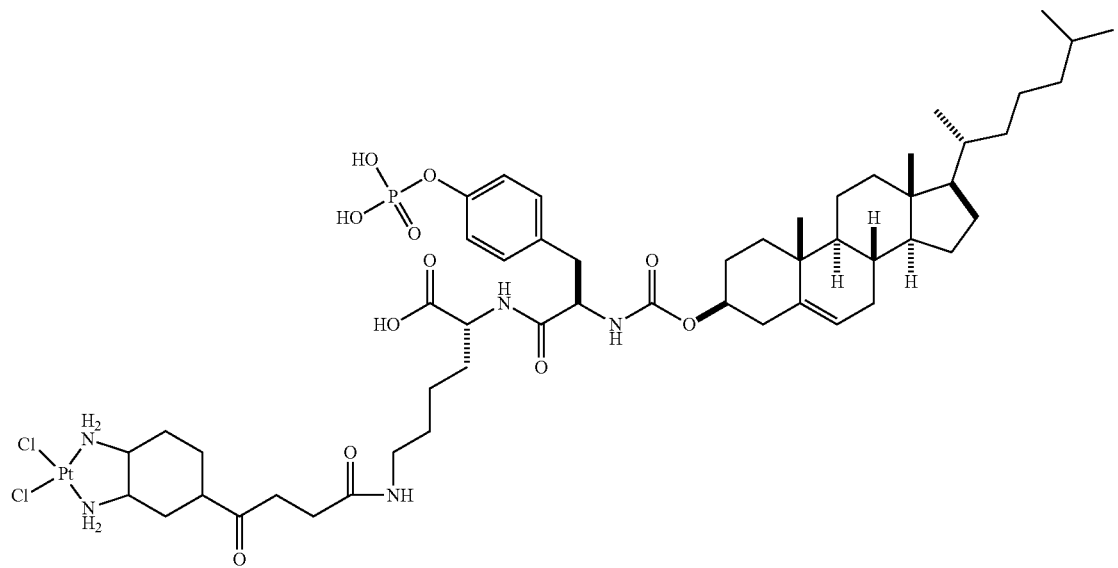
cholesterol-(phospho)y-(cisplatin prodrug-succinyl)k
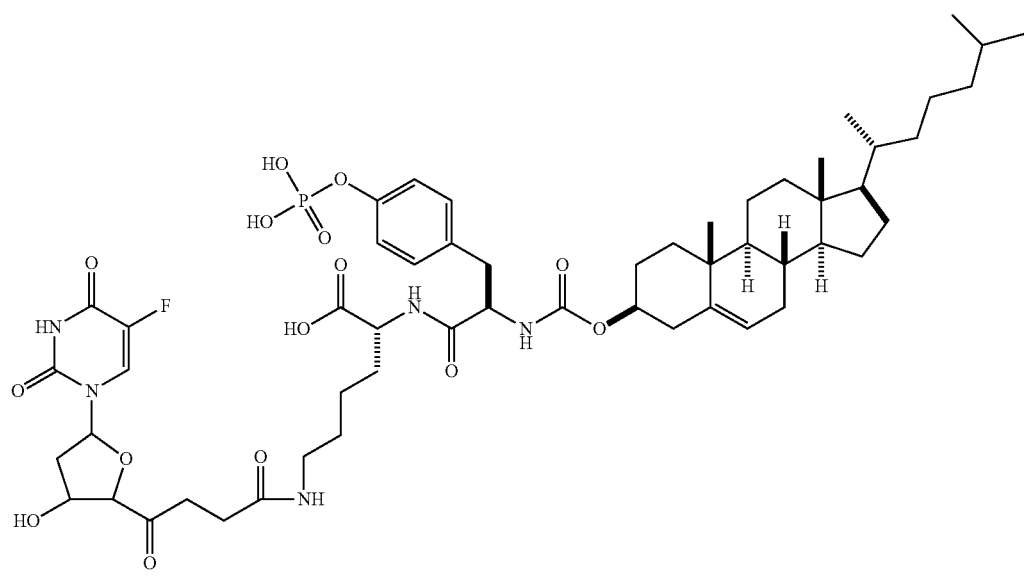
cholesterol-(phospho)y-(fluorouracil-4-hydroxy-3-succinyltetrahydrofuran-2-yl)k

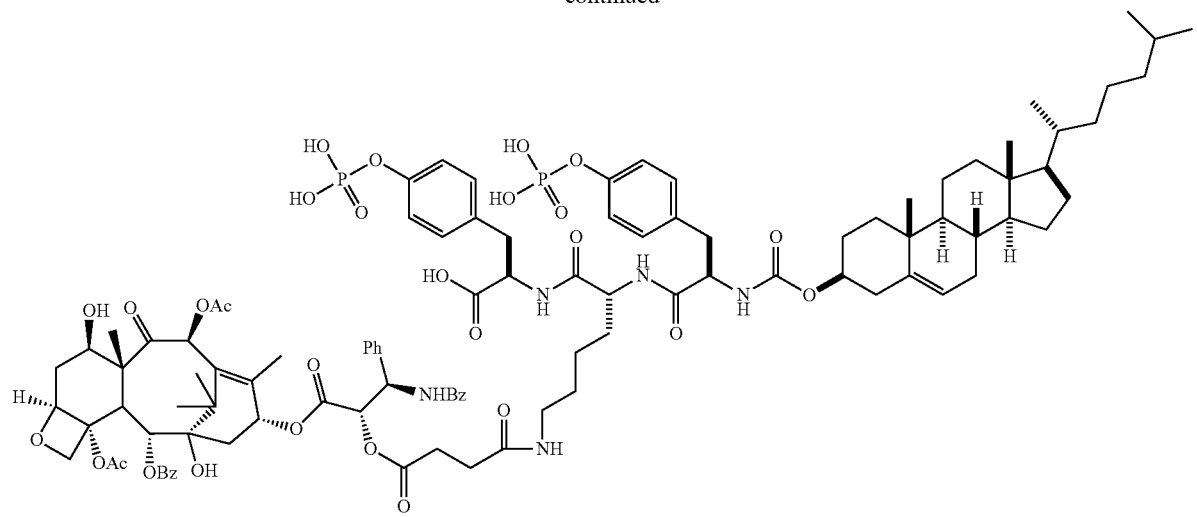
cholesterol-(phospho)y-(paclitaxel-succinyl)k-(phospho)y
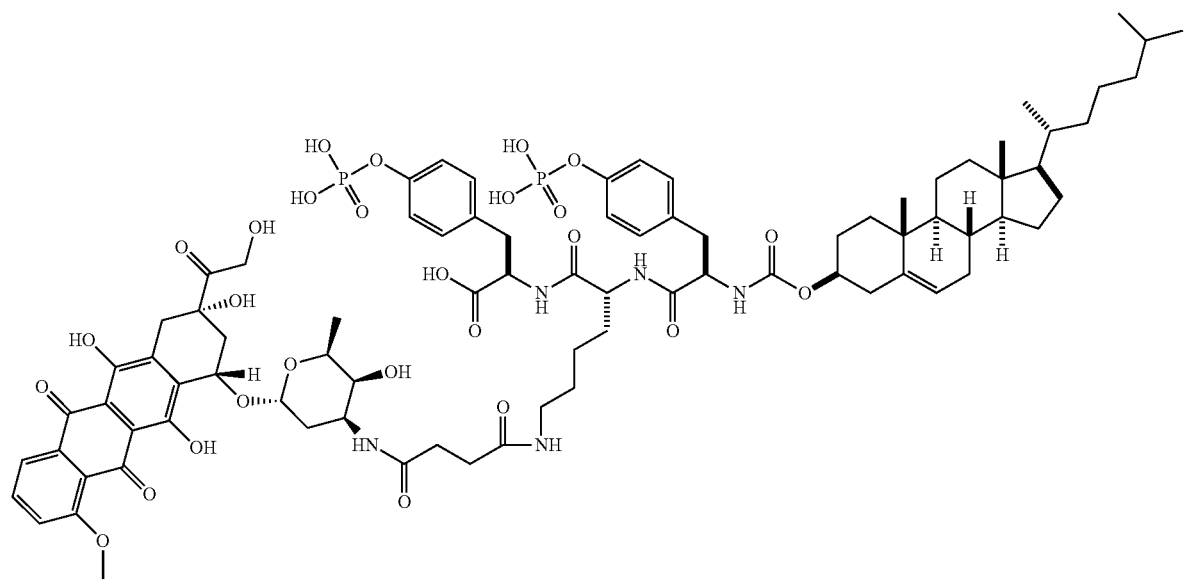
cholesterol-(phospho)y-(doxorubicin-succinyl)k-(phospho)y -continued
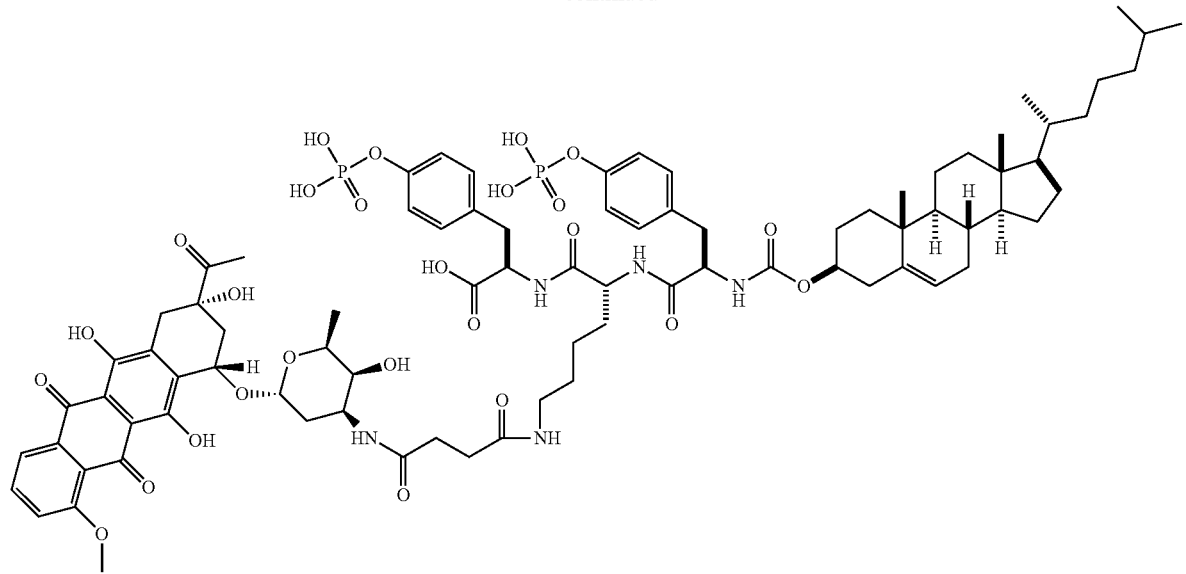
cholesterol-(phospho)y-(daunorubicin-succinyl)k-(phospho)y
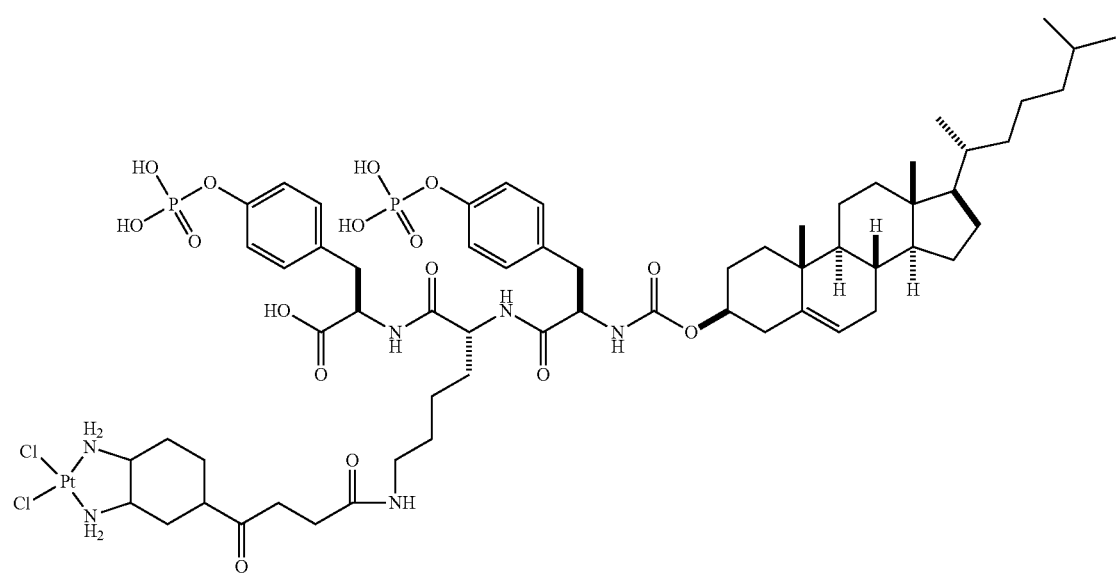
cholesterol-(phospho)y-(cisplatin prodrug-succinyl)k-(phospho)y

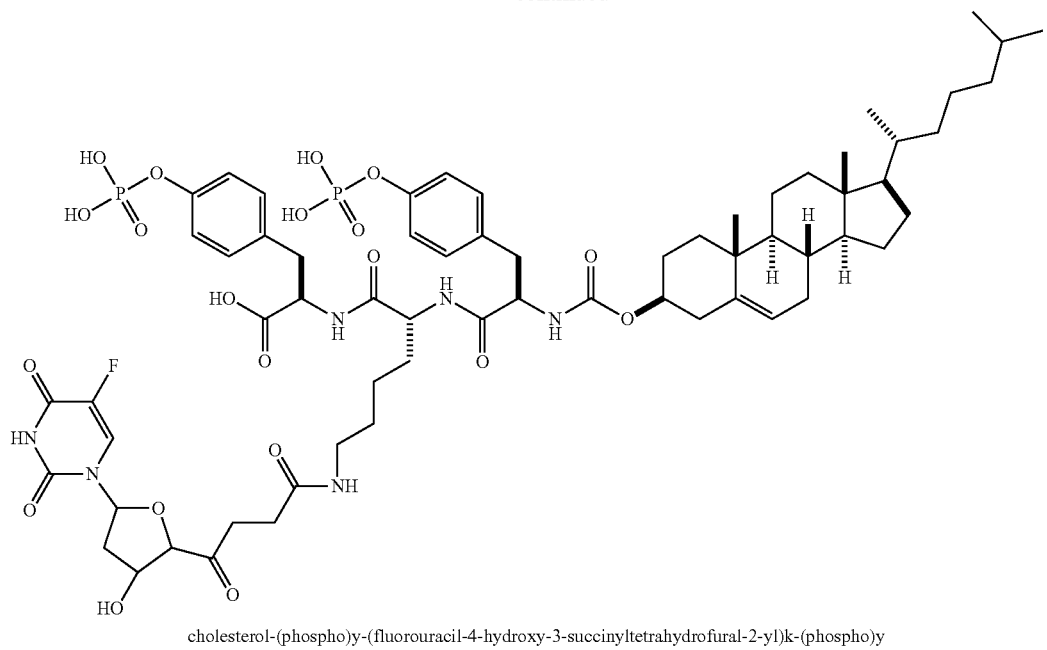
cholesterol-(phospho)y-(fluorouracil-4-hydroxy-3-succinyltetrahydrofural-2-yl)k-(phospho)y
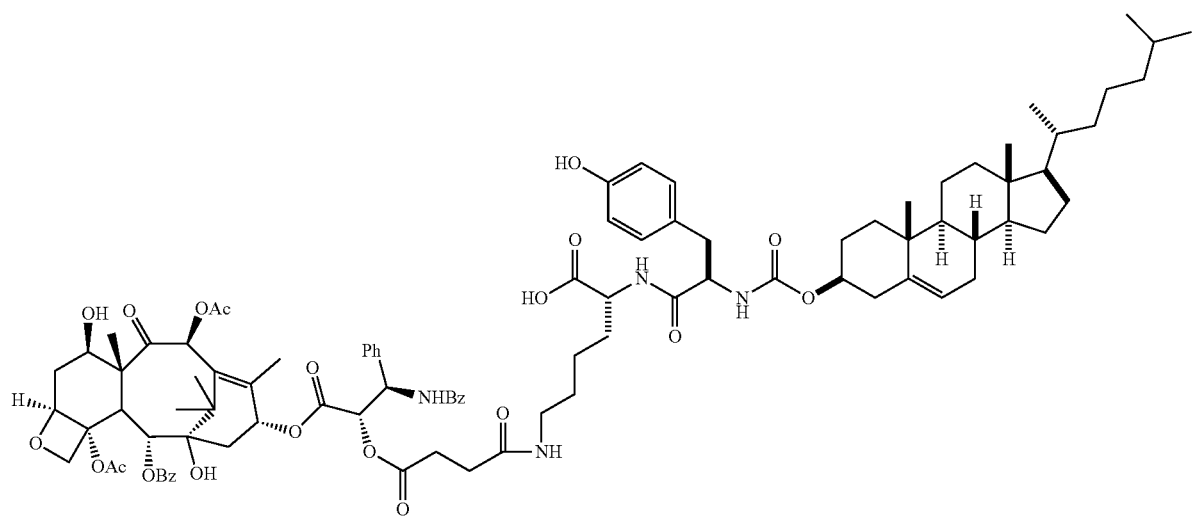
cholesterol-y-(paclitaxel-succinyl)k

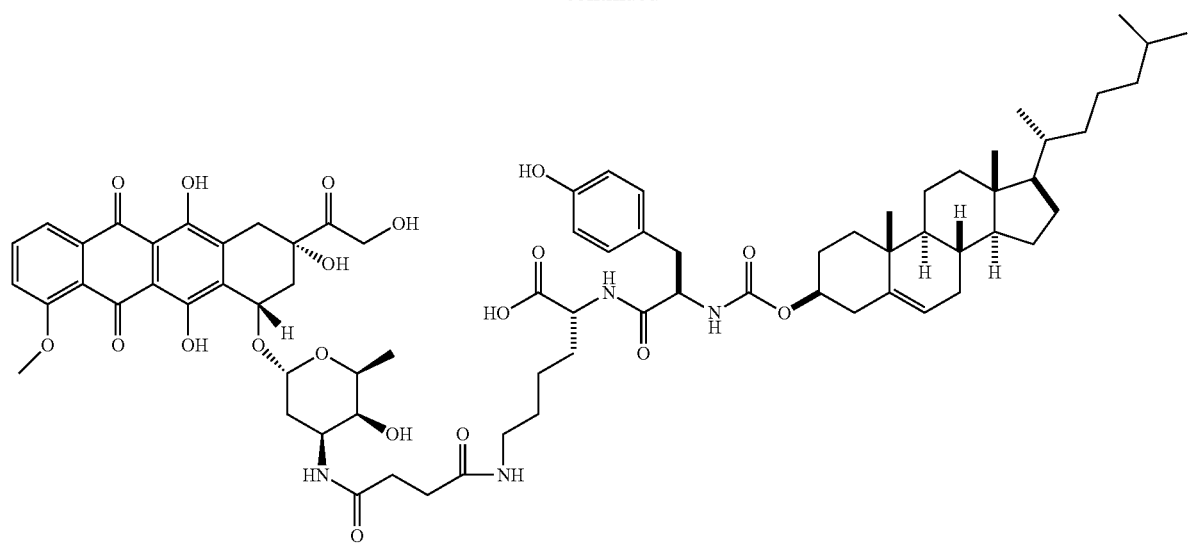
cholesterol-y-(doxorubicin-succinyl)k
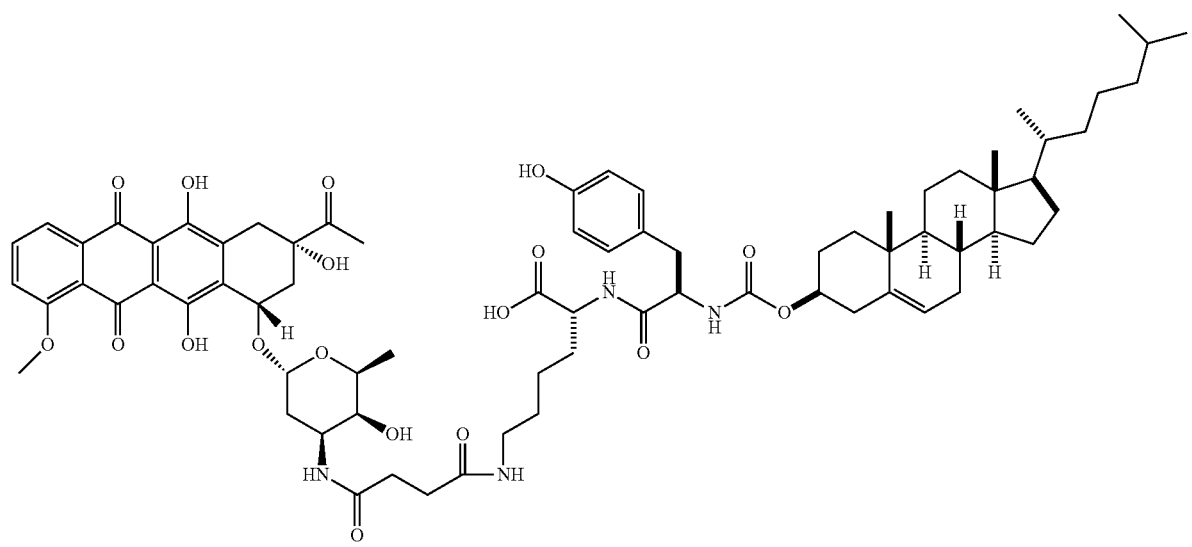
cholesterol-y-(daunorubicin-succinyl)k

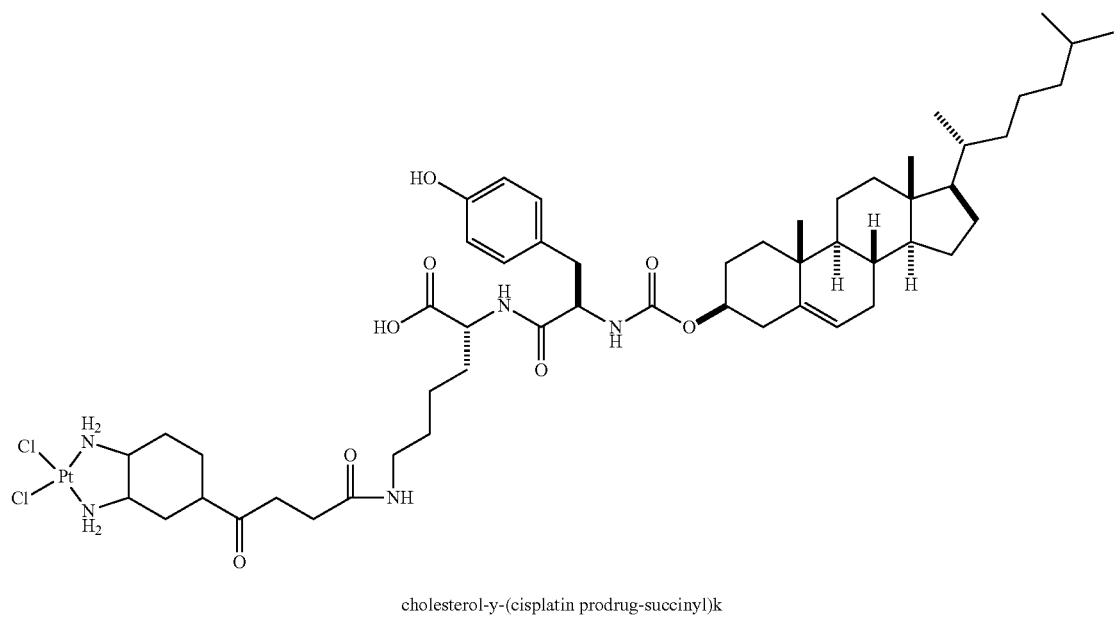
cholesterol-y-(cisplatin prodrug-succinyl)k
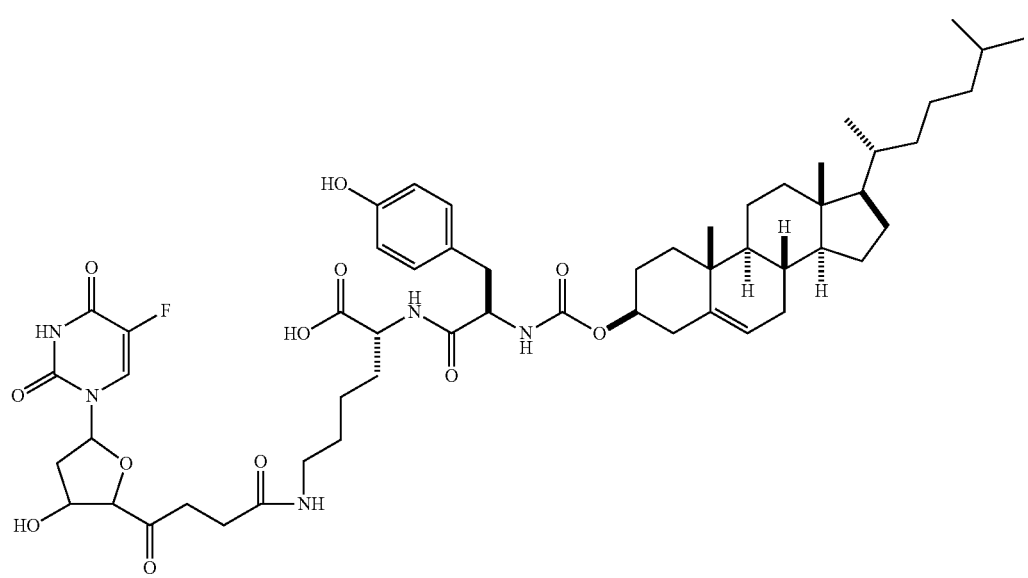
cholesterol-y-(fluorouracil-4-hydroxy-3-succinyltetrahydrofuran-2-yl)k

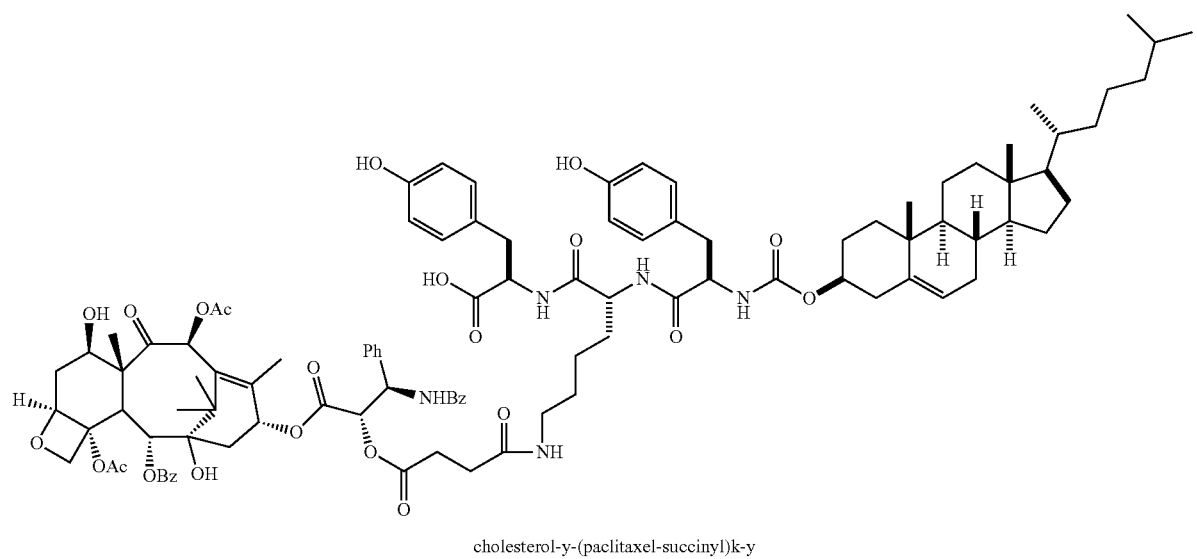
cholesterol-y-(paclitaxel-succinyl)k-y
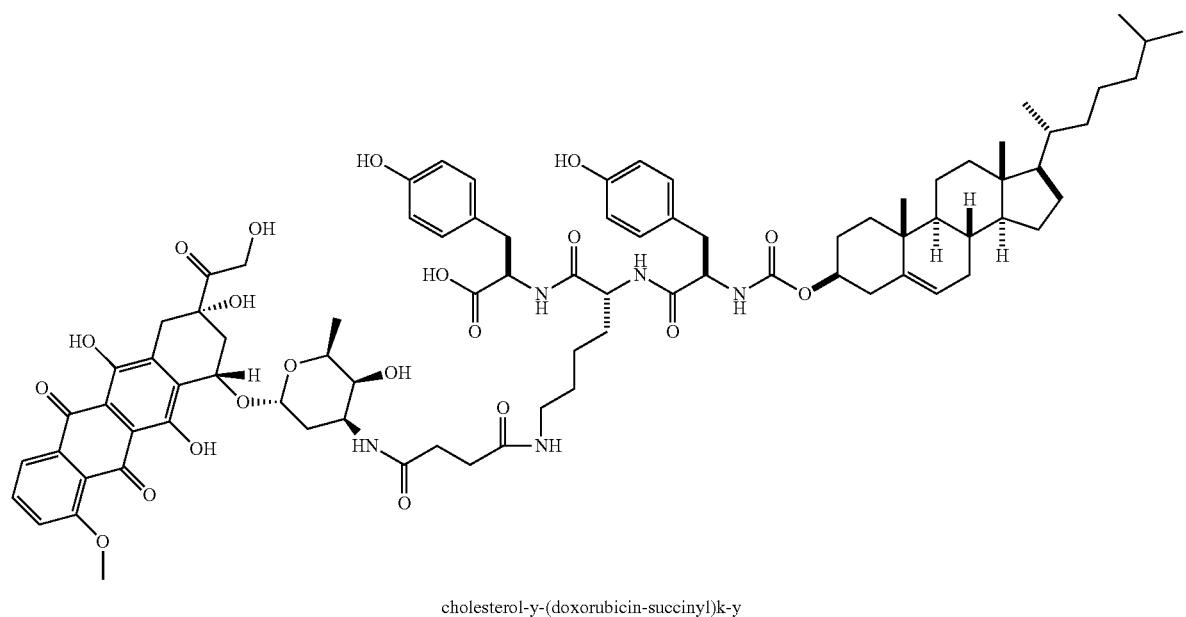
cholesterol-y-(doxorubicin-succinyl)k-y

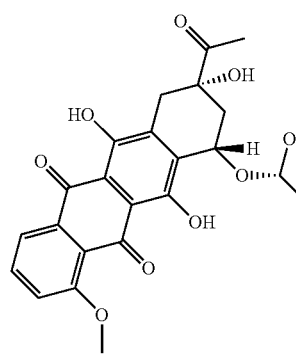
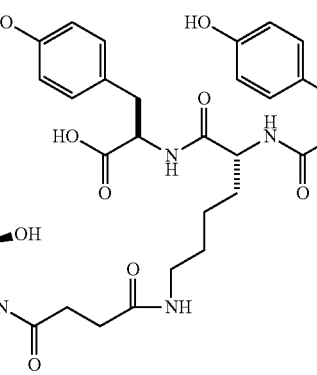
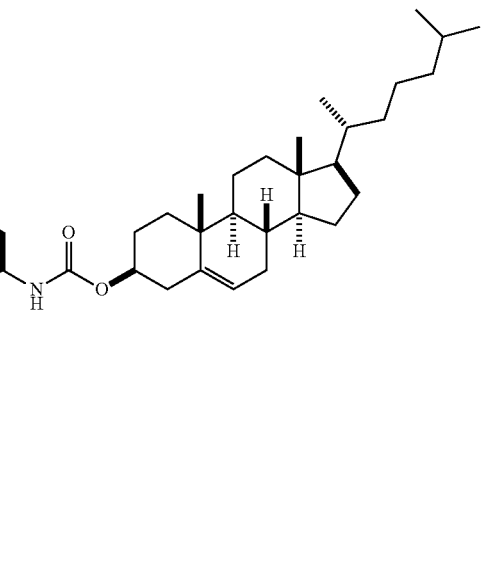
cholesterol-y-(daunorubicin-succinyl)k-y
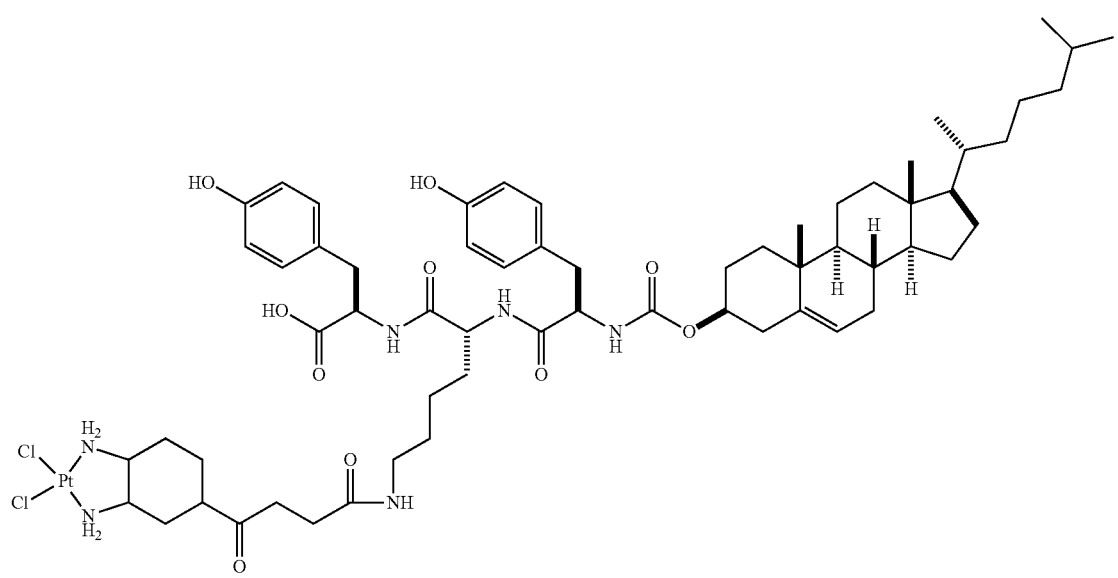
cholesterol-y-(cisplatin prodrug-succinyl)k-y -continued

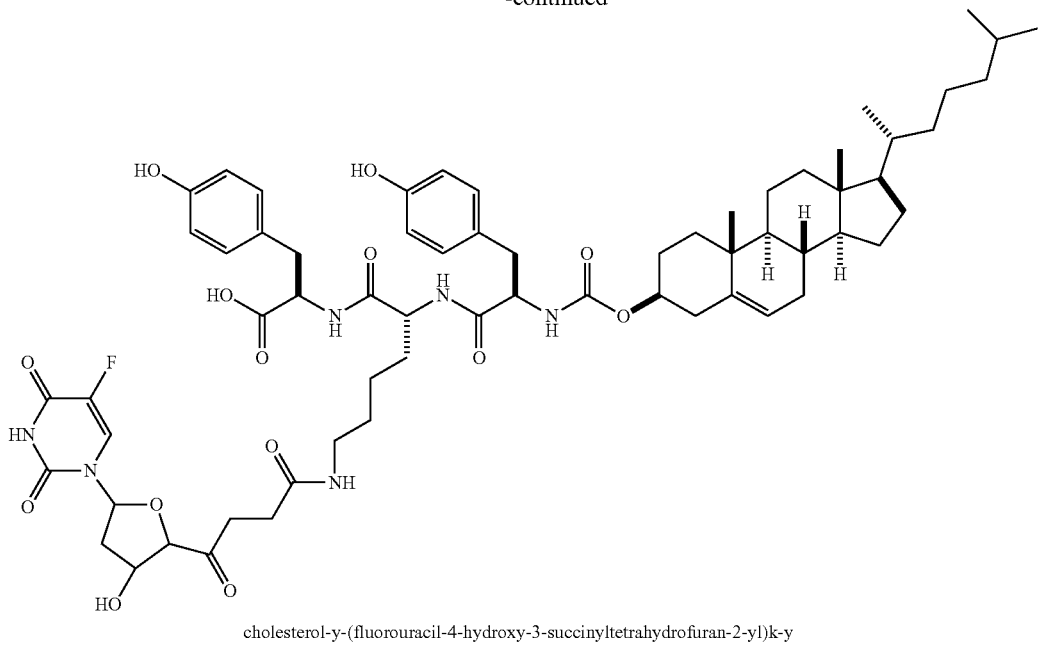

cholesterol-y-(fluorouracil-4-hydroxy-3-succinyltetrahydrofuran-2-yl)k-y

In each of the above compounds, D is a cholesteryl moiety, $Z^1$ is absent, $Z^2$ is a carbonyl, and Q is a dipeptide or tripeptide (containing D-tyrosine or D-(phospho)tyrosine, and D-lysine containing a sidechain-linked antineoplastic agent or prodrug linked via a succinyl group) with A being an OH group at the C-terminus of the amino acid residue. Variants of the above-identified compounds containing L-amino acids are also contemplated.

Additional exemplary conjugates according to formula (I) are shown below:

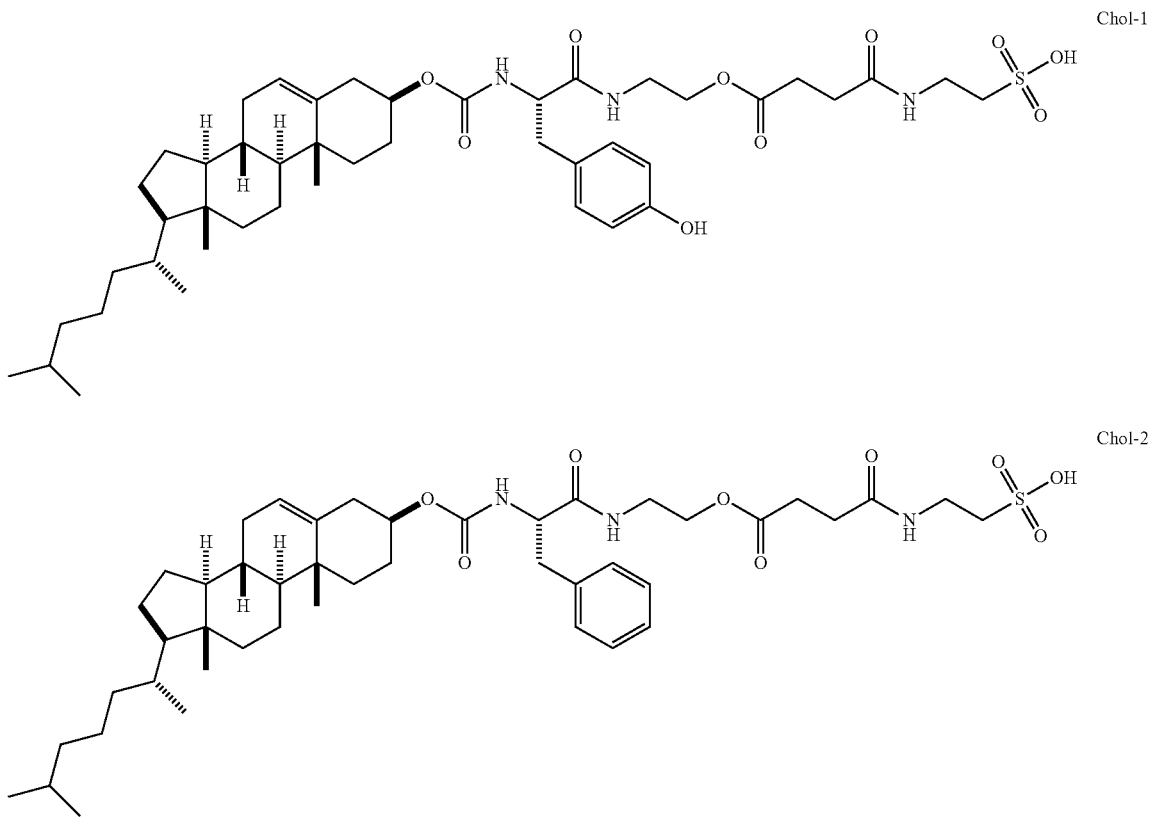

In each of Chol-1 and Chol-2, D is a cholesteryl moiety, $Z^2$ is a carbonyl, Q is an L-Phe or L-Tyr residue, and A includes an enzymatically cleavable moiety attached to the N-terminus of the amino acid residue. The enzymatically cleavable moiety also includes a taurine moiety. Together, A-$Z^1$— form the enzymatically cleavable moiety having the structure —N(H)—(CH$_2$)$_2$—O—C(O)—(CH$_2$)$_2$—C(O)—N(H)—(CH$_2$)$_2$—SO$_2$OH, where the ester bond is cleavable and the taurine moiety promotes cell uptake (see PCT Patent Application No. PCT/US16/19866 filed Feb. 26, 2016, which is hereby incorporated by reference in its entirety).

A further aspect of the invention relates to a method making a conjugate according to the present invention. Any of a variety of techniques can be used to conjugate the steroid moiety to the amino acid(s) present in the conjugate, as Q, via suitable linker molecules.

According to one embodiment, this method includes providing a first intermediate compound having the structure:

$$LG^1\text{-}Z^2\text{-}D \qquad (III),$$

wherein $Z^2$ and D are defined, as above, and $LG^1$ is a leaving group; and then forming the drug conjugate of formula (I) from the first intermediate compound. This first intermediate compound is commercially available (e.g., cholesteryl chloroformate, 5α-androstan-17β-ol-3-one chloroformate) or can readily be synthesized (Humphlett et al., *J. Org. Chem.* 26:2511 (1961), which is hereby incorporated by reference in its entirety). This step can be carried out by reacting the first intermediate compound with a compound having the structure:

$$(A\text{-}Z^1\text{-})_n\text{-}Q\text{-}R^{10} \qquad (IV),$$

wherein A, $Z^1$, Q, and n are defined as above, and $R^{10}$ is H or a leaving group.

According to another embodiment, the process further includes: providing a second intermediate compound of formula (V)

$$H\text{-}D \qquad (V)$$

and forming the first intermediate compound from the second intermediate compound. The step of forming the first intermediate compound comprises reacting the second intermediate compound with a compound having the structure:

$$LG^1\text{-}Z^2\text{-}LG^2 \qquad (VI),$$

wherein $Z^2$ and $LG^1$ are defined above, and $LG^2$ is a leaving group, wherein said reacting is carried out under conditions effective to produce the first intermediate compound of formula (III).

The peptide sequence, Q, can be synthesized using standard peptide synthesis operations. These include both FMOC (9-Fluorenylmethyloxy-carbonyl) and tBoc (tert-Butyl oxy carbonyl) synthesis protocols that can be carried out on automated solid phase peptide synthesis instruments including, without limitation, the Applied Biosystems 431A, 433A synthesizers and Peptide Technologies Symphony or large scale Sonata or CEM Liberty automated solid phase peptide synthesizers. Sidechain modification, of the type describe above for coupling to a lysine or arginine sidechain, can be carried out using the protected peptide prior to purification. Once synthesis is complete, this can be followed with standard HPLC purification to achieve a purified peptide product.

The present invention also encompasses the formation of nanoparticle aggregates (or assemblies), which are self-assembled forms of the described conjugates. These nanoparticle aggregates may have random shapes and configurations, but are distinguishable from longer filamentous structures (defined below). As used herein, the nanoparticle aggregates encompasses particles that are within the nanoscale regime, but preferably particles on the order of about 100 nanometers or less. The term "nano-assembly" is intended to encompass nanoparticle aggregates, as well as membrane-bound lipid rafts that may be formed by conjugates of the present invention. As noted supra, in certain embodiments the conjugates of the present invention may be enzymatically activated by one or more of the following: hydrolytic cleavage of the enzymatically cleavable-moiety present at A, dephosphorylation of one or more phosphorylated amino acids present at Q, desulfation of one or more sulfated amino acids present at Q, or a combination thereof. The nanoparticle aggregates may also comprise a separate therapeutic agent (e.g., chemotherapeutic agent, immunotherapeutic agent, or other small molecule, antineoplastic agent) that is loaded into the aggregates as they form. These aggregates can be separately used to contact cancer cells and release the therapeutic agent to induce cancer cell death.

The present invention also encompasses the formation of hydrogels and nanoparticle aggregates (or assemblies) by conjugates of the present invention as well as enzymatically activated forms thereof. As noted supra, in certain embodiments the conjugates of the present invention may be enzymatically activated by one or more of the following: hydrolytic cleavage of the enzymatically cleavable-moiety present at A, dephosphorylation of one or more phosphorylated amino acids present at Q, desulfation of one or more sulfated amino acids present at Q, or a combination thereof.

A hydrogel may be defined as a three-dimensional, hydrophilic or amphiphilic network capable of taking up a quantity of water, typically a large quantity of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water that allows them to swell in aqueous media. The chains of the network are connected in such a fashion that pores exist and that a substantial fraction of these pores are of dimensions between 1 nm and 1000 nm. As used herein and is well-known in the art, the term "hydrogel" refers to a material that comprises fibrous networks formed of water-soluble natural or synthetic polymer chains, typically (though not exclusively) containing more than 95% water, often more than 96%, 97%, 98%, or 99% water.

A "fibrous network" refers to a set of connections formed between the plurality of fibrous components. Herein, the fibrous components are composed of conjugates according to formula (I), or enzymatically activated forms thereof as described above. Such fibrils are formed upon self-assembly of the conjugated or their enzymatically activated forms. The peptide can be present alone within the fibrous network, in the form of a conjugate as described above which is incorporated into the fibrous network, or a combination thereof. The fibrous network can be formed in an ex vivo environment, or alternatively in vivo. When formed in vivo, the fibrous network may in certain embodiments form externally of a cell, such as a cell that expresses one or more ectoenzymes that activate the conjugate of the present invention. Alternatively, the fibrous network may in certain embodiments form internally of a cell, such as a cell that expresses endoenzymes that activate the conjugate of the present invention.

The terms "gelling" and "gelation" means a thickening of the medium that may result in a gelatinous consistency and even in a solid, rigid consistency that does not flow under its own weight.

A "gelator" is defined herein to include a non-polymeric conjugate according to formula (I) whose molecules can establish, between themselves, at least one physical interaction leading to a self-assembly of the molecules in a carrier fluid to form a gel. The gel may result from the formation of a network of molecular nanofibers, aggregates, or both, due to the stacking or aggregation of gelator molecules.

A "molecular nanofiber" is defined as a fiber with a diameter on the order of about 100 nanometers or less. The fibrous network can include nanofibers as well as fibers that have larger diameters. In certain embodiments, the hydrogel can contain a large majority of self-assembled, nanofibers, from about 60% or more, about 70% or more, about 80% or more, and even about 90% or more. In alternative embodiments, the hydrogel can contain a minority of such self-assembled nanofibers, although larger fibers can be present.

Thus, a further aspect of the invention relates to a pharmaceutical composition including a pharmaceutically acceptable carrier and a conjugate of the present invention, which is present in an effective amount, preferably in a purified form.

In certain embodiments, more than one conjugate can be provided.

The conjugates can be similar in structure, but possess different conjugated agents as described above. In alternative embodiments, the conjugates can be structurally distinct, including different structures that are nevertheless capable of self-assembly due to the structural compatibility of the aromatic amino acid residues in the different conjugates.

By way of example, a conjugate of the present invention lacking a conjugated chemotherapeutic agent can be combined with another conjugate of the present invention that possesses a conjugated chemotherapeutic agent of the type described above. These can be provided in various ratios so as to facilitate an appropriate dosage of the self-assembling conjugates while also achieving a desired dose of the conjugated chemotherapeutic agent.

In addition to the foregoing, the conjugates of the present invention can be mixed with other self-assembling, or enzymatically-induced self-assembling conjugates of the type described in the prior art (e.g., PCT Application Publ. No. WO/2015/157535, PCT Application Publ. No. WO/2015/116242, PCT Application Publ. No. WO/2014/138367, PCT Application Publ. No. WO/2014/074789, PCT Application Publ. No. WO/2012/166706, PCT Application Publ. No. WO/2012/166705, PCT Application Publ. No. WO/2010/151644) to co-form nanoparticles, nanofibers, hydrogel matrices, and networks containing the same.

In certain embodiments, the carrier is an aqueous medium that is well tolerated for administration to an individual, typically a sterile isotonic aqueous buffer. Exemplary aqueous media include, without limitation, normal saline (about 0.9% NaCl), phosphate buffered saline (PBS), sterile water/distilled autoclaved water (DAW), as well as cell growth medium (e.g., MEM, with or without serum), aqueous solutions of dimethyl sulfoxide (DMSO), polyethylene glycol (PEG), and/or dextran (less than 6% per by weight.)

To improve patient tolerance to administration, the pharmaceutical composition preferably has a pH of about 6 to about 8, preferably about 6.5 to about 7.4. Typically, sodium hydroxide and hydrochloric acid are added as necessary to adjust the pH.

The pharmaceutical composition suitably includes a weak acid or salt as a buffering agent to maintain pH. Citric acid has the ability to chelate divalent cations and can thus also prevent oxidation, thereby serving two functions as both a buffering agent and an antioxidant stabilizing agent. Citric acid is typically used in the form of a sodium salt, typically 10-500 mM. Other weak acids or their salts can also be used.

The composition may also include solubilizing agents, preservatives, stabilizers, emulsifiers, and the like. A local anesthetic (e.g., lidocaine) may also be included in the compositions, particularly for injectable forms, to ease pain at the site of the injection.

Effective amounts of the conjugates will depend on the nature of use, including the nature of the cancerous condition which is being treated, tumor volume and stage, and its location(s). By way of example only, suitable conjugates concentrations may range from about 0.1 µM to about 10 mM, preferably about 1 µM to about 5 mM, about 10 µM to about 2 mM, or about 50 µM to about 1 mM. The volume of the composition administered, and thus, dosage of the conjugates administered can be adjusted by one of skill in the art to achieve optimized results. In one embodiment, between 100 and about 800 µg can be administered per day, repeated daily or periodically (e.g., once every other day, once every third day, once weekly). This can be adjusted lower to identify the minimal effective dose, or tailored higher or lower according to the nature of the tumor to be treated.

In certain embodiments, the pharmaceutical composition can include, in addition to the conjugate, one or more additional therapeutic agents. These additional therapeutic agents can include, without limitation, chemotherapeutic agents (including alkylating agents, platinum drugs, antimetabolites, anthracycline and non-anthracycline antitumor antibiotics, topoisomerase inhibitors, and mitotic inhibitors), corticosteroids and targeted cancer therapies (such as imatinib (Gleevec®), gefitinib (Iressa®), sunitinib (Sutent®) and bortezomib (Velcade®)), antiangiogenic agents, antineoplastic agents, immunotherapeutic agents, and radiotherapeutic agents. These agents can be administered using conventional dosages or, alternatively, given the demonstrated non-additive effects of co-administering a chemotherapeutic agent with a peptide of the present invention, it is also contemplated that effective doses of these additional therapeutic agents can be further reduced (so as to minimize side effects) while also improving or maintaining the efficacy of the combination therapy as compared to the efficacy of the therapeutic agent alone.

In certain embodiments, the pharmaceutical composition contains nanoparticle aggregates of the disclosed conjugates, optionally in combination with one or more of the therapeutic agents described in the preceding paragraph.

Also contemplated herein are therapeutic systems that include, as separate compositions, a first composition containing a conjugates of the present invention in a suitable carrier, and a second composition containing an effective amount of one of the aforementioned additional therapeutic agents in a suitable carrier. These separate compositions can be co-administered according to a therapeutic protocol and dosing schedule.

A further aspect of the invention relates to a method for treating a cancerous condition. This method includes administering to a subject having a cancerous condition a therapeutically effective amount of the conjugate or pharmaceutical composition as described above, wherein said administering is effective to cause intracellular or pericellular self-assembly, or both intracellular and pericellular self-assembly, of the conjugate upon enzymatic cleavage of the enzymatically cleavable-moiety, enzymatic dephosphorylation of the phosphorylated amino acid, or enzymatic desulfation of the sulfated amino acid.

According to one embodiment, the cancer cells express an esterase having hydrolytic activity. In one embodiment, the esterase is an endoesterase. In another embodiment, the esterase is an ectoesterase.

According to another embodiment, the cancer cells express a phosphorylase. In one embodiment, the phosphorylase is an endophosphorylase. In another embodiment, the phosphorylase is an ectophosphorylase.

According to another embodiment, the cancer cells express a sulfatase. In one embodiment, the sulfatase is an endosulfatase. In another embodiment, the sulfatase is an ectosulfatase.

A related aspect of the invention relates to a method for treating a cancerous condition. This method includes administering to a subject having a cancerous condition a therapeutically effective amount of the nanoparticle aggregates comprising one or more conjugates as described herein optionally in combination with a therapeutic agent, or a pharmaceutical composition containing the nanoparticle aggregates, wherein said administering is effective to cause cancer cell death. In this embodiment, the nanoparticle aggregates are formed ex vivo and then administered to a subject, and in the presence of a therapeutic agent such conjugates will release the therapeutic agent intracellularly or extracellularly to affect cancer cell survival.

Yet another aspect of the invention relates to a method for forming a network on or near the surface of target cells. This method includes contacting a target cell that expresses a cell surface-bound enzyme having hydrolytic activity or phosphorylase or sulfatase activity, secretes an enzyme having hydrolytic activity or phosphorylase or sulfatase activity, or both, with the conjugate according to the first aspect or the pharmaceutical composition according to the second aspect, wherein said contacting is effective to hydrolyze an enzymatically cleavable moiety, dephosphorylate a phosphorylated amino acid, or desulfate a sulfated amino acid and thereby cause in situ self-assembly of the conjugate to form a network on or near the inner or outer surface, or both the inner and outer surfaces, of the target cell. According to one embodiment the network is nanofibril network.

This aspect of the invention may also be carried out in a manner whereby self-assembly of the enzymatically activated conjugate occurs inside the same target cell, in which case nanofibril network assembly occurs both internally and externally of the target cell.

As a consequence of forming the nanofibril network internally or externally of the cell surface (or both), one or more of the following occurs: cell migration is inhibited, cell survival is inhibited, and/or cell growth and division is inhibited. Overall, cellular processes are disrupted, and cell viability is reduced. Where a cytotoxic drug is conjugated to the conjugate or aggregated into a thus-formed network, drug release from the conjugate (or network) allows for enhanced cytotoxicity. The cell can be ex vivo or in vivo (in accordance with the method of treatment described below).

A related aspect of the invention relates to the treatment of a patient for cancer. This method involves administering to a subject having a cancerous condition a therapeutically effective amount of the conjugate of the present invention or the pharmaceutical composition of the present invention, wherein the administering is effective to cause cell uptake of the conjugate followed by enzymatic cleavage of the peptide from taurine/hypotaurine (predominantly in cancer cells), and then in vivo self-assembly of the conjugate to form a nanofibril network within the cancer cells expressing an endoenzyme having enzymatic activity suitable to cleave the enzymatically-cleavable moiety. Such self-assembly has the effects noted above, and in the presence of a conjugated cytotoxic agent, intracellular or extracellular release of that cytotoxic agent is also afforded.

In the several methods of use described herein, exemplary subjects include any mammal that is susceptible to cancerous conditions including, without limitation, rodents, rabbits, canines, felines, ruminants, and primates such as monkeys, apes, and humans.

Administration of the conjugate or pharmaceutical composition can be carried out using any suitable approach. By way of example, administration can be carried out parenterally, subcutaneously, intravenously, intradermally, intramuscularly, intraperitoneally, by implantation, by intracavitary or intravesical instillation, intraarterially, intralesionally, intradermally, peritumorally, intratumorally, or by introduction into one or more lymph nodes. In certain embodiments, administration is carried out intralesionally, intratumorally, intradermally, or peritumorally.

In these several aspects of the invention, the cancer cells express an endoenzyme. In these embodiments, the enzyme produced by the cancer cells is an endoenzyme having hydrolytic activity, i.e., the enzyme hydrolyzes a phosphate group, or an ester group, carbonate group, thiocarbonate group, carbamate group, carboxylate group, or diacyl anhydride group that is present within an enzymatically cleavable moiety. The effect of such cleavage is liberation of the phosphate group or, e.g., the (hypo)taurine residue, which then affords hydrogelation or aggregation of the conjugates internally of the cancer cells expressing the endoenzyme.

The cancer cells to be treated in accordance with these aspects can be present in a solid tumor, present as a metastatic cell, or present in a heterogenous population of cells that includes both cancerous and noncancerous cells. Exemplary cancer conditions include, without limitation, cancers or neoplastic disorders of the brain and CNS (glioma, malignant glioma, glioblastoma, astrocytoma, multiforme astrocytic gliomas, medulloblastoma, craniopharyngioma, ependymoma, pinealoma, hemangioblastoma, acoustic neuroma, oligodendroglioma, meningioma), pituitary gland, breast (Infiltrating, Pre-invasive, inflammatory cancers, Paget's Disease, Metastatic and Recurrent Breast Cancer), blood (Hodgkin's Disease, Leukemia, Multiple Myeloma, Lymphoma), lymph node cancer, lung (Adenocarcinoma, Oat Cell, Non-small Cell, Small Cell, Squamous Cell, Mesothelioma), skin (melanoma, basal cell, squamous cell, Kapsosi's Sarcoma), bone cancer (Ewing's Sarcoma, Osteosarcoma, Chondrosarcoma), head and neck (laryngeal, pharyngeal, and esophageal cancers), oral (jaw, salivary gland, throat, thyroid, tongue, and tonsil cancers), eye, gynecological (Cervical, Endometrial, Fallopian, Ovarian, Uterine, Vaginal, and Vulvar), genitourinary (Adrenal, bladder, kidney, penile, prostate, testicular, and urinary cancers), and gastrointestinal (appendix, bile duct (extrahepatic bile duct), colon, gallbladder, gastric, intestinal, liver, pancreatic, rectal, and stomach cancers).

Use of the conjugate and pharmaceutical compositions can be coordinated with previously known therapies. For instance, where the conjugate is conjugated with a thermoablative nanoparticle, after formation of the pericellular nanofibril network, a tumor-containing region of the subject's body can be exposed to near infrared light, thereby causing thermal heating of the thermoablative nanoparticle and destruction of cancer cells covered by the nanofibril network. Alternatively, the conjugate can be co-administered with cytotoxic or immunotherapeutic agents that are well known in the art.

In addition, chemotherapeutic agents, immunotherapeutic agents, or radiotherapeutic agents, as well as surgical intervention can be used in a coordinated manner with the conjugate or pharmaceutical compositions of the present invention. Thus, a chemotherapeutic agent, an immunotherapeutic agent, or a radiotherapeutic agent can be administered to a patient before or after treatment with the conjugate or pharmaceutical compositions of the present invention. Alternatively, surgical resection of a tumor can be carried out before or after treatment with the conjugates or pharmaceutical compositions of the present invention. Optimization of such concurrent therapies is contemplated.

In one embodiment, the chemotherapeutic agent is a platinum-containing chemotherapeutic. Exemplary platinum-containing chemotherapeutics include, without limitation, cisplatin and carboplatin.

Yet another aspect of the invention relates to a method for modulating the cell membrane microheterogeneity. This method includes contacting a cell that expresses an esterase with hydrolytic activity, a phosphorylase, or a sulfatase with the conjugate or pharmaceutical composition of the invention, wherein said contacting is effective to cause intracellular or pericellular self-assembly of the conjugate upon enzymatic cleavage of the enzymatically cleavable-moiety, enzymatic dephosphorylation of the phosphorylated amino acid, or enzymatic desulfation of the sulfated amino acid. As a consequence of intracellular or pericellular assembly, or both intracellular and pericellular self-assembly, of the activated conjugate, or both, in the form of a hydrogel network, the resulting network alters cellular membrane microheterogeneity in the contacted cell.

A still further aspect relates to the promotion of cell survival with a conjugate according to the invention where the conjugate lacks an enzymatically activated conjugate (i.e., the conjugate lacks an enzymatically cleavable moiety and lacks a phosphorylated or sulfated amino acid). As demonstrated in the accompanying examples, the exposure of cells to such a conjugate (e.g., conjugate 3) can promote cell survival.

EXAMPLES

The examples below are intended to exemplify the practice of the present invention but are by no means intended to limit the scope thereof.

Materials and Methods for Examples 1-4

Materials and Instruments

2-Cl-trityl chloride resin (1.0-1.2 mmol/g), Fmoc-OSu, and other Fmoc-amino acids were obtained from GL Biochem (Shanghai, China). Other chemical reagents and solvents were obtained from Fisher Scientific; all chemical reagents and solvents were used as received from commercial sources without further purification; alkaline phosphatase was purchased from Biomatik. Dulbecco's modified Eagle's medium (DMEM), McCoy's 5a Medium, and 1640 Medium were purchased from ATCC and fetal bovine serum (FBS) and penicillin/streptomycin were purchased from Gibco by Life Technologies. 3-(4,5-Dimethylthiazol-2-yl)-2,5-diphenyltetrazolium bromide (MTT) was purchased from ACROS Organics. All precursors were purified with Water Delta600 HPLC system, equipped with an XTerra C18 RP column. LC-MS spectrum was obtained on Waters Acquity Ultra Performance LC with Waters MICROMASS detector, ultraviolet-visible (UV) spectra on JASCO J-810 spectrophotometer, and $^1$H-NMR spectra on Varian Unity Inova 400, and TEM images on Morgagni 268 transmission electron microscope. MTT assay for cell toxicity test on DTX880 Multimode Detector. Confocal microscopy images (CLSM) was carried on Leica TCS SP2 spectral confocal microscope or Marianas Spinning Disk confocal microscope.

TEM Sample Preparation

Sample solution (5 sufficient to cover the grid surface) was placed on the grid. Approximately 10 sec later, sample was rinsed by placing a large drop of the ddH$_2$O on parafilm and allowing the grid to touch the water drop, with the sample-loaded surface facing the parafilm. The grid was tilted and water was gently absorbed from the edge of the grid using a filter paper sliver. This procedure was repeated 3 times. Immediately after rinsing, the staining was conducted by placing a large drop of the uranyl acetate (UA) stain solution on parafilm and allowing the grid to touch the stain solution drop, with the sample-loaded surface facing the parafilm. The grid was tilted and the stain solution was gently absorbed from the edge of the grid using a filter paper sliver. Next, the grid was allowed to dry in air and the grid was examined as soon as possible.

Cell Culture

HeLa, Saos-2, HS-5, HepG2, T98G, and A2780 cells were purchased from American-type Culture Collection (ATCC, USA). A2780cis cell was purchased from Sigma. HeLa cells, HepG-2 cells, and T98G cells were cultured in MEM Medium supplemented with 10% v/v fetal bovine serum, 100 U/mL penicillin, and 100 µg/mL streptomycin. Saos-2 cells were cultured in McCoy's 5a Medium (for Saos-2) supplemented with 15% v/v fetal bovine serum, 100 U/mL penicillin, and 100 µg/mL streptomycin. HS-5 cells were cultured in Dulbecco's Modified Eagle's medium (DMEM) supplemented with 10% v fetal bovine serum (FBS), 100 U/mL penicillin, and 100 µg/mL streptomycin. A2780cis cells were cultured in RPMI 1640 Medium supplemented with 10% v/v fetal bovine serum, 100 U/mL penicillin, and 100 µg/mL streptomycin (cisplatin only necessary every 2-3 passages). All cells were maintained at 37° C. in a humidified atmosphere of 5% $CO_2$.

MTT Assay

An MTT assay was used to test the cytotoxicity. All different cell lines were seeded in 96-well plates at $1\times10^5$ cells/well for 24 hours followed by removal of the culture medium and subsequent addition of culture medium containing different concentrations of the precursors. At designated time (24/48/72 hours), 10 µL MTT solution (5 mg/mL) was added to each well and incubated at 37° C. for another 4 hours, and then 100 µL of SDS-HCl solution was added to stop the reduction reaction and dissolve the purple formazan. The absorbance of each well at 595 nm was measured by a multimode microplate reader. The cytotoxicity assay was performed three times and the average value of the three measurements was taken.

Actin Staining

Cells in exponential growth phase were seeded in confocal dish (3.5 cm) at $1\times10^5$ to $2\times10^5$ cells per dish. After putting the dish in incubator for 24 hours, culture medium was removed, and fresh medium containing precursor (12.5 µM 1a for A2780cis, 25 µM 1a for HeLa) was added. After 12 hours, the medium was removed and PBS was used to wash the cells for three times. After fixing by 4% paraformaldehyde for 15 minutes, 1 mL of 0.1% Triton X-100 in PBS buffer was added for 30 minutes. After washing the cells three times by PBS, 1 mL of 0.1% BSA in PBS was added for 30 minutes, and then the cells were washed by PBS for three times. 1 mL of PBS containing 5 unit of Alexa 633 was added to the cells for 1 hour. After removing the buffer and washing the cells three times by PBS, 1 mL of Hoechst (1 μg/mL) was added for 10 minutes. Then, the cells were washed three times with PBS buffer before imaging.

Antibody Staining

Procedure recommended by ABCAM for antibody staining was used. Cells were seeded (100,000-200,000 cell/3.5 cm confocal dish) and attachment was allowed (24 hours). Cells were incubated with 12.5 μM of precursor 1a for 12 hours or 24 hours. Then the cells were washed with PBS buffer three times and fixed by 4% formaldehyde for 15 minutes. Fixed cells were then washed with PBS buffer three times and incubated in 1.0% BSA/10% normal goat serum/0.3M glycine in 0.1% PBS-Tween for 1 hour to permeabilize the cells and block non-specific protein-protein interactions. Then they were washed with PBS buffer three times and incubated with the primary antibody (diluted 1/100, overnight at 4° C.). Then they were washed with PBS buffer three times and exposed to the secondary antibody (ab150077 Alexa Fluor® 488 goat anti-rabbit IgG (H+L), green) at 2 μg/ml (diluted 1/1000) for 1 hour. Hoechst 33342 was used to stain the cell nuclei (blue). The sample was washed with PBS buffer three times and mounted for imaging.

Example 1—Synthesis of Cholesterol-Amino Acid Conjugates

The synthetic process of Fmoc-Tyr(PO$_3$H$_2$)—OH was according to the previous work (see Shi et al., "D-Amino Acids Modulate the Cellular Response of Enzymatic-Instructed Supramolecular Nanofibers of Small Peptides," *Biomacromolecules* 15:3559-68 (2014), which is hereby incorporated by reference in its entirety). Both D- and L-amino acids were prepared. Otherwise, Fmoc-protected tyrosine and phenylalanine were used as reagents to prepare non-phosphorylated conjugates. The synthetic route of conjugation of cholesterol and amino acid was straightforward. Briefly, 1 mM of cholesteryl chloroformate was dissolved in 100 mL of acetone, amino acid dissolved in water with pH about 8 was added dropwise to the above solution. After stirring at room temperature for 24 hours, acetone was removed, and HCl was added to adjust the pH to 3, after that the reaction mixture was filtered. HPLC was used to purify the upper portion for amino acid with phosphate, and flash column chromatography was used to purify amino acid without phosphate. The yield of all precursors was more than 70%.

Scheme 1: Synthetic route of cholesterol derivatives.

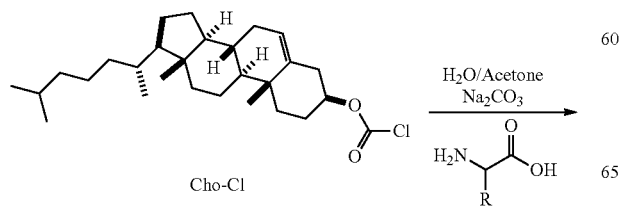

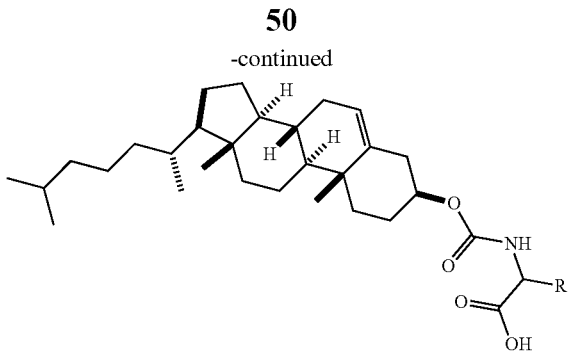

R = side chain of amino acid

The molecular structures of cholesterol conjugates 1a (Cholesterol-(phospho)D-Tyr), 1b (Cholesterol-D-Tyr), 2a Cholesterol-(phospho)L-Tyr, 2b (Cholesterol-L-Tyr), and 3 (Cholesterol-D-Phe) are shown below:

1a

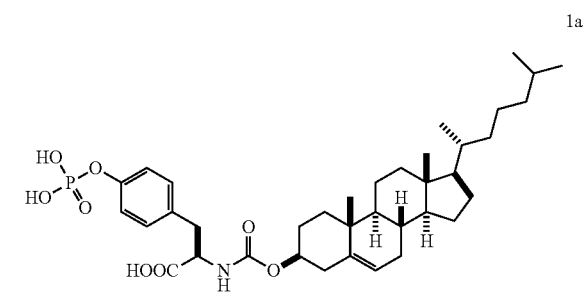

1b

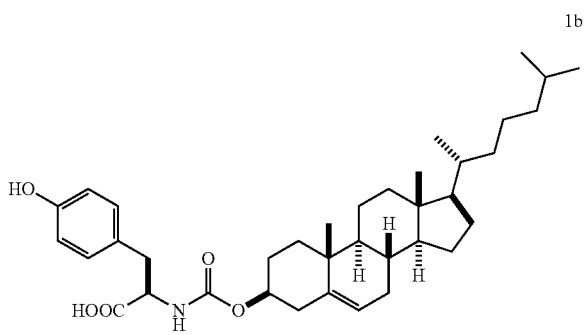

2a

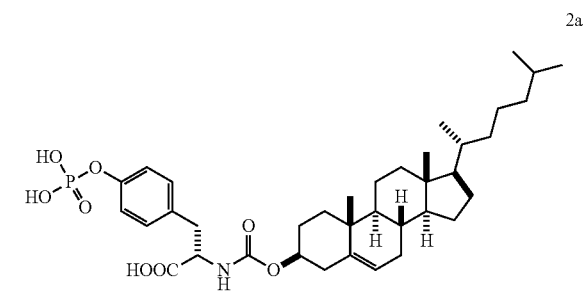

-continued

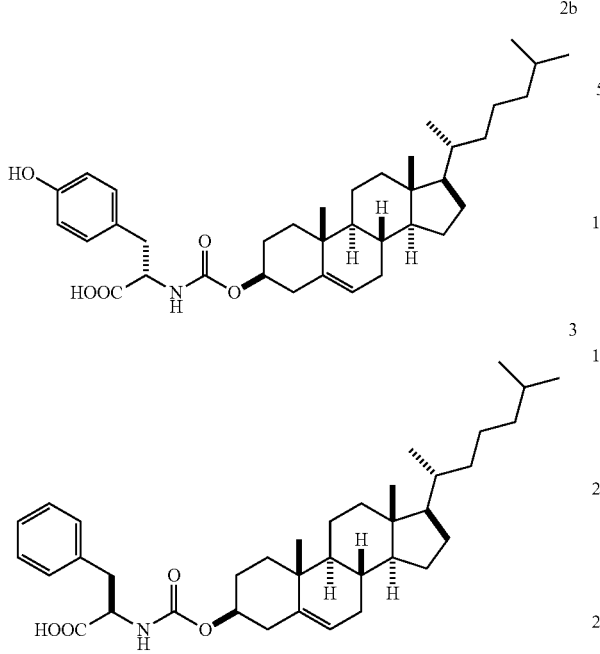

After purifying the conjugates 1a, 1b, 2a, 2b, and 3, their structure was characterized and confirmed by $^1$H-NMR and 31P-NMR.

Example 2—Activity of Cholesterol-Amino Acid Conjugates Against Ovarian Cancer Cells The activity of conjugate 1a against a platinum-resistant, ovarian cancer cell line (A2780cis) (Behrens et al., "Characterization of a Cis-Diamminedichloroplatinum(Ii)-Resistant Human Ovarian Cancer Cell Line and its Use in Evaluation of Platinum Analogues," *Cancer Res.* 47:414 (1987); Masuda et al., "Increased DNA Repair as a Mechanism of Acquired Resistance to Cis-Diamminedichloroplatinum (II) in Human Ovarian Cancer Cell Lines," *Cancer Res.* 48:5713 (1988), which are hereby incorporated by reference in their entirety) was first examined. To assess the efficacy of conjugate 1a, the assay was carried out in parallel using the known, clinically used cytotoxic agent, cisplatin.

As shown in FIG. 2A, 1a significantly inhibited A2780cis cells and was even more potent than cisplatin (compare FIG. 2B). The IC$_{50}$ of 1a was 11 µM (7.7 µg/mL, 48 hours) and 9 µM (6.3 µg/mL, 72 hours), which is 6 or 4 times lower than the IC$_{50}$ of cisplatin against A2780cis-71 µM (21.2 µg/mL, 48 hours) and 41 µM (12.2 µg/mL, 72 hours), respectively. More importantly, the IC$_{50}$ dosage (i.e., in terms of µg/mL) of 1a was much lower than cisplatin against A2780cis, promising an effective drug candidate for treating platinum-resistant ovarian cancers. As shown in FIG. 2A, the dosage curve of 1a exhibits a threshold concentration, a phenomenon that deviates from conventional dosage curve and agrees with the formation of molecular aggregation (Irwin et al., "An Aggregation Advisor for Ligand Discovery," *J. Med. Chem.* 58:7076 (2015); Sassano, et al., "Colloidal Aggregation Causes Inhibition of G Protein-Coupled Receptors," *J. Med. Chem.* 56:2406 (2013); Owen et al., "Colloidal Aggregation Affects the Efficacy of Anticancer Drugs in Cell Culture," *ACS Chem. Biol.* 7:1429 (2012), which are hereby incorporated by reference in their entirety).

As a control, L-phosphotyrosine was used to replace the D-phosphotyrosine in 1a to generate 2a (see Example 1) and the inhibitory activity of 2a against A2780cis was examined. The IC$_{50}$ of 2a against A2780cis was 22 µM (15.2 µg/mL, 72 hours), agreeing with that 1b and 2b result in slightly different assemblies (vide infra). As additional controls, the inhibitory activity of 1b and 2b, the dephosphorylated products of 1a and 2a, were also tested against A2780cis. The IC$_{50}$ values (at 72 hours) of 1b and 2b were 50 µM and 36 µM, respectively, which were considerably higher than those of 1a and 2a. These results indicate that the assemblies resulted from enzymatic dephosphorylation contributes to the higher inhibitory activity of 1a (or 2a) than that of 1b (or 2b) against A2780cis cells.

Example 3—Examining Mode of Action for Cholesterol-(Phospho)D-Tyr Conjugate

To further understand the inhibitory activity of 1a, transmission electron microscopy (TEM) was used to confirm the EISA of 1b. As shown in FIG. 3A, 1a (1.0 wt %) in aqueous solution (pH7.4) afforded disorder aggregates after solvent evaporated. In contrast, uniform nanofibers (diameter of 10±2 nm) formed after the addition of ALP (1 U/mL) into the solution of 1a (FIG. 3B). The resulted nanofibers entangled with each other to result in a viscous solution. Without the use of ALP, the direct dissolution of 1b in water (1.0 wt %) resulted in a solution containing spheres-like vesicle with diameter of 25±2 nm (FIG. 4A). Similar to 1a, dissolving 2a (1.0 wt %) in water resulted in a solution containing disorder aggregates (most of them existing as nanoparticles) (FIG. 3C). The addition of ALP (1 U/mL) into the solution of 2a resulted in relatively uniform nanofibers (diameter of 15±2 nm) (FIG. 3D). But the direct dissolution of 2b (1.0 wt %) provided an aqueous solution containing nanoribbon with the diameter of 17±2 nm and in several hundred nanometer length (FIG. 4B). These observations, collectively, confirmed that enzymatic reaction modulated the morphology of the assemblies of the cholesterol conjugates, which partially contributed to the different inhibitory activities of 1a, 1b, 2a, and 2b. That is, being exposed to the cancer cell, 1a (or 2a) turns into 1b (or 2b), a process catalyzed by the extra- or intracellular enzymes of the cancer cells; the resulting 1b (or 2b) self-assembled to form nanoscale assemblies that result in death of the cancer cell. Not being generated by the EISA process, 1b or 2b showed less cytotoxicity than that of 1a or 2a. Because of the different morphologies of the assemblies of 1b and 2b after enzymatic dephosphorylation of 1a and 2a, respectively, it was reasonable for 1a and 2a to exhibit different activities against cancer cells (see Example 2, supra).

Example 4—Activity of Cholesterol-Amino Acid Conjugates Against Non-Cancerous Cells To verify the selectivity of 1a against cancer cells, the HS-5 cell line (human bone marrow stroma cell line) was used; HS-5 hardly overexpresses ALP on cell surface. As shown in FIG. 5A, 1a at 12.5 µM was innocuous to HS-5. Similar to the case of A2780cis, 1b hardly inhibited the proliferation of HS-5 cells (FIG. 5A). To further confirm that ALP on cell surface (i.e., as an ectophosphatase) contributed to the inhibitory activity of 1a, A2780cis were incubated with 1a and ALP (1 U/mL). After 48 hour co-culture, cell viability indicated that exogenous ALP, indeed, partially rescued the A2780cis cells (FIG. 5B). Moreover, the addition of L-phenylalanine (L-Phe) or levamisole, two types of inhibitors of ALP (Fernley et al., "Inhibition of Alkaline Phosphatase by L-Phenylalanine," *Biochem. J.* 116:543 (1970); Borgers, "The Cytochemical Application of new Potent Inhibitors of Alkaline Phosphatases," *J. Histochem. Cytochem.* 21: 812 (1973), which are hereby incorporated by reference in their entirety), also resulted in higher cell viability of A2780cis (FIG. 5B). These partial rescue effects not only validated the contribution of the ALPs on the cell surface for cell death, but also indicated that intracellular phosphatases likely dephosphorylate 1a and generate intracellular assemblies of 1b to inhibit the cancer cells.

Example 5—Analyzing Mode of Action Against Cancerous Cells

To determine the modality of the cell death induced by EISA of 1b, A2780cis were co-incubated with 1a in the presence of a pan-caspase inhibitor (zVAD-fmk) (Slee et al., "Benzyloxycarbonyl-Val-Ala-Asp (OMe) Fluoromethylketone (Z-VAD.FMK) Inhibits Apoptosis by Blocking the Processing of CPP32," *Biochem. J.* 315:21 (1996), which is hereby incorporated by reference in its entirety), a PARP-1 inhibitor (PJ34) (Abdelkarim et al., "Protective Effects of PJ34, a Novel, Potent Inhibitor of Poly(ADP-ribose) Polymerase (PARP) in in Vitro and in Vivo Models of Stroke," *Int. J Mol. Med.* 7:255 (2001), which is hereby incorporated by reference in its entirety), or a necroptosis inhibitor (Nec-1) (Degterev et al., "Chemical Inhibitor of Nonapoptotic Cell Death With Therapeutic Potential for Ischemic Brain Injury," *Nat. Chem. Biol.* 1:112 (2005); Degterev et al., "Identification of RIP1 Kinase as a Specific Cellular Target of Necrostatins," *Nat. Chem. Biol.* 4:313 (2008), which are hereby incorporated by reference in their entirety). The addition of zVAD-fmk, PJ34, or Nec-1 all rescued the cells, but only partially (FIG. 5B). These results implied that 1a induced cell death via multiple mechanisms, including apoptosis and necroptosis, by activating both extrinsic and intrinsic cell death signaling.

Antibody staining was used to examine the extrinsic cell death signaling molecules induced by the assemblies of 1b. After 1a was incubated with A2780cis cells for 12 or 24 hours, the primary antibodies of cell death receptors (i.e., anti-CD95, anti-DR3, anti-DR5, anti-TNFR1, and anti-TNFR2) were added to bind their corresponding receptors on the cells, then fluorescent secondary antibody were used to reveal the bindings. As shown by the fluorescent imaging, the addition of 1a resulted in significant clustering of DR5 (FIGS. 5C and 5D), while the clustering of DR3 or TNF-R1 was rather moderate (FIGS. 6 and 7A-B), and there was little clustering of CD95 or TNF-R2 (FIGS. 6 and 7A-B). These results suggested that, after ALP turned 1a to 1b, the assemblies of 1b likely promiscuously interacted with DR5, DR3, and TNFR1 to result in cell death (FIG. 5A-D).

Considering that cholesterol is the basic component of lipid rafts, dynamic assemblies in cell membrane (Simons et al., "Functional Rafts in Cell Membranes," *Nature* 387:569 (1997), which is hereby incorporated by reference in its entirety), laurdan, a commonly used probe for the polarity membrane (Parasassi et al., "Quantitation of Lipid Phases in Phospholipid Vesicles by the Generalized Polarization of Laurdan Fluorescence," *Biophys. J.* 60:179 (1991), which is hereby incorporated by reference in its entirety), was used to examine the changes of lipid rafts upon the EISA of 1b. Without treatment of 1a, the fluorescence of laurdan dispersed relatively evenly in the whole cell membrane (FIG. 8C). But the addition of 1a resulted in increased inhomogeneity of the fluorescence (FIG. 8D). This result indicated that the addition of 1a promoted the formation of lipid rafts, agreeing with prior reports that lipid rafts participate cell death signaling (Simons et al., "Lipid Rafts and Signal Transduction," *Nat. Rev. Molecular Cell Biol.* 1:31 (2000), which is hereby incorporated by reference in its entirety).

To examine whether the intracellular assemblies of 1b, formed after 1a enters cells, alter the dynamic of cytoskeleton proteins to cause cell death (Li et al., "Enzyme-Instructed Intracellular Molecular Self-Assembly to Boost Activity of Cisplatin against Drug-Resistant Ovarian Cancer Cells," *Angew. Chem., Int. Ed.* 54:13307 (2015); Zhou et al., "Taurine Boosts Cellular Uptake of Small D-Peptides for Enzyme-Instructed Intracellular Molecular Self-Assembly," *J. Am. Chem. Soc.* 137:10040 (2015), which are hereby incorporated by reference in their entirety), CLSM was used to examine the changes of F-actin. Compared with control group, A2780cis cells treated with 1a (12.5 µM) exhibited short, ill-defined actin filament (FIGS. 8A-B), indicating that the assemblies of 1b can interact with F-actin and disrupt the dynamic of F-actin. Although the alteration of cytoskeleton and the changes of cell integrity can be the consequence of cell death, the cell viability test shows more than 80% of cells to be viable when being incubated with 1a at 24 hours. Thus, it is more likely that the interaction between the assemblies of 1b and F-actin causes the cell death.

Example 6—Activity of Cholesterol-Amino Acid Conjugates Against Additional Cancer Cells To confirm that assemblies of the cholesterol conjugate are able to inhibit other cancer cell lines, 1a was incubated with HeLa cells, a widely studied malignant cervical cancer cell line. As shown in FIG. 9A, after 48 hours, the $IC_{50}$ of 1a against HeLa cell was 18.6 µM, which is about 4 times lower than that of 1b (89.7 µM). This result indicated that the assemblies of 1b, formed by the EISA, effectively inhibit HeLa cells that are known to overexpress ALP (Tokumitsu et al., "Intracellular Alkaline Phosphatase Activity in Cultured Human Cancer Cells," *Histochemistry* 73:1 (1981); Herz F. "Alkaline Phosphatase Isozymes in Cultured Human Cancer Cells," *Experientia* 41:1357 (1985), which are hereby incorporated by reference in their entirety). Interestingly, the $IC_{50}$ of 2a against HeLa cell is 43.8 only slightly lower than that of 2b (59.2 Considering that 2b, as a diastereomer of 1b, form different assemblies with those of 1b, it is reasonable that the activity of 2a (or 2b) differ from that of 1a (or 1b), respectively.

Similar to the case of A2780cis, the change of the viability of the HeLa cells co-incubated with 1a and several specific inhibitors was examined to understand the mechanism of cell death. As shown in FIG. 9B, the co-incubation of ALP, L-Phe, levamisole, zVAD-fmk, PJ34, or Nec-1 significantly increased the viability of the HeLa cell treated by 1a. Given the results with A2780cis, these results confirmed that 1a results in the death of HeLa cells via multiple and interdependent mechanisms (e.g., involving both apoptosis and necroptosis). The use of laurdan to examine the changes of lipid rafts in HeLa cell also revealed that, while the untreated HeLa cells exhibited homogeneously distributed green fluorescence (FIG. 9C), the number of green fluorescent puncta increased considerably in the cell membrane of the HeLa cells treated by 1a (FIG. 9D). This result, similar with that of A2780cis, indicated that the addition of 1a promotes the formation of lipid rafts, which modulates cell death signaling and results in cell death. To verify the assemblies of 1b interact with F-actin, actin tracker was used to visualize F-actin filament in HeLa cells. Like untreated A2780cis, the untreated HeLa cells exhibited long actin filaments across the cell cytoplasm (FIG. 9E). But HeLa cells treated by 1a showed considerably decreased actin filaments (FIG. 9F) and significantly increased puncta near cell surface, suggesting that the assemblies of 1b significantly disrupts the dynamics of actins to result in the clusters of scattered filaments near the inner-leaf of membrane lipids. Because most HeLa cells were viable at 24 hours, the assemblies of 1b likely interacted with F-actin and then induced cell death.

Figure 11:
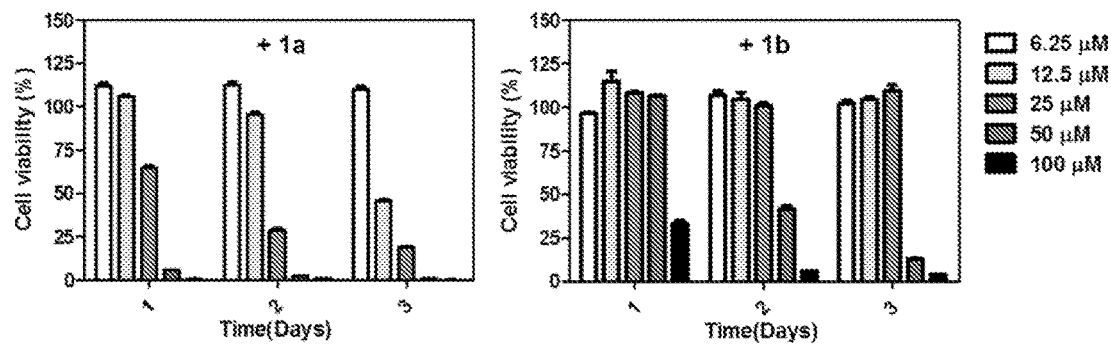
FIG. 11 is a panel of graphs that show cell viability of Kuramochi ovarian cancer cells treated with 1a and 1b at 24, 48 and 72 hours.

Additional cell viability assays were carried out using conjugates 1a and 1b, optionally with 3, against HepG2 human liver carcinoma cells, Saos-2 osteosarcoma cells, T98G glioblastoma cells, HS-5 (normal bone marrow stromal cells), A2780 ovarian cancer cells (parental line to A2780cis), and Kuramochi ovarian cancer cells. These results are shown in FIGS. 10 and 11, and the corresponding $IC_{50}$ values are reported in Table 1 below. Conjugate 1a was particularly effective against ovarian and cervical cancer cells.

TABLE 1

The $IC_{50}$ Value of 1a Against Different Cell Lines at 48 Hours or 72 Hours

| Cell type | HepG-2 | Saos-2 | T98G | HeLa | HS-5 | Kuramochi |
|---|---|---|---|---|---|---|
| $IC_{50}$ (μM, 48 hours) | 45 | 41 | 48 | 19 | 32 | 19 |
| $IC_{50}$ (μM, 72 hours) | 35 | 26 | 37 | 16 | 21 | 13 |

Discussion of Examples 1-6

Because of the well-established extrinsic and intrinsic pathways for cell death (Ashkenazi et al., "Regulated Cell Death: Signaling and Mechanisms," *Annu. Rev. Cell Dev. Biol.* 30:337 (2014), which is hereby incorporated by reference in its entirety), it was hypothesized that the use of EISA for simultaneously activating extrinsic and intrinsic cell death signaling will increase the efficacy of EISA for killing cancer cells. Such a design required nanoscale assemblies to form both on cell surface and inside cells. To meet this requirement, the use of cholesterol as a building block was chosen to design the precursors for EISA because, as an evolutionarily optimized molecule, cholesterol is known to present both on cell surface (Heino et al., "Dissecting the Role of the Golgi Complex and Lipid Rafts in Biosynthetic Transport of Cholesterol to the Cell Surface," *Proc. Natl. Acad. Sci. U.S.A.* 97:8375 (2000); Slotte at al., "Binding of High Density Lipoproteins to Cell Receptors Promotes Translocation of Cholesterol From Intracellular Membranes to the Cell Surface," *J. Biol. Chem.* 262:12904 (1987), which are hereby incorporated by reference in their entirety) and inside cells (Neufeld et al., "Intracellular Trafficking of Cholesterol Monitored With a Cyclodextrin," *J. Biol. Chem.* 271:21604 (1996); Simons et al., "How Cells Handle Cholesterol," *Science* 290:1721 (2000); Rajendran et al., "Subcellular Targeting Strategies for Drug Design and Delivery," *Nat. Rev. Drug Discovery* 9:29 (2010), which are hereby incorporated by reference in their entirety). Cholesterol was covalently conjugated with a phosphotyrosine to generate a precursor (1a) for EISA. Results revealed that (i) 1a, besides being orders of magnitude more potent than the previous reported precursors for EISA (Zhou, "Enzyme-Instructed Self-Assembly: a Multistep Process for Potential Cancer Therapy," *Bioconjugate Chem.* 26:987 (2015), which is hereby incorporated by reference in its entirety), is more potent than cisplatin (CDDP) for inhibiting platinum-resistant ovarian cancer cells; (ii) 1a inhibits cancer cells selectively because EISA generates the nanoscale assemblies of 1b in-situ on the cancer cells; (iii) the assemblies of 1b, indeed, were able to activate extrinsic and intrinsic cell death signaling simultaneously. By validating the concept shown in FIG. 1, this work illustrates EISA as a facile and powerful approach to generate multifaceted nanomedicine from the unified version of the building block of life (Marth J. D. "A Unified Vision of the Building Blocks of Life," *Nat. Cell Biol.* 10:1015 (2008), which is hereby incorporated by reference in its entirety) for controlling cell fates.

The conjugation of cholesterol and phosphotyrosine exhibited higher potency and higher selectivity than cisplatin against a platinum-resistant human ovarian carcinoma and human cervical carcinoma. The selective inhibitory activity of 1a relied on the phosphatases on and inside cells. These phosphatases dephosphorylated 1a to form 1b, and then 1b self-assembled to augment the lipid rafts and to disrupt intracellular protein homeostasis, thus resulting in cell death. Tyrosine residue was essential because the conjugate of phenylalanine and cholesterol (even at the concentration of 100 μM) was innocuous to A2780cis and HeLa cells (FIG. 10). As the first study to use EISA for modulating lipid rafts, this work illustrates a new way for developing efficient nanomedicine against drug resistant cancer, especially cisplatin resistant ovarian cancer.

Example 7—Analyzing Mode of Action Against Cancerous Cells

Figures 12A, 12B, 12C:
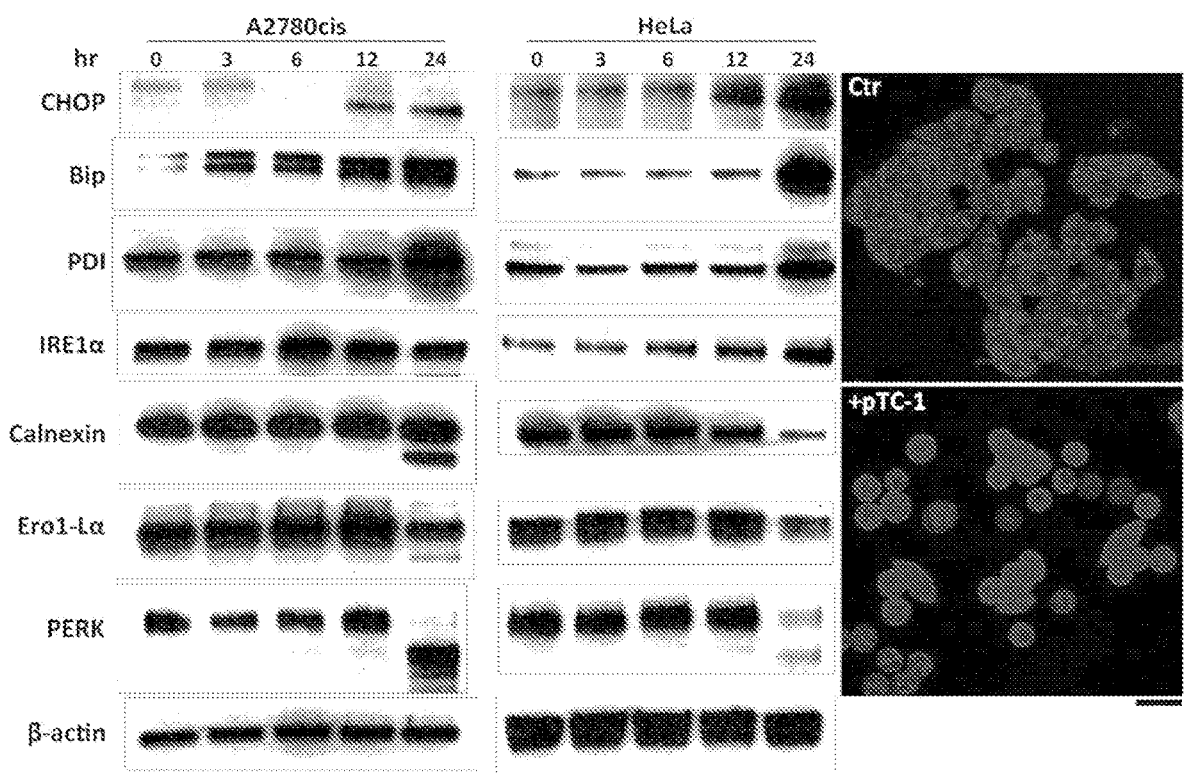
FIGS. 12A-C show that 1a induces cell apoptosis via ER stress and generates Reactive Oxygen Species ("ROS"). Western blot indicates the expression level changes of relative amount of ER stress markers in the treatment of 1a A2780cis (FIG. 12A) and HeLa cell lines (FIG. 12B).

Further exploration of the mode of action of 1a against A2780cis and HeLa cells was carried out via Western blot for the following ER stress markers: CHOP, Bip, PDI, IRE1α, Calnexin, Erol-Lα, PERK, and β-actin; or p-SAPK/JNK. Western blot was carried out via gel electrophoresis at 100 kv for 1.5 hrs, and then transferring the protein on the gel to PVDF membranes for overnight at 20 kv (4° C.). After that, the membrane was incubated with primary antibodies (obtained from Cell Signaling Technology) overnight at 4° C. The membrane was then incubated with secondary antibodies for 1 h at room temperature. This was followed by the reaction with ECL solutions for 10 minutes, and analysis of the results by autoradiography. Generation of ROS was detected in CLSM images via DHE emissions in exposed cells. CLSM imaging was carried out at the excitation of 543 nm and DHE emission was detected at the wavelength at 575 nm to 625 nm; or detection of anti-phospho-SRC and anti-phospho-Akt. Together, the WB and CLSM imaging demonstrates that 1a exposure induces cell apoptosis via ER stress and generation of ROS (FIGS. 12A-C).

In addition, 1a causes down regulation of cell survival proteins, Akt (Alexander, "Inhibiting the Akt Pathway in Cancer Treatment," *Pharmacy & Therapeutics* 36(4): 225-227 (2011), which is hereby incorporated by reference in its entirety) and Src (Irby et al., "Role of Src Expression and Activation in Human Cancer," *Oncogene* 19(49):5636-5642 (2000), which is hereby incorporated by reference in its entirety). Treatment of A2780cis cell lines with 1a (12.5 μM) for 24 hours downregulates expression of Src (FIGS. 13A-B) and Akt (FIGS. 13C-D). As demonstrated by Western blot, p-SAPK/JNK expression levels were enhanced following 24 hour treatment in A2780cis cell lines, indicating activation of pro-apoptotic pathways (FIG. 13E). When used in combination with other anti-cancer agents, TIC10, Apo2L/TRAIL, and doxorubicin, a mixture of 1a with the individual anti-cancer agents was prepared, and then the cells were incubated with the mixture. These combination treatments showed synergistic effects (FIGS. 13F-G).

Example 8—Synthesis of Cholesterol-Amino Acid Conjugates Containing NBD Fluorophore The molecular structures of cholesterol conjugates 11a (cholesterol-(phospho)y-(NBD)k) and 11b (cholesterol-y-(NBD)k) are shown below:

These conjugates were prepared using the synthesis procedure of Example 1, except that Fmoc-Lys was utilized. Coupling of NBD to the sidechain of lysine was carried out using the amine-reactive fluorogenic reagent (7-chloro-4-nitro-2,1,3-benzoxadiazole (NBD-Cl). See Gao et al., *Nat. Commun* 3:1033 (2012), which is hereby incorporated by reference in its entirety. HPLC was used to purify the upper portion for conjugates with (phospho)Tyr, and flash column chromatography was used to purify conjugates without

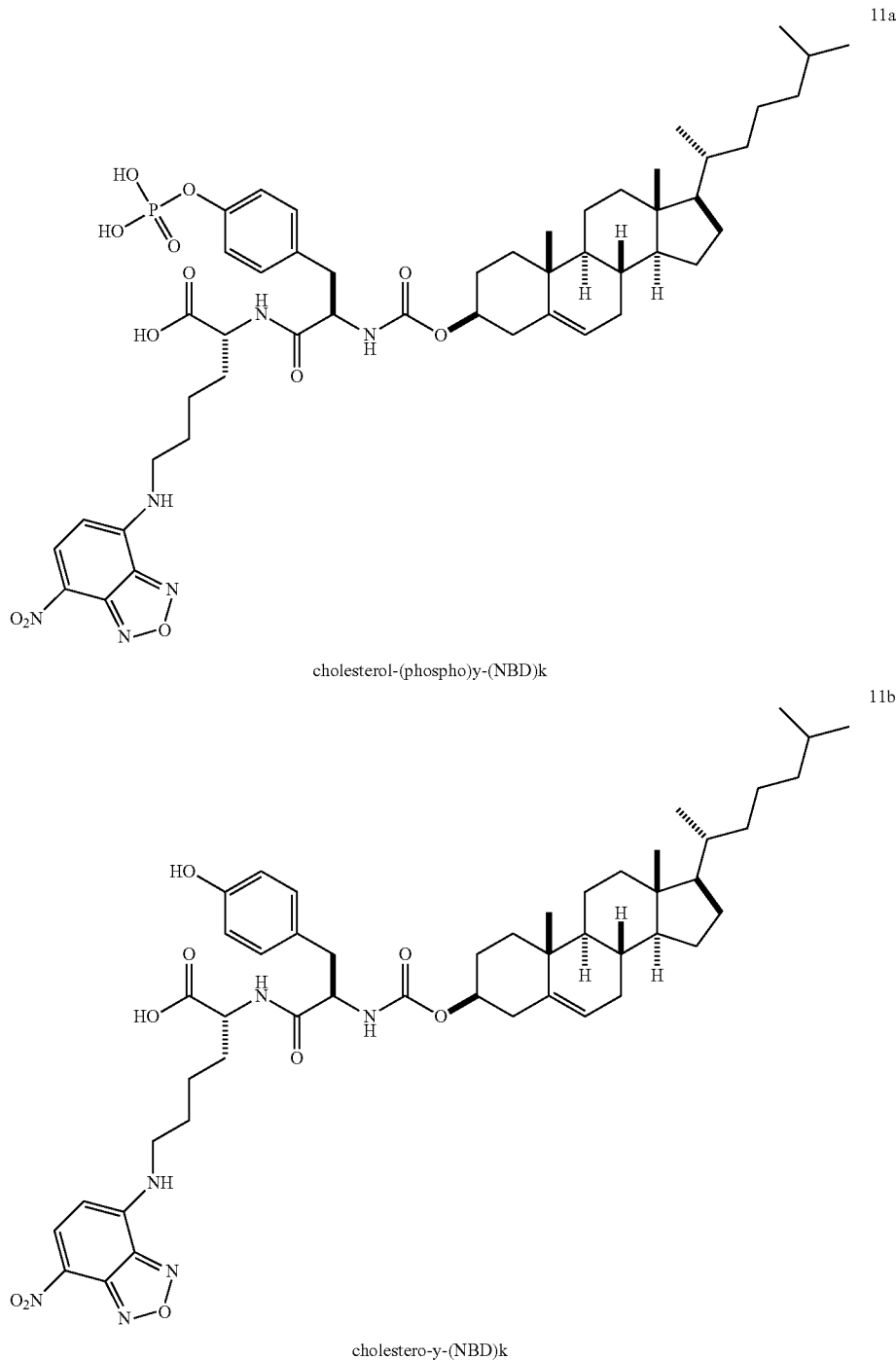

cholesterol-(phospho)y-(NBD)k cholestero-y-(NBD)k (phospho)Tyr. After purifying the conjugates 11a and 11b, their structure was characterized and confirmed by $^1$H-NMR and $^{31}$P-NMR.

Example 9—Visualization of Nano-Aggregates in Cancer Cell Lines

Different cancer cells at the density of 1.5×10$^5$ were seeded onto 3.5 cm confocal dish. After the growth of cells in cell incubator for 24 h, 11a (or 11b) at 25 µM was added to the above solution with completed medium. At designated times, PBS was used to wash cells 3 times for 1 minute. Hoechst 33342 was used to stain cell nucleus for 10 minutes, and cells were then washed using live cell imaging solution 3 times for 1 minute. Cells were maintained in live cell imaging solution, and CLSM was carried out immediately. The excitation of wavelength was 488 nm, and the emission was 500 nm to 596 nm.

Figure 14:
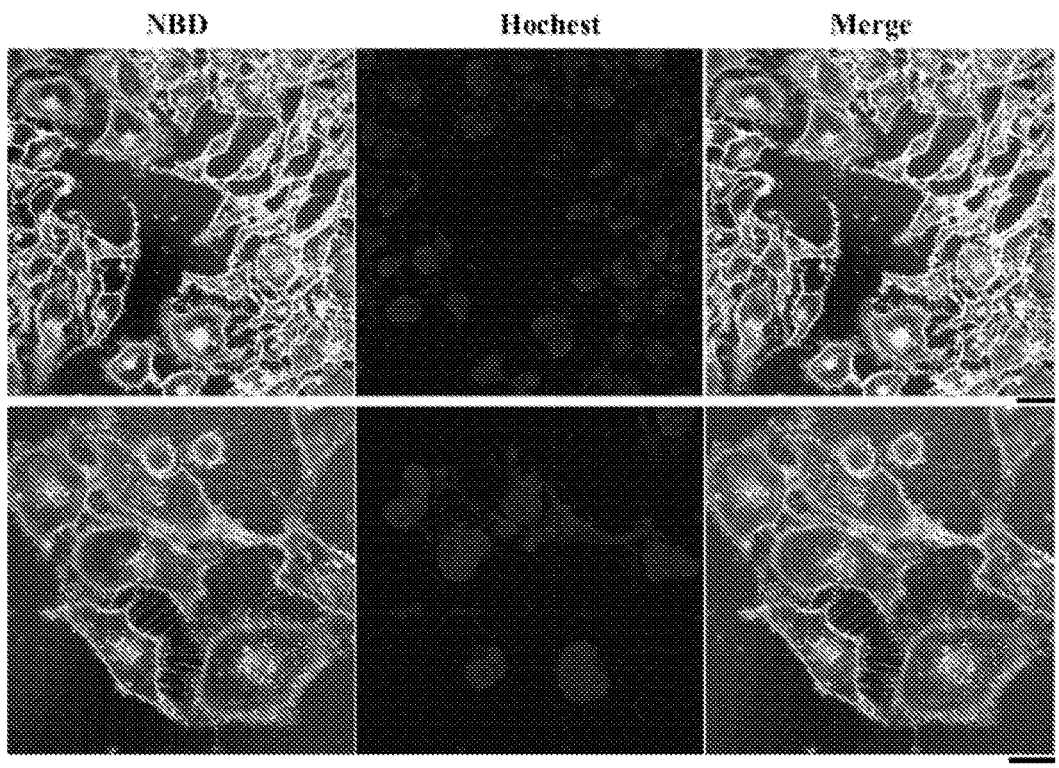
FIG. 14 is a panel of CLSM images of HeLa cells treated with 11a at the concentration of 25 μM for 8 h.
Figure 15:
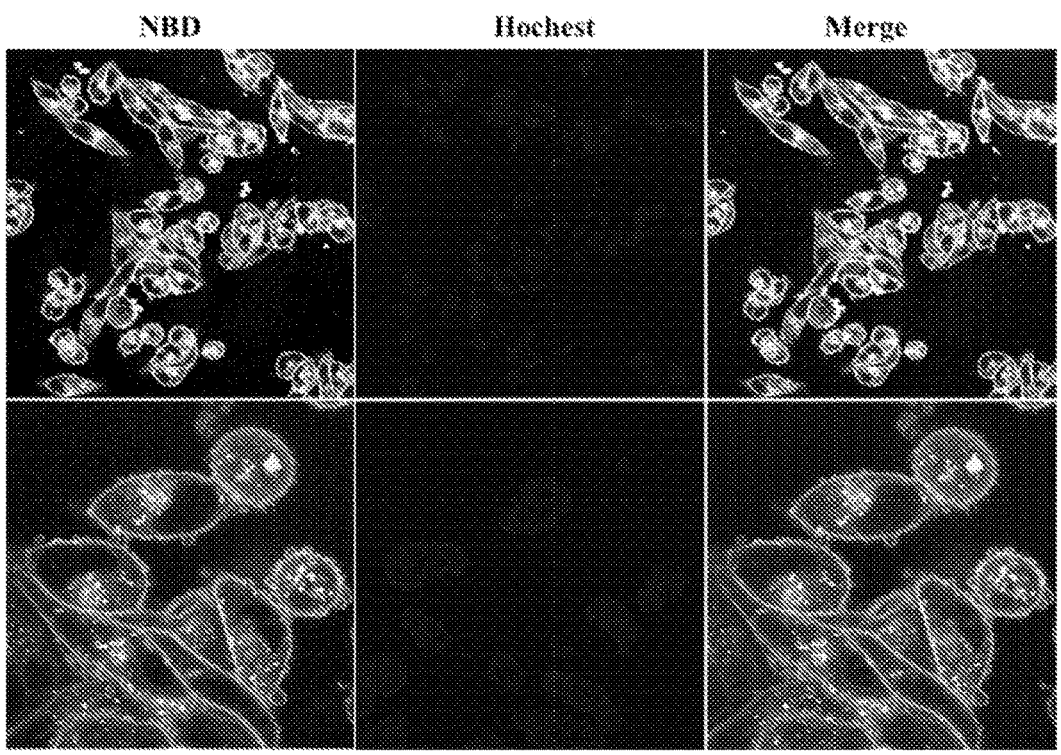
FIG. 15 is a panel of CLSM images of A2780cis cells treated with 11a at the concentration of 25 μM for 8 h.
Figure 16:
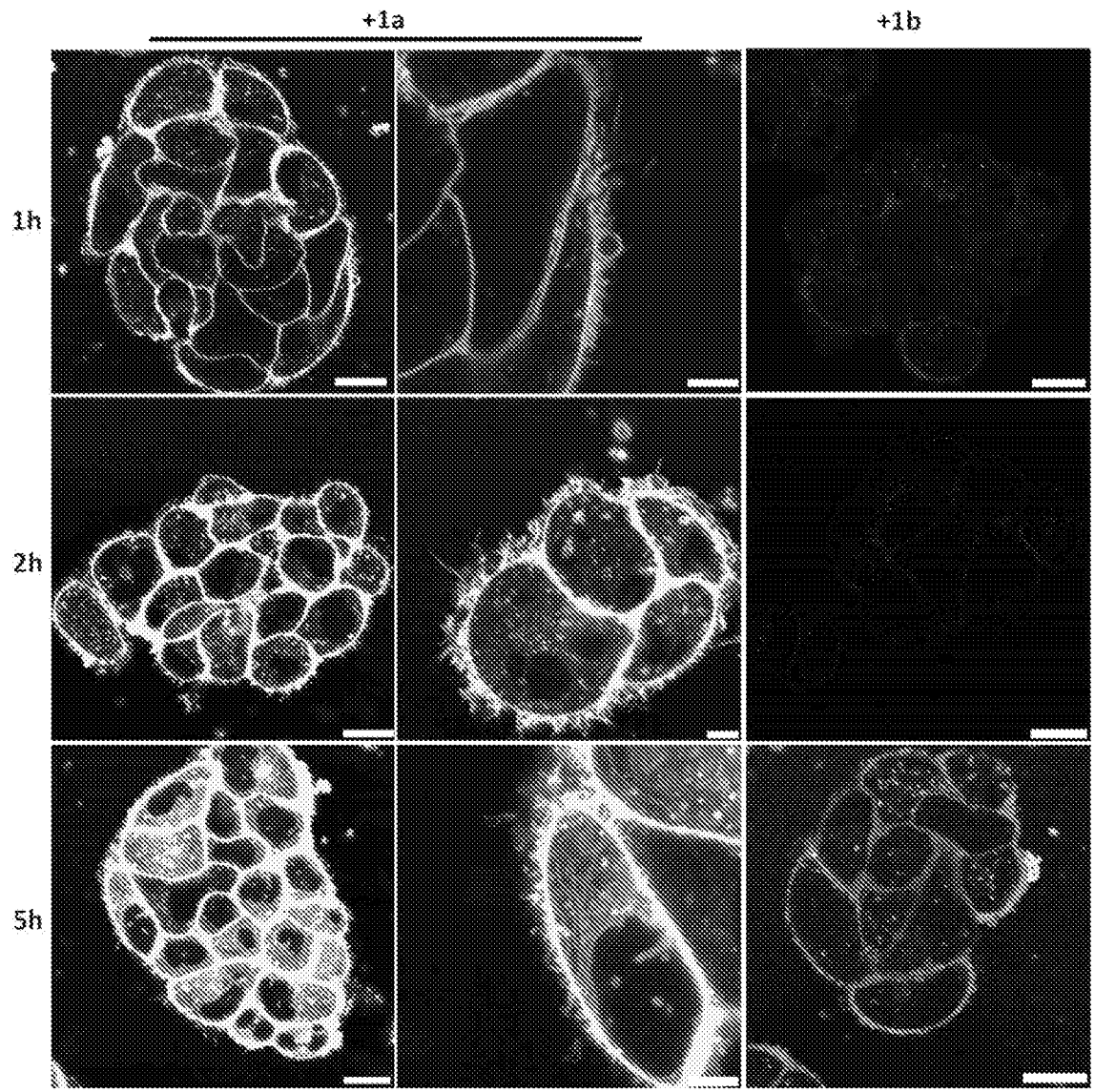
FIG. 16 is a panel of CLSM images of OVASHO cells treated with 11a or 11b at the concentration of 25 μM for 1, 2 and 5 h. Scale bar is 15 um for low magnification, and for high magnification is 5 μM.
Figure 17:
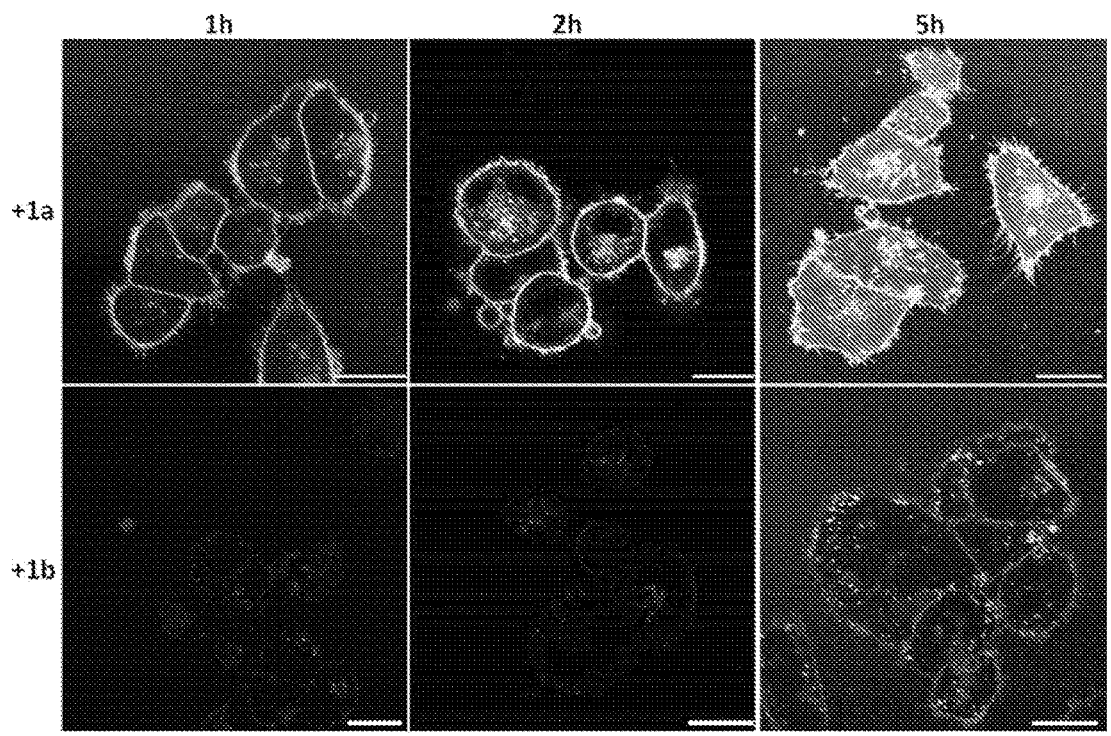
FIG. 17 is a panel of CLSM images of MES-SA/dx5 cells treated with 11a or 11b at the concentration of 25 μM for 1, 2 and 5 h. Scale bar is 15 um.
Figure 18:
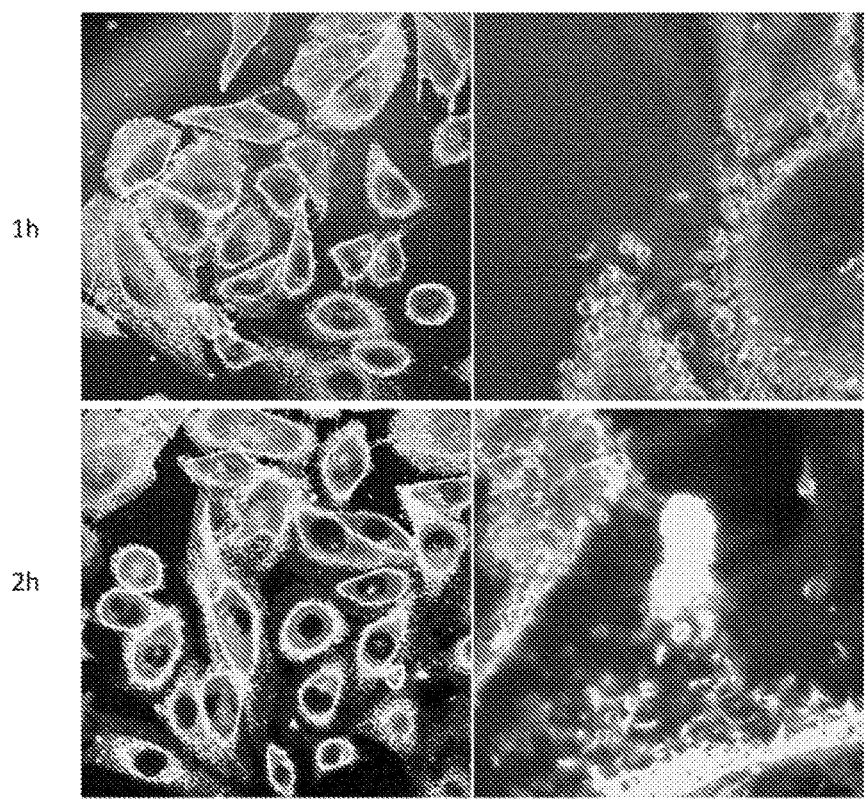
FIG. 18 is a panel of CLSM images of Saos-2 cells treated with 11a at the concentration of 25 μM for 1 and 2 h, and then staining with TNAP antibody. Green indicates the fluorescence of NBD and red shows the distribution of antibody.

NBD visualization confirmed presence of nano-aggregates in or on the treated cells. FIG. 14 shows HeLa cells treated with 11a, FIG. 15 shows A2780cis cells treated with 11a, FIG. 16 shows OVASHO cells treated with 11a or 11b, FIG. 17 shows MES-SA/dx5 cells treated with 11a or 11b, and FIG. 18 shows Saos-2 cells treated with 11a and then stained with TNAP antibody.

Example 10—Preparation of Doxorubicin-Loaded Nanoaggregates

Doxorubicin hydrochloride (Dox) was dissolved in DMSO to make 10 mM stock solution. Then the stock solution was diluted with PBS buffer or cell culture medium to prepare 1 µM or 0.5 µM work solution, and then different amounts of compound 1a from 6.25 µM to 100 µM was added. After 10 minutes at room temperature, the product of Dox-loaded nanoparticles was formed. These Dox-loaded nanoparticles were exposed to A2780cis cell line to directly measure toxicity.

Figure 19:
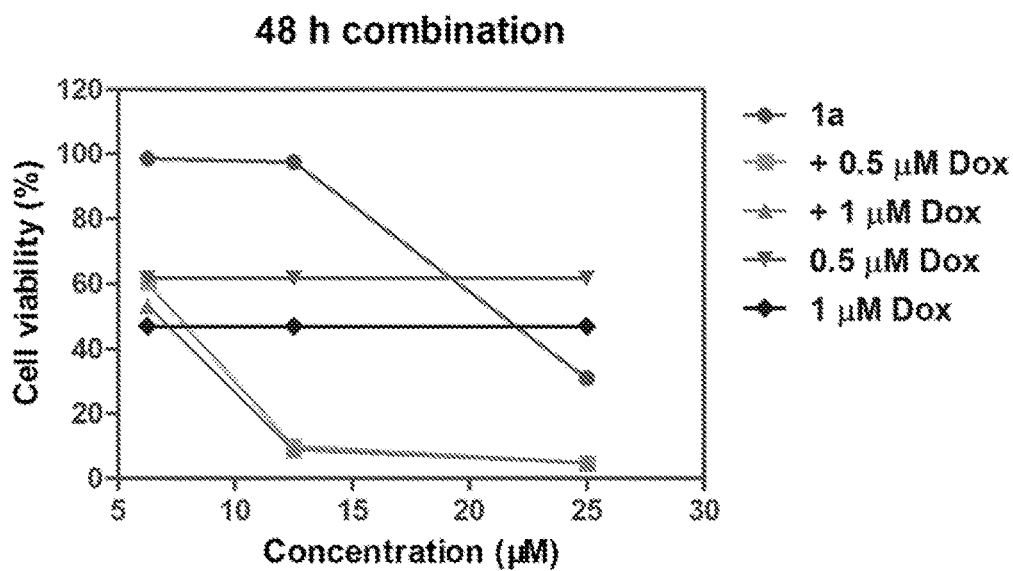
FIG. 19 is a graph illustrating that doxorubicin loaded nanoparticles enhance anti-proliferation efficiency against A2780cis cell line.

At approximately 12.5 µM 1a with 0.5 and 1.0 µM Dox, non-additive results were surprisingly obtained, whereby nanoparticles dramatically enhanced the cytotoxicity of Dox toward A2780cis cells (FIG. 19).

Figure 20:
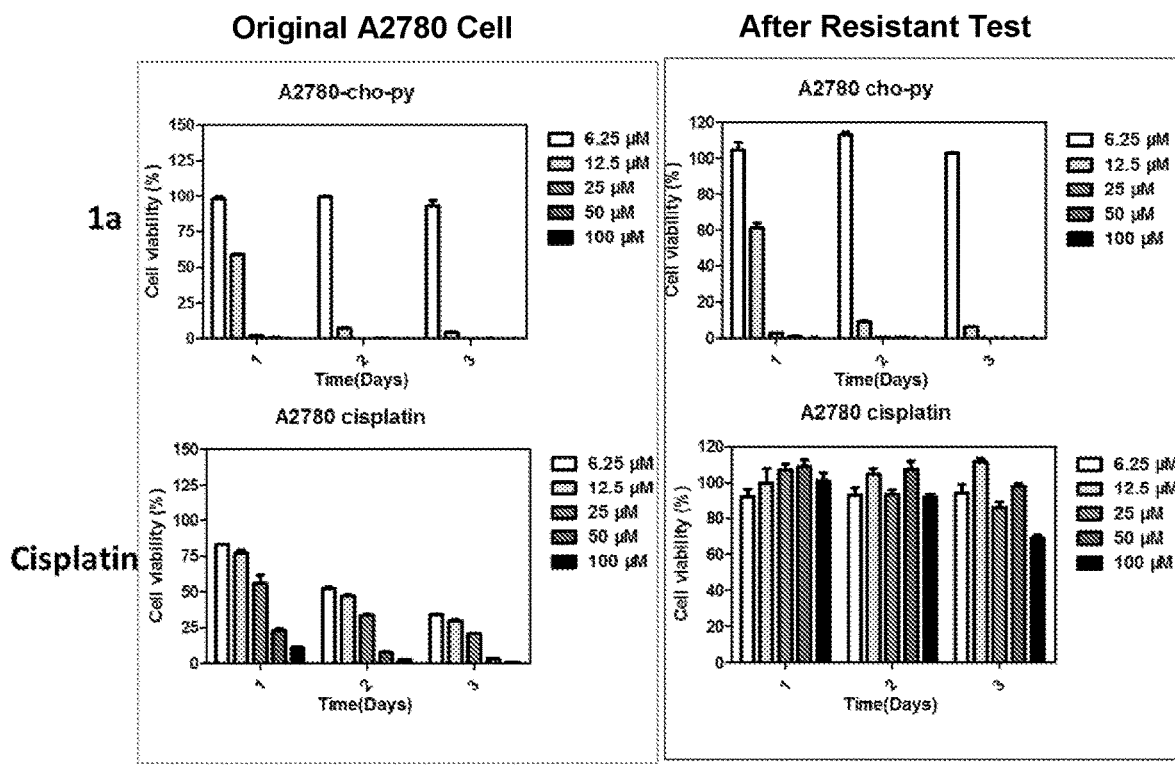
FIG. 20 is a panel of graphs that show cell viability of unstimulated A2780 cell line or selected A2780 cell line (after five weeks treatment of the precursors with gradually increase concentrations), incubated with either cho-py or cisplatin at different concentrations for 24 h, 48 h and 72 h.

Example 11—Activity of Cholesterol-Amino Acid Conjugate Against Non-Drug Resistant Cancer Cells The activity of 1a against non-drug resistant cancer cells was assessed using the A2780 cell line. Cell viability of an unstimulated A2780 cell line or selected A2780 cell line (after five weeks treatment of the precursors with gradually increased concentrations) was assessed after incubating with cho-py or cisplatin at different concentrations for 24 h, 48 h and 72 h. The results are shown in FIG. 20. 1a is able to inhibit ovarian cancer cells without acquired drug resistance (control: cisplatin caused platinum-resistance).

Prospective Example 12—In Vivo Treatment of Xenograft Mouse Ovarian Cancer Model Fifteen nude mice will be used for experiments to define the tumor growth curve. 1×10$^7$ A2780cis cells will implanted into the mice via intraperitoneal injection using a 25 G needle. Three of the tumor-bearing mice will used to define the tumor growth curve with control (saline) treatment, three mice will be given doxorubicin alone, three mice will be given 1a alone, three mice will be given 1a in combination with doxorubicin, and three mice will be given doxorubicin-loaded nanoaggregates prepared according to Example 10. The mice will injected 6 times, every 3 days starting at Day 1, with either 100 µL of PBS buffer (negative control), 3 mg/kg doxorubicin (positive control), 100 µL of 1a at 8 µg/µL (800 µg dose or ~32 mg/kg) in PBS buffer (experimental group 1), 100 µL of 1a at 8 µg/µL (800 µg dose or ~32 mg/kg) in PBS buffer containing 3 mg/kg doxorubicin (experimental group 2), 800 µg dose of doxorubicin-loaded nanoaggregates of Example 10 (containing 1 µg/µL doxorubicin) (experimental group 3). Nanoaggregates will be administered peritumorally, while all other treatments will be administered subcutaneously or intraperitoneally. Tumor volume measurements will made every three days, also starting on Day 1. Volume of tumors will measured by caliper. Mice will also be weighed every three days, with daily monitoring of food and water intake, as well as overall well-being. Mice will be sacrificed at the conclusion, and tumor volumes compared.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A conjugate of formula (I):

(A-Z$^1$-)$_n$-Q-Z$^2$-D     (I), wherein
Z$^1$ is not present;
Z$^2$ is —C(O)—;
Q consists of a single amino acid residue or a peptide containing two or three amino acid residues, wherein the N-terminal group of Q is linked to Z$^2$ and wherein one or more of the amino acid residues is optionally phosphorylated;
A is OH of the C-terminal carboxyl group of Q or an enzymatically cleavable moiety —NH—(CH$_2$)$_2$—O—C(O)—(CH$_2$)$_2$—C(O)—NH—(CH$_2$)$_2$—SO$_2$(OH);
D is a cholesterol moiety covalently bonded to Z$^2$ wherein the cholesterol moiety has the structure

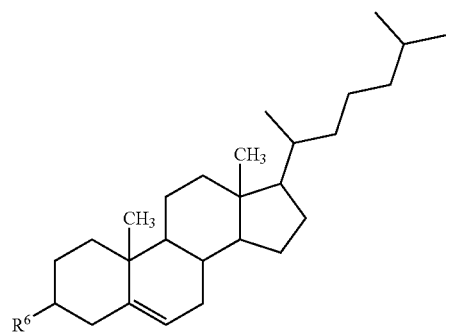

where R$^6$ is —O— bonded to Z$^2$; and
n is 1;
wherein at least one of (i) Q including a phosphorylated amino acid, or (ii) A being the enzymatically cleavable moiety —NH—(CH$_2$)$_2$—O—C(O)—(CH$_2$)$_2$—C(O)—NH—(CH$_2$)$_2$—SO$_2$(OH), is present; and
wherein the conjugate is capable of self-assembly in the presence of an enzyme that hydrolyzes the enzymatically cleavable-moiety or an enzyme that dephosphorylates the phosphorylated amino acid.

2. The conjugate according to claim 1, wherein Q is a single amino acid residue selected from phenylalanine, tyrosine, and phosphorylated tyrosine.

3. The conjugate according to claim 2, wherein the amino acid is phosphorylated tyrosine.

4. The conjugate according to claim 2, wherein the amino acid is a D-amino acid.

5. The conjugate according to claim 1, wherein Q is a dipeptide or tripeptide.

6. The conjugate according to claim 5, wherein the amino acids are all D-amino acids.

7. The conjugate according to claim 1, wherein A is OH.

8. The conjugate according to claim 1, wherein A is —NH—(CH$_2$)$_2$—O—C(O)—(CH$_2$)$_2$—C(O)—NH—(CH$_2$)$_2$—SO$_2$(OH).

9. The conjugate according claim 5, wherein dipeptide or tripeptide is selected from the group of tyrosinyl-lysine, (phospho)tyrosinyl-lysine, tyrosinyl-lysinyl-tyrosine, or (phospho)tyrosinyl-lysinyl-(phospho)tyrosine where the lysine or lysinyl residue optionally comprises a fluorophore, a chemotherapeutic agent, an antiangiogenic agent, an immunomodulator agent, an antibiotic, an antigen, or a thermoablative (paramagnetic) particle conjugated to its sidechain.

10. A conjugate comprising a cholesterol moiety covalently attached to an amino acid residue, and having one of the following structures:

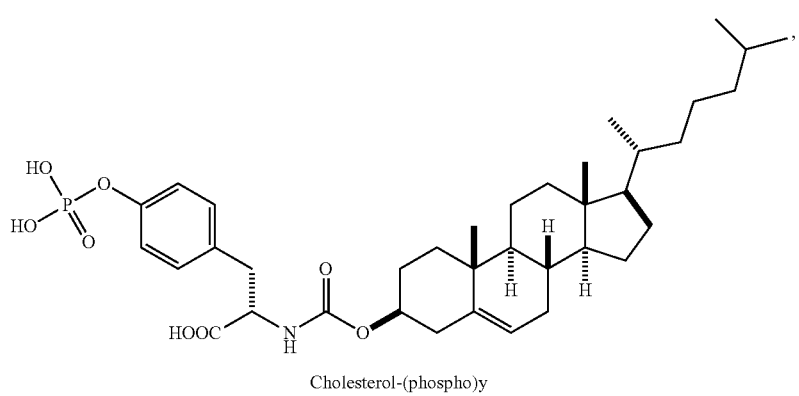

Cholesterol-(phospho)y

1a

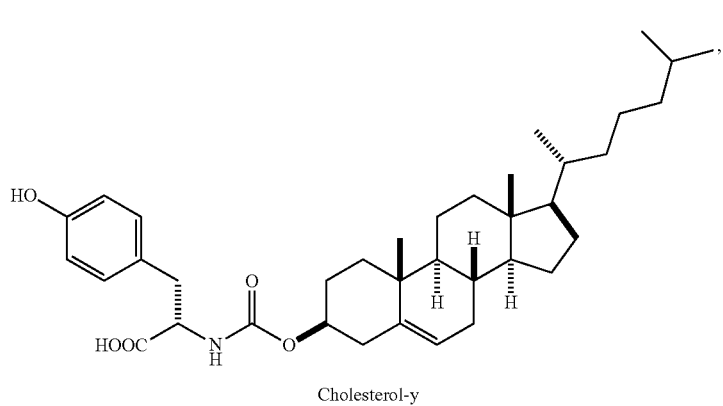

Cholesterol-y

1b

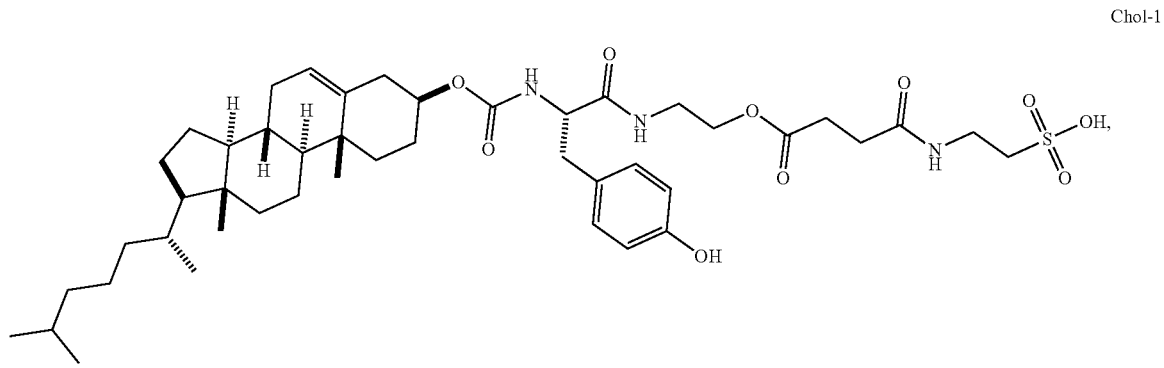

Chol-1

-continued
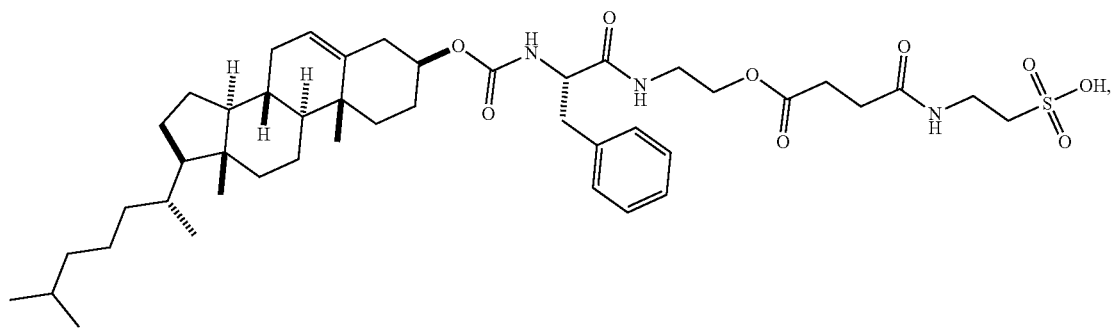
Chol-2
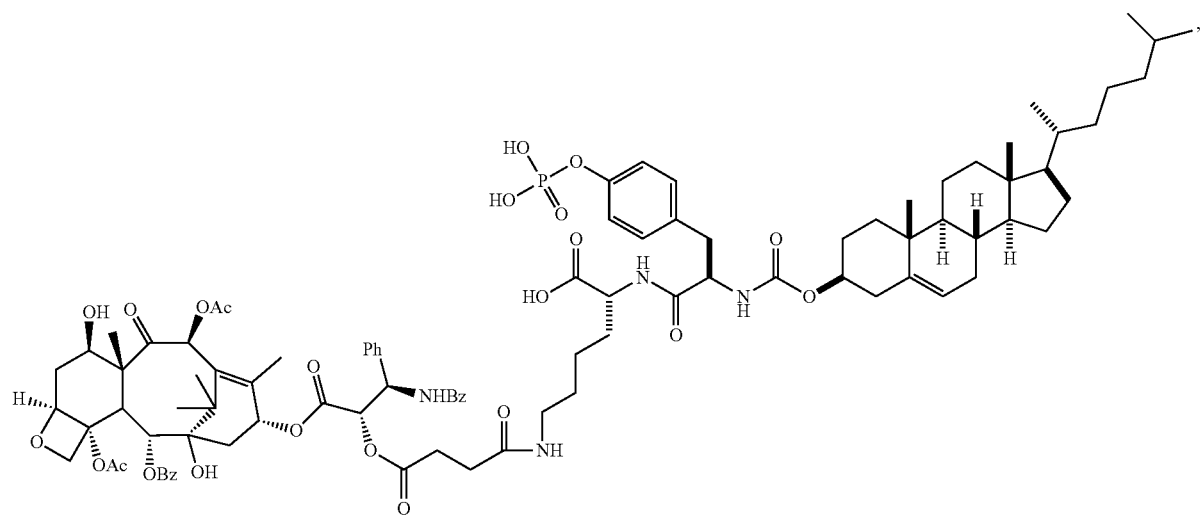
cholesterol-(phospho)y-(paclitaxel-succinyl)k
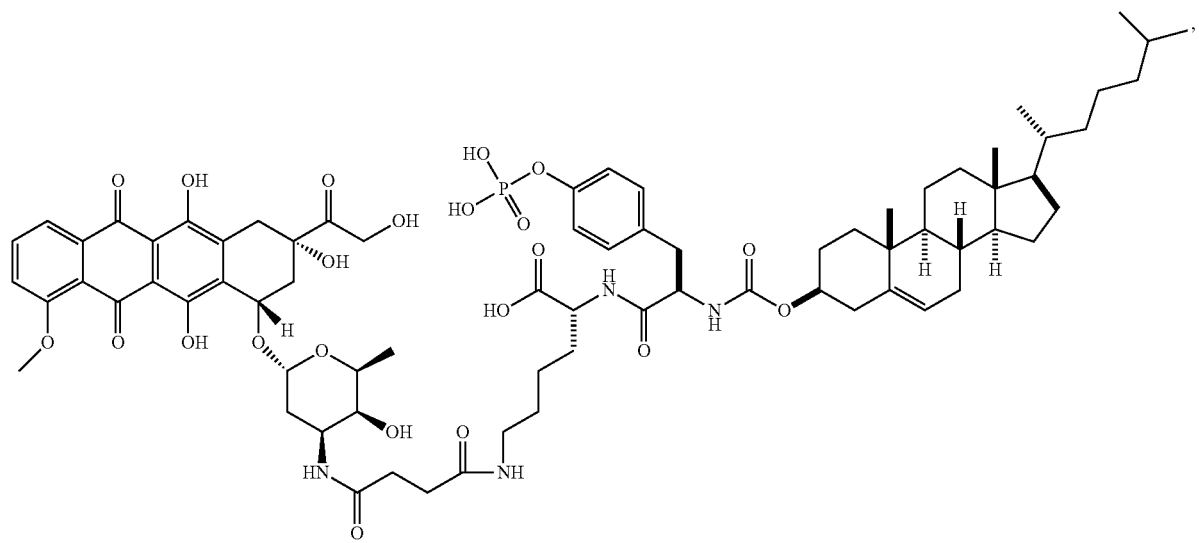
cholesterol-(phospho)y-(doxorubicin-succinyl)k

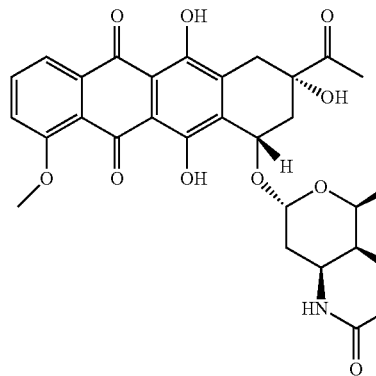
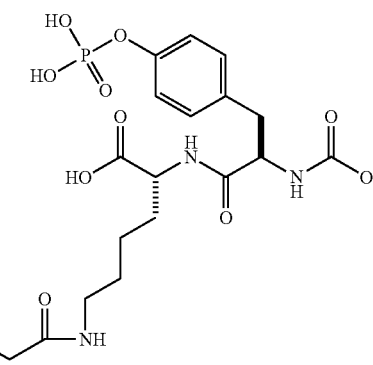
cholesterol-(phospho)y-(daunorubicin-succinyl)k
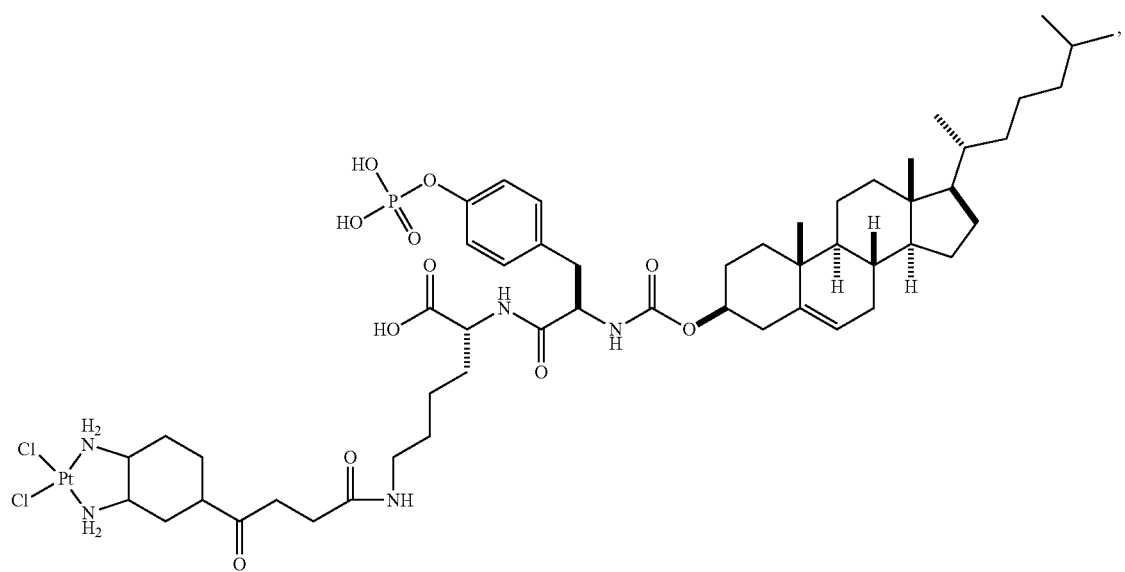
cholesterol-(phospho)y-(cisplatin prodrug-succinyl)k

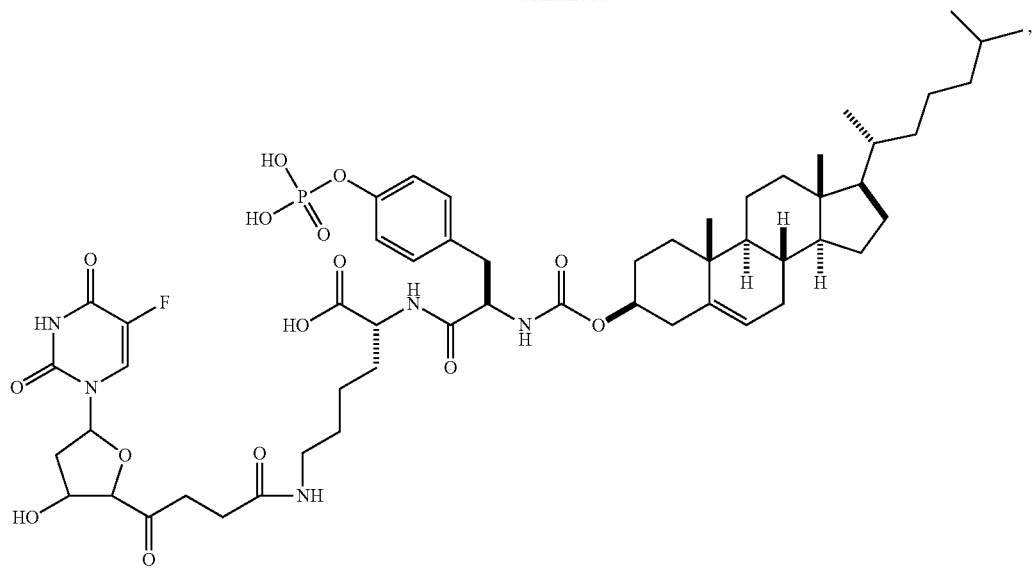
cholesterol-(phospho)y-(fluorouracil-4-hydroxy-3-succinyltetrahydrofuran-2-yl)k
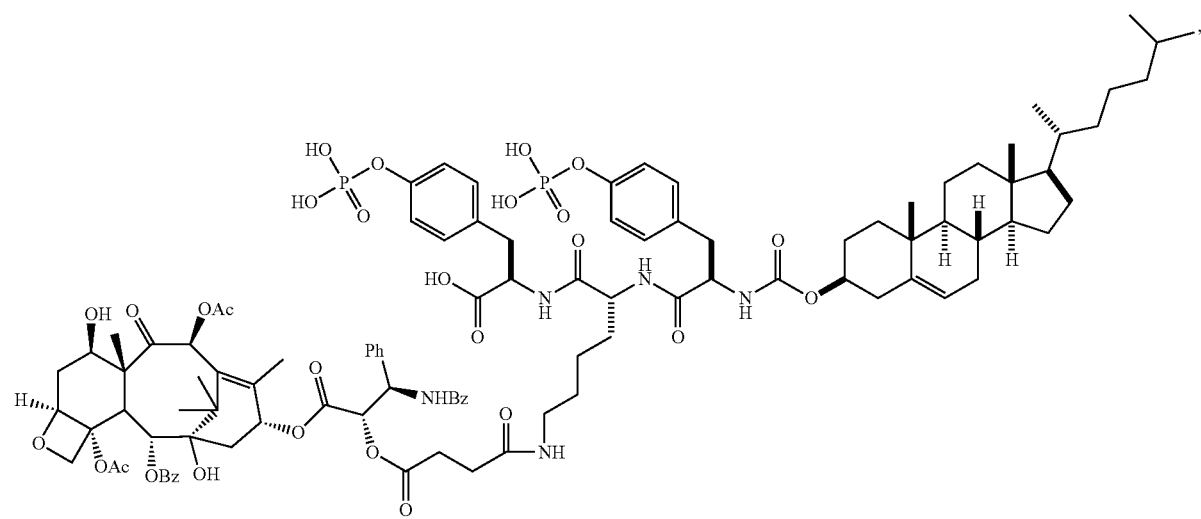
cholesterol-(phospho)y-(paclitaxel-succinyl)k-(phospho)y

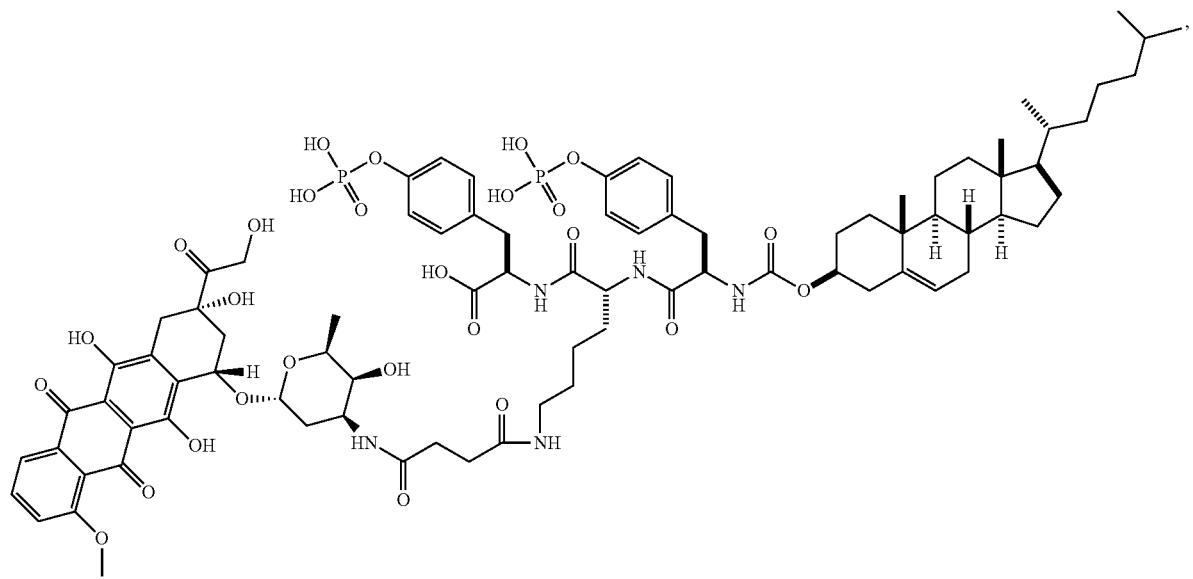
cholesterol-(phospho)y-(doxorubicin-succinyl)k-(phospho)y
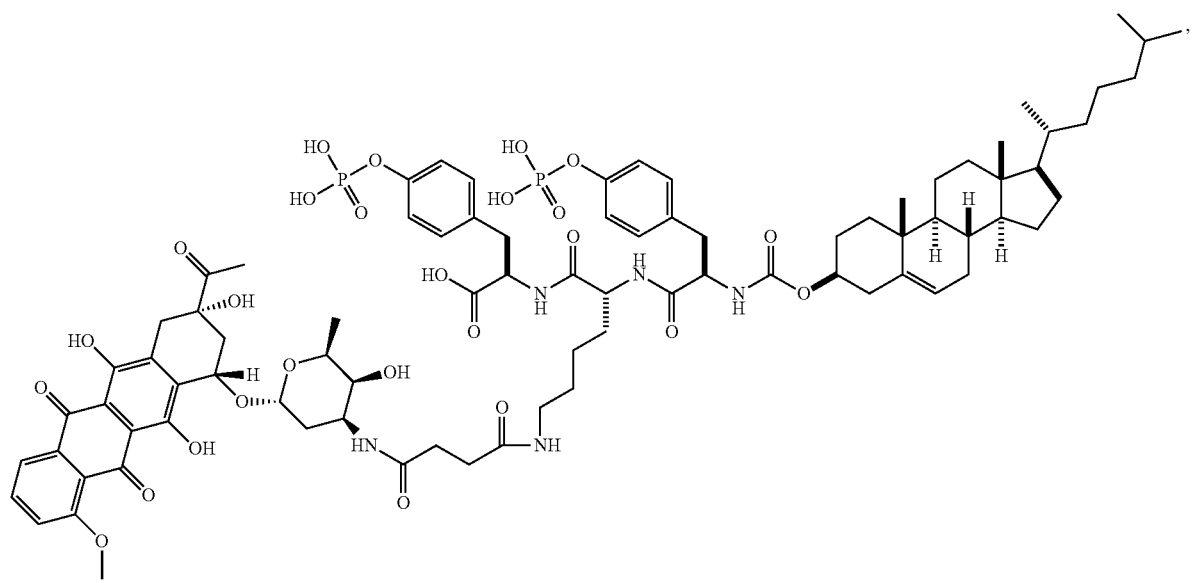
cholesterol-(phospho)y-(daunorubicin-succinyl)k-(phospho)y

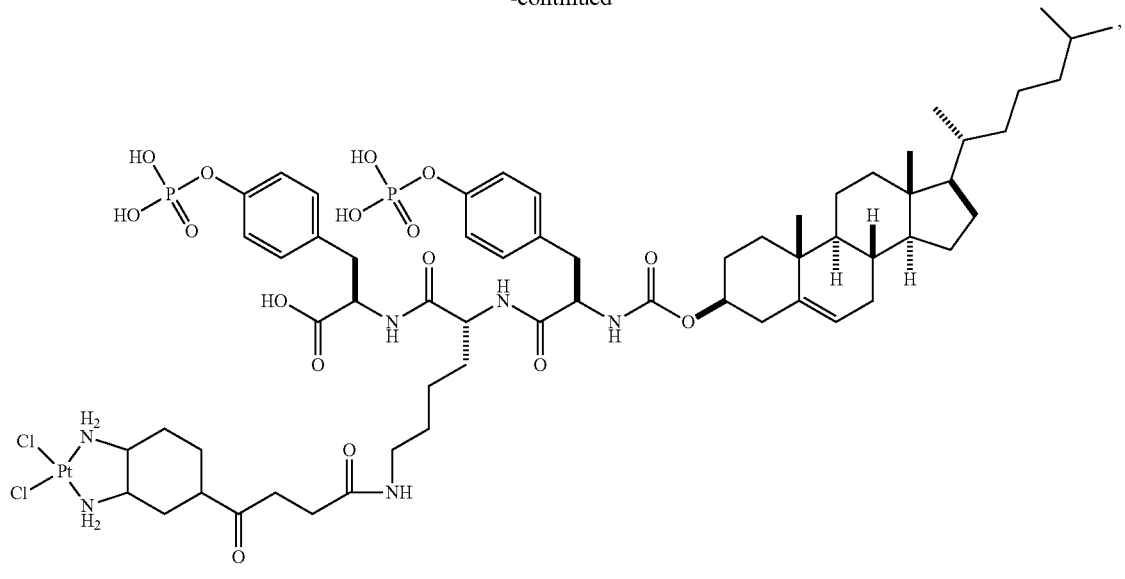

cholesterol-(phospho)y-(cisplatin prodrug-succinyl)k-(phospho)y

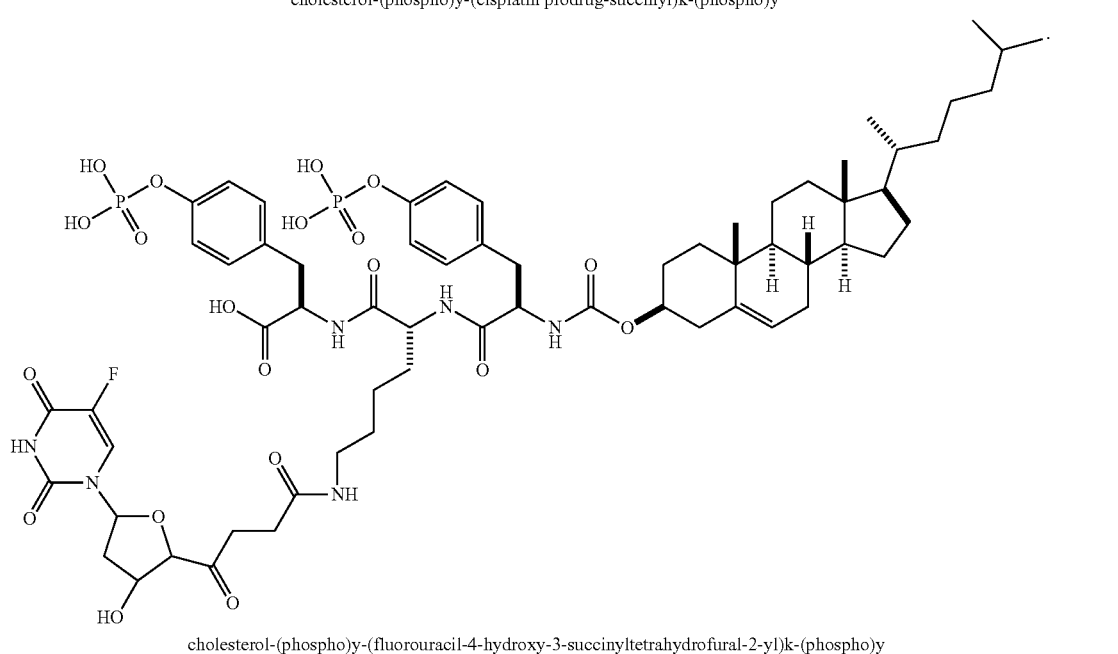

cholesterol-(phospho)y-(fluorouracil-4-hydroxy-3-succinyltetrahydrofural-2-yl)k-(phospho)y 11. A pharmaceutical composition comprising a pharmaceutically acceptable carrier and a conjugate according to claim 1.

12. The pharmaceutical composition according to claim 11 wherein the carrier is an aqueous medium.

13. The pharmaceutical composition according to claim 11, wherein the conjugate is present at a concentration of about 1 μM to about 10 mM.

14. The pharmaceutical composition according to claim 11, wherein the composition has a pH of about 6 to about 8.

15. The pharmaceutical composition according to claim 11, further comprising a chemotherapeutic agent, anti-neoplastic agent, an antiangiogenic agent, an immunomodulator agent, an antibiotic, an antigen, or a combination thereof.

16. The pharmaceutical composition according to claim 11, wherein the conjugate is present in the form of a nanoparticle aggregate.

17. A method for treating a cancerous condition comprising:
administering to a subject having a cancerous condition a therapeutically effective amount of the conjugate according to claim 1, wherein said administering is effective to cause intracellular or pericellular self-assembly of an enzymatically modified form of the conjugate in or around cancer cells that express an esterase that hydrolyzes the enzymatically cleavable-moiety —NH—(CH$_2$)$_2$—O—C(O)—(CH$_2$)$_2$—C(O)—NH—(CH$_2$)$_2$—SO$_2$(OH) or a phosphatase that dephosphorylates the phosphorylated amino acid; wherein said intracellular or pericellular self-assembly promotes cancer cell death to treat the cancerous condition.

18. The method according to claim 17, wherein said administering is carried out parenterally, subcutaneously, intravenously, intradermally, intramuscularly, intraperitoneally, by implantation, by intracavitary or intravesical instillation, intraarterially, intralesionally, intradermally, peritumorally, intratumorally, or by introduction into one or more lymph nodes.

19. The method according to claim 17 further comprising:
administering to the subject a chemotherapeutic agent, an immunotherapeutic agent, or a radiotherapeutic agent.

20. The method according to claim 17, wherein the subject is a mammal.

21. The method according to claim 17, wherein the subject is a human.

22. The method according to claim 17, wherein the cancer cell is present in a solid tumor.

23. The method according to claim 17, wherein the cancer cell is a metastatic cell.

24. The method according to claim 17, wherein the cancerous condition is selected from the group of cancers or neoplastic disorders of the brain and CNS, pituitary gland, breast, blood, lymph node, lung, skin, bone, head and neck, oral, eye, gynecological tissues, genitourinary, and gastrointestinal.

25. The method according to claim 17, wherein the conjugate or pharmaceutical composition is administered with a conjugate dose of between about 1 µg to about 100 mg.

26. A method for stimulating an immunoresponse comprising:
contacting a cell that expresses an esterase with hydrolytic activity or a phosphatase with the conjugate according to claim 1, wherein said contacting is effective to cause enzymatic cleavage of the enzymatically cleavable-moiety —NH—(CH$_2$)$_2$—O—C(O)—(CH$_2$)$_2$—C(O)—NH—(CH$_2$)$_2$—SO$_2$(OH) or dephosphorylation of the phosphorylated amino acid to form a modified conjugate, thereby causing intracellular or pericellular self-assembly of the modified conjugate, and stimulating an immune response against the contacted cell.

27. A method for forming a network on or near the inner or outer surface of target cells, the method comprising:
contacting a target cell that expresses a cell surface-bound enzyme having hydrolytic activity or phosphatase activity, secretes an enzyme having hydrolytic activity or phosphatase activity, or both, with the conjugate according to claim 1, wherein said contacting is effective to hydrolyze the enzymatically cleavable moiety —NH—(CH$_2$)$_2$—O—C(O)—(CH$_2$)$_2$—C(O)—NH—(CH$_2$)$_2$—SO$_2$(OH) or dephosphorylate the phosphorylated amino acid to form a modified conjugate and thereby cause in situ self-assembly of the modified conjugate to form a network on or near the inner or outer surface of the target cell.

28. A hydrogel comprising a plurality of conjugates according to claim 1, or the dephosphorylated conjugate or the conjugate comprising the enzymatic cleavage product of the moiety —NH—(CH$_2$)$_2$—O—C(O)—(CH$_2$)$_2$—C(O)—NH—(CH$_2$)$_2$—SO$_2$(OH), which are self-assembled in a plurality of nanofibers and/or nanoparticles.

29. A nanoparticle comprising a plurality of conjugates according to claim 1, or the dephosphorylated conjugate or the conjugate comprising the enzymatic cleavage product of the moiety —NH—(CH$_2$)$_2$—O—C(O)—(CH$_2$)$_2$—C(O)—NH—(CH$_2$)$_2$—SO$_2$(OH), which are self-assembled to form the nanoparticle.

30. A nanofiber comprising a plurality of conjugates according to claim 1, or the dephosphorylated conjugate or the conjugate comprising the enzymatic cleavage product of the moiety —NH—(CH$_2$)$_2$—O—C(O)—(CH$_2$)$_2$—C(O)—NH—(CH$_2$)$_2$—SO$_2$(OH), which are self-assembled to form the nanofiber.

31. The nanoparticle according to claim 29 further comprising a chemotherapeutic agent, an antineoplastic agent, an antiangiogenic agent, an immunomodulator agent, an antibiotic, an antigen, or a combination thereof.

32. A method for treating a cancerous condition comprising:
administering to a subject having a cancerous condition a therapeutically effective amount of the nanoparticle according to claim 29, wherein said administering is effective to treat the cancerous condition.

* * * * *

UNITED STATES PATENT AND TRADEMARK OFFICE
CERTIFICATE OF CORRECTION

PATENT NO. : 11,040,108 B2
APPLICATION NO. : 16/097325
DATED : June 22, 2021
INVENTOR(S) : Wang et al.

Page 1 of 1

It is certified that error appears in the above-identified patent and that said Letters Patent is hereby corrected as shown below:

In the Specification

At Column 1, Line 12, please delete "this" and insert --the-- in its place.

In the Claims

In Claim 10, at Column 71-72, please add --or-- immediately preceding the last structure.

In Claim 17, at Column 72, Line 62, please delete "acid;" and insert --acid-- in its place.

Signed and Sealed this
Twenty-eighth Day of December, 2021

Drew Hirshfeld
*Performing the Functions and Duties of the
Under Secretary of Commerce for Intellectual Property and
Director of the United States Patent and Trademark Office*